US008097405B1

(12) United States Patent
Engelhardt et al.

(10) Patent No.: US 8,097,405 B1
(45) Date of Patent: Jan. 17, 2012

(54) NUCLEIC ACID SEQUENCING PROCESSES USING NON-RADIOACTIVE DETECTABLE MODIFIED OR LABELED NUCLEOTIDES OR NUCLEOTIDE ANALOGS, AND OTHER PROCESSES FOR NUCLEIC ACID DETECTION AND CHROMOSOMAL CHARACTERIZATION USING SUCH NON-RADIOACTIVE DETECTABLE MODIFIED OR LABELED NUCLEOTIDES OR NUCLEOTIDE ANALOGS

(75) Inventors: Dean Engelhardt, New York, NY (US); Elazar Rabbani, New York, NY (US); Stanley Kline, Brooklyn, NY (US); Jannis G. Stavrianopoulos, New York, NY (US); Dollie Kirtikar, Elmhurst, NY (US)

(73) Assignee: Enzo Biochem, Inc., Farmingdale, NY (US)

( * ) Notice: Subject to any disclaimer, the term of this patent is extended or adjusted under 35 U.S.C. 154(b) by 0 days.

(21) Appl. No.: 08/486,069

(22) Filed: Jun. 7, 1995

Related U.S. Application Data

(60) Continuation of application No. 07/954,772, filed on Sep. 30, 1992, now abandoned, which is a continuation of application No. 07/548,348, filed on Jul. 2, 1990, now abandoned, which is a division of application No. 07/140,980, filed on Jan. 5, 1988, now abandoned, which is a continuation of application No. 06/674,352, filed on Nov. 21, 1984, now abandoned, which is a continuation of application No. 06/391,440, filed on Jun. 23, 1982, now abandoned.

(51) Int. Cl.
*C12Q 1/68* (2006.01)
*C12N 15/11* (2006.01)

(52) U.S. Cl. ............................................. 435/6; 536/24.3

(58) Field of Classification Search .................. 435/5, 6, 435/7.1, 91.1, 91.2, 810; 436/501, 63; 536/22.1, 536/23.1, 24.1, 24.3–24.33, 25.3; 735/77, 735/78
See application file for complete search history.

(56) References Cited

U.S. PATENT DOCUMENTS

| | | | |
|---|---|---|---|
| 3,906,031 A | 9/1975 | Carpino | |
| 3,931,397 A | 1/1976 | Harnden | 424/85 |
| 3,960,840 A | 6/1976 | Secrist, III et al. | 260/211.5 |
| 4,038,480 A | 7/1977 | Robins et al. | 536/27 |
| 4,119,521 A | 10/1978 | Chirikjian | |
| 4,124,702 A | 11/1978 | Lampson et al. | 424/85 |
| 4,151,065 A | 4/1979 | Kaplan | |
| 4,213,893 A | 7/1980 | Carrico et al. | 260/112.5 R |
| 4,230,797 A | 10/1980 | Boguslaski et al. | 435/7 |
| 4,255,566 A | 3/1981 | Carrico et al. | 536/27 |
| 4,260,737 A | 4/1981 | Scherberg | 536/25 |
| 4,293,310 A | 10/1981 | Weber | 436/536 |
| 4,310,662 A | 1/1982 | Crea | 536/27 |
| 4,313,938 A | 2/1982 | Arimura et al. | 424/180 |
| 4,318,846 A | 3/1982 | Khanna | |
| 4,358,535 A * | 11/1982 | Falkow et al. | 435/5 |
| 4,373,071 A | 2/1983 | Itakura | |
| 4,375,401 A | 3/1983 | Catsimpoolas | |
| 4,378,458 A | 3/1983 | Gohlke et al. | 536/29 |
| 4,401,796 A | 8/1983 | Itakura | |
| 4,415,732 A | 11/1983 | Caruthers | |
| 4,443,594 A | 4/1984 | Buckmann | 536/27 |
| 4,460,772 A | 7/1984 | Benovic et al. | 514/311 |
| 4,474,948 A | 10/1984 | Hudson | |
| 4,483,964 A | 11/1984 | Urdea | |
| 4,500,707 A | 2/1985 | Caruthers | |
| 4,517,338 A | 5/1985 | Urdea | |
| 4,534,647 A | 8/1985 | Gross | |
| 4,581,333 A * | 4/1986 | Kourilsky et al. | 435/6 |
| 4,598,049 A | 7/1986 | Zelinka | |
| 4,605,735 A | 8/1986 | Miyoshi et al. | 536/27 |
| 4,667,025 A | 5/1987 | Miyoshi | |
| 4,668,777 A | 5/1987 | Caruthers | |
| 4,707,440 A | 11/1987 | Stavrianopoulos | 435/6 |
| 4,708,935 A | 11/1987 | Suhadolnik et al. | 435/91 |
| 4,711,955 A * | 12/1987 | Ward et al. | 536/29 |
| 4,757,141 A | 7/1988 | Fung | |
| 4,828,979 A | 5/1989 | Klevan et al. | 435/6 |
| 4,833,251 A | 5/1989 | Musso et al. | 548/303 |
| 4,847,240 A | 7/1989 | Ryser | |

(Continued)

FOREIGN PATENT DOCUMENTS

DE A1814134 9/1970

(Continued)

OTHER PUBLICATIONS

Hartman et al., Biopolymers, vol. 20, No. 12, pp. 2635-2648, 1981.*
*Biochemistry* by Lehniger [Published by Worth Publishers, Inc., 70 Fifth Avenue, New York, NY 10011] pp. 638-639, 1970.*
Dunn et al., Cell vol. 12, pp. 23-26, 1977.*
Becker et al., "Irreversible Inhibition of Biotin Transport in Yeast by Biotinyl-p-nitrophenyl Ester," *Proc. Nat'l. Acad. Sci.* (USA) 68:2604-2607 (1971).

(Continued)

*Primary Examiner* — John S Brusca
(74) *Attorney, Agent, or Firm* — Natalie Bogdanos, Esq.; Elie Gendloff, Esq.

(57) ABSTRACT

A process for determining the sequence of nucleic acids of interest employs nucleotides or nucleotide analogs that have been made detectable by non-radioactive modifying or labeling. Such nucleotides or nucleotide analogs are modified on the sugar moieties, the phosphate moieties or the base moieties, including base analogs. Modified nucleotide analogs can be attached to or coupled to or incorporated into DNA or RNA. The modified or labeled nucleotides or nucleotide analogs are also useful in processes for detecting the presence of nucleic acids of interest and for characterizing chromosomal sequences. Detection processes using the modified or labeled nucleotides or nucleotide analogs extend to the use of a gel for separating or resolving hybrids formed between non-radioactively labeled oligonucleotides or polynucleotides and such nucleic acids of interest.

198 Claims, 4 Drawing Sheets

U.S. PATENT DOCUMENTS

| | | | |
|---|---|---|---|
| 4,849,513 A | 7/1989 | Smith | |
| 4,855,225 A | 8/1989 | Fung | |
| 4,880,918 A | 11/1989 | Rapaport | 536/27 |
| 4,948,882 A * | 8/1990 | Ruth | 536/27 |
| 5,015,733 A | 5/1991 | Smith | |
| 5,118,800 A | 6/1992 | Smith | |
| 5,118,802 A | 6/1992 | Smith | |
| 5,162,654 A | 11/1992 | Kostichka | |
| 5,171,534 A | 12/1992 | Smith | |
| 5,212,059 A | 5/1993 | Schwartz | |
| 5,212,304 A | 5/1993 | Fung | |
| 5,241,060 A * | 8/1993 | Engelhardt et al. | 536/27 |
| 5,242,906 A | 9/1993 | Pagano | |
| 5,258,538 A | 11/1993 | Fung et al. | |
| 5,260,433 A * | 11/1993 | Engelhardt et al. | 536/23.1 |
| 5,366,860 A | 11/1994 | Bergot | |
| 5,541,311 A | 7/1996 | Dahlberg | |
| 5,591,600 A | 1/1997 | Ecker | |
| 5,591,720 A | 1/1997 | Anderson | |
| 5,614,617 A | 3/1997 | Cook | |
| 5,643,730 A | 7/1997 | Banker | |
| 5,643,780 A | 7/1997 | Baker | |
| 5,652,094 A | 7/1997 | Usman | |
| 5,665,710 A | 9/1997 | Rahman | |
| 5,736,294 A | 4/1998 | Ecker | |
| 5,807,677 A | 9/1998 | Eigen | |
| 5,811,232 A | 9/1998 | Crooke | |
| 5,874,564 A | 2/1999 | Ecker | |
| 5,891,468 A | 4/1999 | Martin | |
| 5,914,230 A | 6/1999 | Liu | |
| 5,998,383 A | 12/1999 | Wright | |

FOREIGN PATENT DOCUMENTS

| | | |
|---|---|---|
| DE | A1617886 | 1/1971 |
| DE | A2507901 | 9/1976 |
| EP | 0027631 B1 | 4/1981 |
| EP | 0061760 A1 | 10/1982 |
| EP | 0061761 A1 | 10/1982 |
| EP | 0061762 A2 | 10/1982 |
| EP | 0063879 B1 | 11/1982 |
| EP | 0068875 | 1/1983 |
| EP | 0070687 | 1/1983 |
| EP | 0090789 | 10/1983 |
| EP | 0097341 | 1/1984 |
| EP | 0169787 A1 | 1/1986 |
| EP | 0225807 A2 | 6/1987 |
| EP | 0261283 | 3/1988 |
| GB | 2019408 * | 10/1979 |
| GB | 2019408 A | 10/1979 |
| GB | 2036204 A | 6/1980 |
| GB | 2040943 | 9/1980 |
| GB | 2153356 | 8/1985 |
| JP | S49126395 | 12/1974 |
| JP | 53133283 | 11/1978 |
| JP | 57011999 | 1/1982 |
| JP | S58502205 | 12/1983 |
| JP | S5944648 | 3/1984 |
| JP | S5993100 | 5/1984 |
| JP | S59126252 | 7/1984 |
| JP | 6096610 | 5/1985 |
| JP | S60161559 | 8/1985 |
| JP | 60169495 | 9/1985 |
| JP | S60242368 | 12/1985 |
| JP | 57042632 | 3/1986 |
| JP | 61103824 | 5/1986 |
| SU | A659573 | 4/1979 |
| WO | 8302276 | 7/1983 |
| WO | 8302277 | 7/1983 |
| WO | 8303260 | 9/1983 |
| WO | 8602929 | 5/1986 |
| WO | 8606726 | 11/1986 |
| WO | 8607361 | 12/1986 |

OTHER PUBLICATIONS

Halloran et al., "The Preparation of Nucleotide-protein Conjugates: Carbodiimides as Coupling Agents," *J. Immunol.*, 96:373-378 (1966).

Manning et al., "A New Method of in situ Hybridization," *Chromosoma*, 53:107-117 (1975).

Kropinski et al., "5-(4-Aminobutylaminomethyl) uracil, an Unusual Pyrimidine from the Deoxyribonucleic Acid of Bacteriophage øW-14," *Biochemistry*, 12:151-157 (1973).

Torrence et al., "5-0-Alkylated Derivatives of 5-Hydroxy-2'-deoxyuridine as Potential Antiviral Agents. Anti-Herpes Activity of 5-Propynyloxy-2'-deoxyuridine," *J. Med. Chem.*, 21:228-231 (1978).

Michelson, "Synthesis of Nucleotide Anhydrides by Anion Exchange," *Biochem. Biophys. Acta.*, 91:1-13 (1964).

Cech et al. "A facile synthesis of 5-(perfluoroalkyl)-pyrimidines," *Nucl. Acids Res.*, 2:2183-2192 (1979).

Schram et al., "Pyrrolopyrimidine Nucleosides VIII. Synthesis of Sangivamycin Derivatives Possessing Exocyclic Heterocycles at C5," *J. Carbohydrate. Nucleosides. Nucleotides*, 1:39-54 (1974).

Bleackley et al., "The preparation of 5-cyanouracil and 5-cyano-2'-deoxyuridine from the corresponding 5-iodo derivative and cuprous cyanide," *Nucl. Acids Res.*, 2:683-690 (1975).

Roberts et al., "Uridine and Cytidine Derivatives," *J. Am. Chem. Soc.* 74:668-669 (1952).

Bauman et al., "Rapid and High Resolution Detection of in situ Hybridisation to Polytene Chromosomes Using Fluorochrome-labeled RNA," *Chromosoma*, 84:1-18 (1982).

Bauman et al., "A new method for fluorescene microscopical localization of specific DNA sequences by in situ hybridization of fluorochrome-labelled RNA," *Exp. Cell Res.*, 128:485-490 (1980).

Gerhard et al., "Localization of a Unique Gene by Direct Hybridization in situ," *Proc. Natl. Acad. Sci.* (USA), 78:3755-3759 (1981).

Miller, J., "Experiment 52, Assay of the lac Repressor by Binding to Operator," *Experiments in Molecular Genetics*, Cold Spring Harbor Laboratory, pp. 367-370 (1972).

Ueda et al., "Conversion of Uridine Nucleotides to the 6-Cyano Derivatives: Synthesis of Orotidylic Acid (Nucleosides and Nucleotides)," *J. Carbohydr., Nucleosides, Nucleotides*, 5:261-271 (1978).

Brunngraber et al., "Purification and Properties of a Nucleoside Phosphotransferase from Carrot," *J. Biol. Chem.*, 242:4834-4840 (1967).

Wilchek et al., "Modification of the Carboxyl Groups of Ribonuclease by Attachment of Glycine or Alanylglycine," *Biochemistry*, 6:247-252 (1967).

Vogt, "Purification and Properties of $S_1$ Nuclease from *Aspergillus*," *Methods in Enzymology*, 65:248-255 (1980).

Monod et al., "On the Nature of Allosteric Transitions: A Plausible Model," *J. Mol. Biol.*, 12:88-118 (1965).

Pastan et al., "Cyclic Adenosine Monophosphate in Bacteria," *Science*, 169:339-344 (1969).

Gilbert et al., "The Nucleotide Sequence of the lac Operator," *Proc. Natl. Acad. Sci.* (USA), 70:3581-3584 (1973)

Pardee, "Membrane Transport Proteins," *Science*, 162:632-637 (1968).

Hazelbaur et al., "Role of the Galactose Binding Protein in Chemotaxis of *Escherichia coli* toward Galactose," *Nature New Bio.*, 230:101-104 (1971).

Langer et al., "Enzymatic synthesis of biotin-labeled polynucleotides: Novel nucleic acid affinity probes," *Proc. Natl. Acad. Sci. (USA)*, 78:6633-6637 (1981).

Nishimura et al., "Synthetic Nucleosides and Nucleotides. XV. 1) 5-Dimethylamino-2-oxidoisoquinolin-1-yl Diazomethane: A Novel Water-Soluble Fluorescent Labelling Agent for Nucleotides," *Chem. Pharm Bull.*, 28:1695-1703 (1980).

Kwah et al., "Myocardinal Infarct Imaging of Antibodies to Canine Cardiac Myosin with Indium-111-Diethylenetriamine Pentaacetic Acid," *Science* 209:295-297 (1980).

Torrence, et al., "Interferon Inducers: General Survey and Classification," *Methods in Enzymology*, vol. 78, Interferons, Part A, pp. 291-299 (Pestka, Edu.), Academic Press, New York, 1981.

Siebenlist et al., "Contacts between *Escherichia coli* RNA polymerase and an early promoter of phage T7," *Proc. Natl. Acad. Sci.* (USA), 77:122-126, Jan. 1980.

Maxam et al., "A New Method for Sequencing DNA," *Proc. Natl. Acad. Sci.* (USA), 74:560-564, 1977.

Heggeness et al., "Avidin Binds to Condensed Chromatin," *Stain Technol.* 52:165-169 (1977).
Heggeness et al., "Use of the Avidin-Biotin Complex for the Localization of Actin and Myosin with Fluorescence Microscopy," *J. Cell Biol.* 73:783-788 (1977).
Bayer et al. "The Use of the Avidin-Biotin Complex as a Tool in Molecular Biology," *Methods of Biochem Analysis* 26:1-45 (1980).
Hoffman et al., "Iminobiotin Affinity Columns and Their Application to Retrieval of Streptavidin," *Proc. Natl. Acad. Sci.* 77:4666-4668 (1980).
Pardue et al., "Nucleic Acid Hybridization to the DNA of Cytological Preparations," *Methods in Cell Biol.* 10:1-16 (1975).
Bergstrom et al., "C-5 Substituted Pyrimidine Nucleosides. 2. Synthesis via Olefin Coupling to Organopalladium Intermediates Derived from Uridine and 2'-Deoxyuridine," *JACS* 100:8106-8112 (1978).
Bigge et al., "Palladium-Catalyzed Coupling Reactions of Uracil Necleosides and Nucleotides," *JACS* 102:2033-2038 (1979).
Rigby et al., "Labeling Deoxyribonucleic Acid to High Specific Activity in Vitro by Nick Translation with DNA Polymerase I," *J. Mol. Biol.* 113:1237-251 (1977).
Bourguignon et al., "DNA of Minute Virus of Mice:Self-Priming, Nonpermutated Single-Stranded Genome with, a 5'-Terminal Hairpin Duplex," *J. Virol.* 20:290-306 (1976).
Miller et al., "A general method for permeabilizing mono-layer and suspension cultured animal cells," *Exp. Cell Res.* 120:421-425 (1979).
Schulman et al., "Attachment of protein affinity-labeling reagents of variable length and amino acid specificity to E. coli tRNA$^{fMet}$," *Nuc. Acid Res.*, 9:1203-1217 (1981).
Langer, et al., "Enzymatic synthesis of biotin-labeled polynucleotides: Novel nucleic acid affinity probes," *Chemical Abstracts*, vol. 96, No. 7, Feb. 15, 1982, p. 207, Abstract No. 47771z.
Clechet, P. et al., "Trace analysis of barium in water by means of cation resin-loaded paper and x-ray fluorescence analysis," *Chemical Abstracts*, vol. 94, No. 25, Jun. 22, 1981, p. 366, Abstract No. 214298t.
Duke et al., "Conformational change accompanying modification of myosin ATPase," *Chemical Abstracts*, vol. 66, No. 9, Feb. 27, 1967, p. 3326, Abstract No. 35045h.
Duke et al., "Conformational change accompanying modification of myosin ATPase," *Biochem. Bioahys. Acta*, 126:600-603 (1966).
Kathawala et al., "Darstellung von Desoxy-oligonucleotiden Mit 2'.3'-[2.4-Dimethoxy-benzyliden]-uridin als Phosphat-Schutzgruppe," *Liebigs Ann. Chem.*, 712:195-200 (1968).
Trouet et al., "Targeting of antitumor and antiprotozoal drugs by covalent linkage to protein carriers," *Chemical Abstracts*, vol. 98, No. 9, Feb. 28, 1983, p. 334-335, Abstract No. 77997m.
Trouet et al., "Targeting of antitumor and antiprotozoal drugs by covalent linkage to protein carriers," *NATO Adv. Study Inst. of Targeting of Drugs, Series A, Life Sciences*, 47:19-30, Plenum Press, New York (1981).
Angerer at al., "An Electron Microscope Study of the Relative Positions of the 4S and Ribosomal RNA Genes in HeLa Cell Mitochondrial DNA," *Cell* 9:81-90 (1976).
Mackey at al., "Preparation and Characterization of Highly Radioactive in Vitro Labeled Adenovirus DNA and DNA Restriction Fragments" *Biochemistry*, 16:4478-4482 (1977).
Zhenodarova et al., "Spin-labeled Derivatives of Oligoribonucleotides as Spin Probes for Studying the Mechanism of the Effect of Enzymes," *Chemical Abstracts*, vol. 91, 1979, p. 303, Abstract No. 85951n.
Salam et al., "Synthesis of Nucleoside 5'-(β-D-Glucopyranosyl Monophosphates) by the Sugar Ortho Ester Route," *Carbohydrate Research*, 102:139-146 (1982).
Salam et al., "Synthesis of Acetylated α-and β-L-Fucosyl Esters of Nucleoside 5'-Monophosphates by the Orthoester Route," *Nucleosides & Nucleotides*, 1:155-161 (1982).
Maxam, A.M. and Gilbert, W., "Sequencing End-Labeled DNA with Base-Specific Chemical Cleavages," *Methods in Enzymology* 65:499-559 (1980).
Sanger, F. et al., "DNA sequencing with chain-terminating inhibitors," *Proc. Natl. Acad. Sci.* (USA) 74(12):5463-5467 (1977).

Akusjarvi G., and Pettersson, U., "Nucleotide sequence at the junction between the coding region fo the adenovirus 2 hexon messenger RNA and its leader sequence," *Proc. Natl. Acad. Sci.* (USA) 75(12):5822-5826 (1978).
Kitamura N. and Wimmer E., "Sequence of 1060 3'-terminal nucleotides of poliovirus RNA as determined by a modification of the dideoxynucleotide method," *Proc. Natl. Acad. Sci.* (USA) 77(6):3196-3200 (1980).
Yoshioka et al., "Method for determining a DNA nucleotide sequence I," *Cell Engineering* 1(1):93-101 (1982).
Lee, D.C. and Roeder, R.G., "Transcription of Adenovirus Type 2 Genes in a Cell-Free System: Aparent Heterogeneity of Initiation at Some Promoters," *Molecular and Cellular Biology* 1(7):635-651 (1981).
Nomiya et al., "Method for determining a DNA nucleotide sequence II," *Cell Engineering* 1(2):105-115 (1982).
Draper, D.E. and Gold, L., "A Method for Linking Fluorescent Labels to Polynucleotides: Application to Studies of Ribosome-Ribonucleic Acid Interactions," *Biochemistry* 19(9):1774-1781 (1980).
Bouloy M. et al., "Cap and Internal Nucleotides of Reovirus mRNA Primers are Incorporated into Influenza Viral Complementary RNA During Transcription in Vitro," *Journal of Virology* 32(3):895-904 (1979).
Plotch S.J. et al., "Transfer of 5'-terminal cap of globin mRNA to influenza viral complementary RNA during transcription in vitro," *Proc. Natl. Acad. Sci.* (USA) 76(4)1618-1622 (1979).
Kagakukai ed., "Fluorescence tagging" *Biochemistry Experiments Course 2, Nucleic Acid Chemistry III*, pp. 299-317 (1977).
Yang, C-H., and Soll, D., "Studies of Transfer RNA Tertiary Structure by Singlet-Singlet Energy Transfer," *Proc. Natl. Acad. Sci.* (USA) 71(7):2838-2842 (1974).
Douglass et al., "Methods and instrumentation for fluorescence quantitation of proteins and DNA's in electrophoresis gels at the I ng level," *Electrophoresis '78* N. Catsimpoolas, ed., pp. 155-165 (1978).
Gilbert W., "DNA-sequenzierung and gon-struktur (Nobel-Vortrag,}" *Angenwandte Chemie* 93:1037-1046 (1981).
Gilbert W., "DNA Sequencing and Gene Structure," *Science* 214(18):1305-1312 (1981).
Maxam, A.M. and Gilbert, W., "Sequencing End-Labeled DNA with Base-Specific Chemical Cleavages," *Methods in Enzymology* 65:499-504 (1980).
Sanger et al., "DNA Sequencing With Chain Terminating Inhibitors," *Proc. Natl. Acad. Sci* (USA) 74:5463-5467 (1977).
Smith A.J.H., "DNA Sequence Analysis by Primed Synthesis," *Methods in Enzymology* 65:560-580 (1980).
Barrio J.R. et al., "Fluorescent Adenosine and Cytidine Derivatives," *Biochemical and Biophysical Research Communications* 46(2):597-604 (1972).
Eshaglpour, H. et al., "Specific chemical labeling of DNA fragments," *Nucl. Acids Res.* 7(6):1485-1495 (1979).
Guo et al., "New rapid methods for DNA sequencing based on exonuclease III digestion followed by repair synthesis," *Chem. Abst.* 97:162 (abstract No. 1521k) (1982).
Fiddes, J.C., "Isolation, cloning and sequence analysis of the cDNA for the α-subunit of human chorionic gonadotropin," *Nature* 281(4):351-356 (1979).
Husimi, Y. "DNA Sequences," *Oyo Buturi* 51(12)1400 (1982).
Secrist, J.A. et al., "Fluorescent modification of cyclic amp spectroscopic properties and activity in enzyme systems," *Science* 177:279-280 (1972).
Stanley et al., "A difference approach to RNA sequencing," *Nature* 274:87-89 (1978).
Tsuchiya M. et al., "Developments of DNA fluorescent labeling and real-time fluorescent detection gel electrophoresis methods," *Biophysics* 22: 20-E-19 (1982).
Ulanov et al., "Electron microscopic determination of guanosine localization in DNA," *Chem. Abst.* 67:1692 (1967) (abstract No. 17910c).
Titus, J.A. et al., "Texas Red, a hydrophilic red-emitting fluorophore for use with fluorescein in dual parameter flow microfluorometric and fluorescence microscopic studies," *Journal of Immunological Methods* 50:193-204 (1982).

Langmore J.P. and Crewe A.V., "Progress Towards the Sequencing of DNA by Electron Microscopy," Proceedings, *Thirty-Second Annual Meeting, Electron Microscopy Society of America*, Aug. 1315, 1974, St. Louis, Mo., Ed., Arceneaux, C., p. 376-377, (1974), Claitor's Publishing Division: Baton Rouge, LA, USA (1974).

Partial Translation in English of "Biochemistry Experiments Course 2, Nucleic Acid Chemistry III—Methods of Higher Order Structure Study—"pp. 299-317 (1977), edited by Nihon Kagakukai, issued Feb. 25, 1977.

Gilbert, W., "DNA Sequencing and Gene Structure," Nobel lecture, Dec. 8, 1980, Harvard University, The Biological Laboratories, Cambridge, Mass. 02138 (USA).

Gilbert, W., *Science* (14):1305-1312, (Dec. 18, 1981); and.

Gilbert, W., *Bioscience Reports 1*:353-375 (1981).

English translation of Fushing, Y. "DNA Sequences," *Oyo Buturi 51*(12):1400 (1982).

English translation of Ulanov, B.P. and Malysheva, L.F., "Potentials for Localization of Guanine in DNA by Electron Microscopy," *Biophysics*, vol. XII(2):325-326 (1967).

English translation of Ulanov, B.P. et al., "On the Problem of Determination of Base Sequence in Nucleic Acids," *Biophysics*, vol. XII (2):326-330 (1967).

Rose, S.D., "Mercuration of Modified Nucleotides: Chemical Methods Toward Nucleic Acid Sequencing by electron Microscopy," *Biochimica et Biaphysica Acta 361*:231-235 (1974).

Salser, W.A., "DNA Sequencing Techniques," *Annual Review of Biochemistry 43*:923:965 (1974).

Whiting, R.F. and F.P. Ottenseyer, "Platinum DMSO: An Adenine-Specific Stain for DNA Sequencing by Electron Microscopy," Abstract W-PM-J14 Presented at Biophysical Society Program and Abstracts, Nineteenth Annual Meeting, Feb. 18-21, 1975, Philadelphia, PA, published in *Biophysical Journal 15*:98a (1975).

Frizell, J., "A Possible Electron Dense Label for the Use in the Sequencing of DNA by Electron Microscopy," *Journal of Theoretical Biology 59*:241-242 (1976).

*Organic Chemistry of Nucleic Acids, Part B*, Chapter 9, "Reactions of the Carbohydrate Residues of Nucleic Acids," pp. 449-476, Edited by Kochetkov, N.K. and Budovskii, F.I., Plenum Press. London and New York (1972).

Armstrong, V.W. and Eckstein, F., "Interaction of Substrate Analogues with *Escherichia coli* DNA-Dependent RNA Polymerase," *Eur. J. Biochem 70*: 33-38 (1976).

Rozovskaya, T.A. et al., "Introduction of a Fluorescent Label at the 3 OH End of DNA and the 3 OH End of the Growing RNA Chain," *Molekulyamaya Biologiya 11*(3): 598-610 (1977).

Petrov A.I. and Sukhorukov B.I., "Spin-labeled polyribonucleotides," Nucleic Acids Research 8(18): 4221-4234 (1980).

Hiratsuka, T. and Uchida, K., "Preparation and Properties of 2 (or 3)-O-(2,4,6-Trinitrophenyl) Adenosine 5'-Triphosphate, an Analog of Adenosine Triphosphate," *Biochimica et Biophysica Acta 320* 635-647 (1973).

Bauman J.G.J. et al., "Cytochemical Hybridization with Fluorochrome-labeled RNA," *J Histochem. Cytochem. 29*: 227-237 (1981).

Broker T.R. et al., "Electron microscopic visualization of tRNA genes with ferritin-avidin: biotin labels," *Nucleic Acids Research 5*(2): 363-384 (1978).

Sodja A. and Davidson N., "Gene mapping and gene enrichment by the avidin-biotin interaction: use of cytochrome-c as a polyamine bridge." *Nucleic Acids Research 5*(2): 385-401 (1978).

Daniel F.B. and Behrman E.J., "Osmium (VI) Complexes of the 3',5'-Dinucleoside Monophosphates. ApU and UpA," *Biochemistry 15*: 565-568 (1976).

Eberhard W. et al., "Galactopyranosyl-β(1 3')-ribonucleosides-structural evidence and synthesis," *Nucleic Acids Research Symposium Series No. 9*: 15-19 (1981).

Saffhill, R. and Hall, J., "A Convenient Preparation of Isomerically Pure Nucleoside 5' Monophosphates From Unprotected Nucleosides," *J. Carbohydrates Nucleosides Nucleotides 8*(6): 573-553 (1981).

Erlanger, B.F. et al., "Antibodies Specific for Ribonucleosides and Ribonucleotides and Their Reaction with DNA," *Proc. Natl. Acad. Sci. 52*: 6R-74 (1964).

Suzuki S., et al., "The Binding Sites of Nucleosides or Nucleotides to Diethylenetriaminecobalt (III)," *Bioinorganic Chemistry 3*: 281-293 (1974).

Petrov, A.I., "Complex formation between spin-labeled polyuridylic acid and pyrimidine nucleosides," *Nucleic Acids Research 8*(23): 5913-5929 (1980).

Lippard, S.J., "Platinum Complexes, Probes of Polynucleotide Structure and Antitumor Drugs," *Accounts of Chemical Research 11* (1978), 211-217.

Hampton, A., "Studies of the Action of Adenylosuccinase with 6-Thio Analogues of Adenylosuccinic Acid," *J. Biol. Chem. 237* (1962), 529-535.

Beer, M. et al., "Biological Structure Determination Through Atomic Microscopy," *Chcmica Scnpta 14* (1979), 263-266.

Chang, C-H. et al., "Osmium-Labeled Polynucleotides. The Reaction of Osmium Tetroxide with Deoxyribonucleic Acid and Synthetic Polynucleotides in the Presence of Tertiary Nitrogen Donor Ligands," *Biochemistry 16* (1977), 33-38.

Brossmer et al., "Synthese von 5-(α-1)-Glucopyranosyloxymethl)-3-(β-D-ribofuranosyl)uracil and 3-(2- Desoxy- β-D-ribofuranosyl)-5-( α-D-glucopyranosyloxymethyl)uracil als Analoga eines DNA-Bausteins," *Leibings Ann. Chem* 975-981 (1974).

Chheda, G.B., "Isolation and characterization of $N^6$-succinyladenosine from human urine," *Nucleic Acid Research 4*739-746 (1977).

Limback et al., "Summary: the modified nucleosides of RNA," *Nucleic Acids Research 22* 2183-2196 (1994).

Delaney, E.J. et al., "Synthesis of 5'Substituted EDTA-Like Nucleosides as Analogs of Nucleoside Phosphates," *J. Carbohydrates Nucleosides Nucleotides 8* 445-459 (1981).

Raggazzo and Behrman, "The Reactions of Oxo-Osmium Ligand Complexes with Isopentenyl Adenine and Its Nucleoside," *Bioinorganic Chem. 5* 343-352 (1976).

Hoard, D.E. and Ott, D.G., "Conversion of Mono- and Oligodeoxyribonucleotides to 5'-Triphosphates," *J. Am. Chem. Soc. 87* 1785-1788 (1965).

Martell and Calvin, *Chemistry of the Metal Chelate Compounds*, Prentice Hall, Englewood Cliffs NJ, USA 136.

Dwyer, F.W. and Mellor, D.P., *Chelating Agents and Metal Chelates*, 3 (1974).

Dunaway-Mariano, D. and Cleland, W.W., "Preparation and Properties of Chromium(III) Adenosine 5'Triphosphate, Chromium(III) Adenosine 5'-Diphosphate, and Related Chromium(III)-Complexes." *Biochemistry 19* 1496-1505 (1980).

Liu, Y. and Wu, C., "Radiolabeling of Monoclonal Antibodies with Metal Chelates," *Pure and Applied Chem. 63* 427-463(1991).

Krejcarek, G.E. and Tucker, K.L., "Covalent Attachment of Chelating Groups to Macromolecules," *Biochemical and Biophysical Research Communications 77*, 581-583 (1977).

Sundberg et al., "Selective Binding of Metal Ions to Macromolecules Using Bifunctional Analogs of EDTA." *J. Medicinal Chemistry 17* 1304-1307 (1974).

Dale, R.M.K. and Ward, D.C., "Direct Covalent Mercuration of Nucleotides and Polynucleotides," *Biochemistry 14* 2458-2469 (1975).

Jeng et al., "The Use of Aryl Azido ATP Analogs as Photo Affinity Labels for Nyosin ATPase," *J. Supramolecular Structure 3*: 448-468 (1975).

Gottikh et al., "The General Synthetic Route to Amino Acid Esters of Nucleotides and Nucleosides-5'-Triphosphates and Some Properties of These Compounds." *Tetrahedron 26*: 4419-4433 (1970).

*Biochemistry, Third Edition*, Stryer, L., Editor, pp. 96-97 W.H. Freeman and Co., New York (1988).

Karlson, Kurzes Lchrbuch der Bioehemie (1972) (short textbook of biochemistry), George Thieme publishers, Stuttgart, in particular pp. 169-170.

Scheit, Karl H., *Nucleotide Analogs: Synthesis and Biological Function*, John Wiley & Sons, Inc., New York, 1980, 288 pages.

Kornberg, A., *DNA Synthesis*, W. H. Freeman and Company, San Francisco, 1974, Chapter 7, pp. 227-228.

Kornberg, A., *DNA Replication*, W. H. Freeman and Company, San Francisco, 1980, Chapter 12, "Inhibitors of Replication," pp. 415-441.
Adams, R. L. P. et al., *Davidson's The Biochemistry of the Nucleic Acids*, 8th Edition, Academic Press, New York, 1976, Chapter 11 "Replication of DNA," pp. 298-299.
Langen, P., *Antimetabolites of Nucleic Acid Metabolism: The Biochemical Basis of Their Action, with Special Reference to their Application in Cancer Therapy*, Gordon and Breach, New York, English edition translated from the German by Dr. Thomas A. Scott, 1975, pp. 143-187.
Darlix at al., *Biochemistry 10*:1525-1531 (1971).
Geider, K., *European Journal of Biochemistry 27*:554-563 (1972).
Darlix and Fromageot, *Biochimie 56*:703-710 (1974).
Marcus, F., *Cancer Research 36*:1847 (1976).
Simoncsits and Tomasz, *Tetrahedron Letters 44*:3995-3998 (1976).
Chladek et al., *Biochemistry 16*:4312-4319 (1977).
Piperno and Alberts, *Journal of Biological Chemistry 253*:5174-5179 (1978).
Reha-Krantz et al., *Journal of Virology 67*:60-66 (1993).
Birch and Lee, *Journal of Food Science 41*:1403-1407 (1976).
Lartey and Derechin, *Preparative Biochemistry 9*:85-95 (1979).
Roberts and Hayes, *Scandinavian Journal of Dental Research 88*:801-909 (1980).
Kortnyk et al., *Eur. J. Med. Chem.—Chimica Therapeutica 15*:77-84 (1980).
Keppler et al., *Biochemical Journal 206*:139-146 (1982).
Yang and Metzler, *Methods in Enzymology 62*:528-551 (1979).
Stridh et al., *Archives of Virology 61*:245-250 (1979).
Stoeckler et al., *Biochemistry 19*:102-107 (1980).
Montgomery, J. H. and H. Jeanette Thomas, "4-Amino-7-β-D-Ribofuranosyl-7H-Imidazol[4,5-*d*]-v-Triazine(2-Aza-Adenosine) The Synthesis of 2-Azapurine Nucleosides from Purine Nucleosides Accomplished via Ring Opening Followed by Reclosure with Nitrous Acid," in *Nucleic Acid Chemistry: Improved and New Synthetic Procedures, Methods and Techniques*, Part Two, Dr. Leroy B. Townsend and Dr. R. Stuart Tipson, Editors, John Wiley & Sons, New York, 1978, No. 118, pp. 681-685.
Shibaev, V. N. and S. M. Spiridonova, "1-Methyladenosine-5'-(α- - Glucopyranosyl Pyrophosphate): Methylation of Adenosine Derivatives," in *Synthetic Procedures in Nucleic Acid Chemistry*, vol. I, Werner Zorbach and R. Stuart Tipson, Editors, Interscience Publishers, New York, 1968, No. 14, pp. 481-462.
Thomas, H. Jeanette and J. A. Montgomery, "3-Benzylpurines," in *Synthetic Procedures in Nucleic Acid Chemistry*, vol. I, Werner Zorbach and R. Stuart Tipson, Editors, Interscience Publishers, New York, 1988, No. 10, pp. 28-30.
Yamamoto at el., *J. Radiation Research 21*:239-247 (1980).
Rhaese, H. J., *Biochimica et Biophysics Acta 166*:31-326 (1968).
Taylor, M. R., *Acta Crystallogr. B29*:884-890 (1973).
Walker et al., *Australian Journal of Chemistry 26*:2391-2399 (1973).
Srinivasan et al., *J. Chemical Society D24*:1668-1669 (1970).
Kaneko et al., "8,2-Anhydrides of Purine -8-Thiol Nucleosides (or of Purine 2'-Thionucleosides): Synthesis of 8,2'-Anhydronucleosides of Purine-8-thiol [or of 8,2'-Anhydro-(2'-thionucleosides)] by use of Diphenyl Carbonate as the Cyclizing Agent," in *Nucleic Acid Chemistry: Improved and New Synthetic Procedures, Methods and Techniques*, Part Two, Dr. Leroy B. Townsend and Dr. R. Stuart Tipson, Editors, John Wiley & Sons, New York, 1978, No. 103, pp. 395-399.
Robins, M. J. and G. L. Bason, "6-Chloro-9-(2-Deoxy-β-D-Erythro-Pentofuranosyl)Purine from the Chlorination of 2'-Deoxyinosine: Direct Replacement of the 6-Oxo Group by a Chlorine Atom in a Purine 2'-Deoxynucleoside: Stabilization of the Glycosyl Bond Towards Cleavage by Acid," in *Nucleic Acid Chemistry: Imoroved and New Synthetic Procedures, Methods and Techniques*, Part Two, Dr. Leroy B. Townsend and Dr. R. Stuart Tipson, Editors, John Wiley & Sons, New York, 1978, No. 104, pp. 601-606.
Zemlicka, J. and J. Owens, "6-Chloro-9-β-D-Ribofuranosylpurine: A Versatile Intermediate in the Synthesis of Purine Ribonucleosides," in *Nucleic Acid Chemistry: Improved and New Synthetic Procedures, Methods and Techniques*, Part Two, Dr. Leroy B. Townsend and Dr. R. Stuart Tipson, Editors, John Wiley & Sons, New York, 1978, No. 106, pp. 611-614.
Kochetkov et al., "3-Methyluridine 5'-Phosphate: Methylation of Uridine Derivatives with Diazomethane: Phosphorylation of Nucleosides with Pyrophosphonyl Chloride," in *Synthetic Procedures in Nucleic Acid Chemistry*, vol. I, Werner Zorbach and R. Stuart Tipson, Editors, Interscience Publishers, New York, 1968, No. 152, pp. 497-499.
Zemlicka, J., "3-Methyl-6-Azauridine [4-Methyl-2-β-D-Riboluranosyl-AS-Triazin-3,5-(2H,4H)-Dione]: Alkylation of a Nucleoside Antimetabolite by Use of N,N-Dimethyl-formamide Dimethyl Acetal," in *Nucleic Acid Chemistry: Improved and New Synthetic Procedures, Methods and Techniques*, Part Two, Dr. Leroy B. Townsend and Dr. R. Stuart Tipson, Editors, John Wiley & Sons, New York, 1978, No. 78, pp. 451-453.
Piskala, A. and F. Sorm, "1-β-D-Ribofuranosyl-δ-Triazine-2,4-(1H,3H)-Dione (5-Azauridine): Direct Synthesis of a 5-Azauridine Ribonucleoside by the Fisher-Helferich Procedure," in *Nucleic Acid Chemistry: Improved and New Synthetic Procedures, Methods and Techniques*, Part Two, Dr. Leroy B. Townsend and Dr. R. Stuart Tipson, Editors, John Wiley & Sons, New York, 1978, No. 79, pp. 455-459.
Poverenny et al., *Molecular Immunology 16*:313-316 (1979).
Visser, D. W. and P. Roy-Burman, "5-Hydroxyuridine 5-Phosphate Derivatives: Substitution Reactions at the Pyrimidine Ring of Nucleotides," in *Synthetic Procedures in Nucleic Acid Chemistry*, vol. I, Werner Zorbach and R. Stuart Tipson, Editors, Interscience Publishers, New York, 1968, No. 151, pp. 493-496.
Cadet, J., "1-(2-Deoxy--β-D-Erythro-Pentopyranosyl)Uracil and Its α-D Anomer: Acid-Catalyzed Isomerization of the Glycosyl Group in 5,5-Dibromo-2'-deoxy-5,6-dihydro-6-hydroxyuridine," *Nucleic Acid Chemistry: Improved and New Synthetic Procedures, Methods and Techniques*, Part Two, Dr. Leroy B. Townsend and Dr. R. Stuart Tipson, Editors, John Wiley & Sons, New York, 1978, No. 55, pp. 311-315.
Kondo et al., *Makromol. Chem., Rapid Commun. 1*:303-306 (1980).
Nair et al., *Journal of Organic Chemistry 45*:3969-3974 (1980).
Fujii et al., *Chem. Pharm. Bull. 28*:3443-3446 (1980).
Hiraoka, K. and T. Yokoyama, *Int. J. Biolog. Macromolecules 1*:50-54 (1979).
Zeleznick, L. D., "6-Amino-9-(4-Dimethylaminobutyl)-9*H*-Purine," in *Nucleic Acid Chemistry: Improved and New Synthetic Procedures, Methods and Techniques*, Drs. Leroy B. Townsend and R. Stuart Tipson, Editors, John Wiley & Sons, Inc., 1978, pp. 17-18.
Watson, A. A., *Journal of Organic Chemistry 39*:2911-2916 (1974).
Helfer et al., *Journal of Organic Chemistry 46*:4803-4804 (1981).
Hosmane, R. S. and N. J. Leonard, *Synthesis 2*:118-119 (1981).
Hayashi et al., *Bull. Chem. Soc. Japan 53*:277-278 (1980).
Kondo et al., *Synthetic Communications 10*:267-271 (1980).
Pitha, J. and P. O. P. Ts'o, *Journal of Organic Chemistry 33*:1341-1344 (1968).
Inaki et al., "Synthesis of Poly-L-Lysine Containing Nucleic Acid Bases," in *Modification of Polymers*, Charles E. Carraher, Jr. and Minoru Tsuda, Editors, ACS Symposium Series 121, American Chemical Society, Washington, D.C., 1980, pp. 359-370.
Shimidzu et al., *Bulletin of the Chemical Society of Japan 52*:3362-3365 (1979).

\* cited by examiner

FIG. 3A  DNA BINDING TO CON A SEPHAROSE EFFECT ON MANNOSE

NUCLEIC ACID SEQUENCING PROCESSES USING NON-RADIOACTIVE DETECTABLE MODIFIED OR LABELED NUCLEOTIDES OR NUCLEOTIDE ANALOGS, AND OTHER PROCESSES FOR NUCLEIC ACID DETECTION AND CHROMOSOMAL CHARACTERIZATION USING SUCH NON-RADIOACTIVE DETECTABLE MODIFIED OR LABELED NUCLEOTIDES OR NUCLEOTIDE ANALOGS

REFERENCE TO OTHER RELATED APPLICATIONS

This application is a continuation of U.S. patent application Ser. No. 07/954,772, filed on Sep. 30, 1992, which application was abandoned in favor of the present application. Ser. No. 07/954,772 was a continuation of U.S. patent application Ser. No. 07/548,348, filed on Jul. 2, 1990 (abandoned), which was a divisional application of U.S. patent application Ser. No. 07/140,980, filed on Jan. 5, 1988 (abandoned), which was a continuation of U.S. patent application Ser. No. 06/674,352, filed on Nov. 21, 1984 (abandoned), the latter being a continuation of U.S. patent application Ser. No. 06/391,440, filed on Jun. 23, 1982 (abandoned). Two other applications were filed as divisional applications of the aforementioned Ser. No. 07/140,980: U.S. patent application Ser. No. 07/532,704, filed on Jun. 4, 1990; and U.S. patent application Ser. No. 07/567,039, filed on Aug. 13, 1990. Ser. No. 07/532,704 issued on Aug. 31, 1993 as Engelhardt et al., U.S. Pat. No. 5,241,060, and is titled "Base Moiety-Labeled Detectable Nucleotide." Ser. No. 07/567,039 issued on Nov. 9, 1993 as Engelhardt et al., U.S. Pat. No. 5,260,433, and is titled "Saccharide Specific Binding System Labeled Nucleotides.

BACKGROUND OF THE INVENTION

It is known to produce nucleotides or polynucleotides which are radioactively labeled, such as with isotopes or hydrogen ($^3$H), phosphorus ($^{32}$P), carbon ($^{14}$C) or iodine ($^{125}$I). Such radioactively labeled compounds are useful to detect, monitor, localize and isolate nucleic acids and other molecules of scientific or clinical interest. Unfortunately, however, the use of radio-actively labeled materials presents hazards due to radiation. Also due to the relatively short half life of the radioactive materials employed to label such compounds or materials, the resulting labeled compounds or materials have a corresponding relatively short shelf life.

It has been proposed to chemically label compounds of interest, such as nucleotides and polynucleotides, so as to overcome or avoid the hazards and difficulties associated with such compounds or materials when radioactively labeled. In the article by P. R. Langer, A. A. Waldrop and D. C. Ward entitled "Enzymatic Synthesis of Biotin-Labeled Polynucleotides: Novel Nucleic Acid Affinity Probes", in *Proc. Natl. Acad. Sci., USA, Vol.* 78, No. 11, pp. 6633-6637, November, 1981, there are described analogs of dUTP and UTP that contain a biotin molecule bound to the C-5 position of the pyrimidine ring through an alkylamine linker arm. The biotin-labeled nucleotides are efficient substrates for a variety of DNA and RNA polymerases in vitro. Polynucleotides containing low levels of biotin substitution (50 molecules or fewer per kilobase) have denaturation, reassociation and hybridization characteristics similar to those of unsubstituted controls. Biotin-labeled polynucleotides, both single and double stranded, are selectively and quantitatively retained on avidin-Sepharose, even after extensive washing with 8M urea, 6M guanidine hydrochloride or 99% formamide. In addition, biotin-labeled nucleotides can be selectively immunoprecipitated in the presence of antibiotin antibody and *Staphylococcus aureus*, Protein A. These unique features of biotin-labeled polynucleotides suggest that they are useful affinity probes for the detection and isolation of specific DNA and RNA sequences. It is indicated in the article that the subject matter of the article is comprised in a pending U.S. patent application.

The disclosures of this article and above-referred pending patent application are herein, incorporated and made part of this disclosure.

The patent application referred to in the above-identified article is U.S. patent application Ser. No. 255,223 filed Apr. 17, 1981. Ser. No. 06/255,223 was abandoned in favor of continuation application, U.S. patent application Ser. No. 06/496,915, filed on May 23, 1983, now U.S. Pat. No. 4,711,955. A related divisional application of the aforementioned Ser. No. 06/496,915 was filed as U.S. patent application Ser. No. 07/130,070 (on Dec. 8, 1987), and has since issued on Jul. 12, 1994 as U.S. Pat. No. 5,328,824. Two related continuation applications of the aforementioned Ser. No. 07/130,070 were filed on Feb. 26, 1992 (as Ser. No. 07/841,910) and on May 20, 1992 as (Ser. No. 07/886,660). In the above-identified pending U.S. patent application the subject matter of the above-identified article is disclosed and additionally it is disclosed that compounds having the structure:

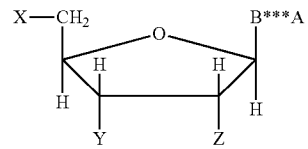

wherein B represents a purine, deazapurine, or pyrimidine moiety covalently bonded to the $C^1$-position of the sugar moiety, provided that when B is purine or 7-deazapurine, it is attached at the $N^9$-position of the purine or deazapurine, and when B is pyrimidine, it is attached at the $N^1$-position;

wherein A represents a moiety consisting of at least three carbon atoms which is capable of forming a detectable complex with a polypeptide when the compound is incorporated into a double-stranded ribonucleic acid, deoxyribonucleic acid duplex, or DNA-RNA hybrid;

wherein the dotted line represents a chemical linkage joining B and A, provided that if B is purine the linkage is attached to the 8-position of the purine, if B is 7-deaza-purine, the linkage is attached to the 7-position of the deazapurine, and if B is pyrimidine, the linkage is attached to the 5-position of the pyrimidine; and wherein each of x, y, and z represents

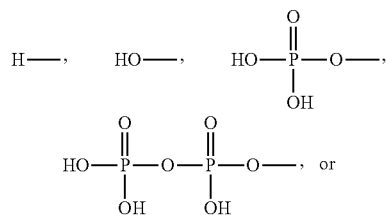

-continued

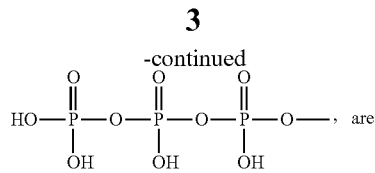, are widely useful as probes in biomedical research and recombinant DNA technology.

Particularly useful are compounds encompassed within this structure which additionally have one or more of the following characteristics: A is non-aromatic; A is at least $C_5$; the chemical linkage joining B and A includes an α-olefinic bond; A is biotin or iminobiotin; and B is a pyrimidine or 7-deazapurine.

The publications cited in the aforementioned U.S. Pat. No. 4,711,955 are also herein incorporated and made part of this disclosure.

SUMMARY OF THE INVENTION

In accordance with the practices of this invention nucleotides are modified, such as at the 5 position of pyrimidine or the 7 position of purine, preparatory for the preparation therefrom of nucleotide probes suitable for attachment to or incorporation into DNA or other nucleic acid material. In the practices of this invention nucleotides, i.e. nucleic acids, preferably are modified in a non-disruptive manner such that the resulting modified nucleotides are capable of incorporation into nucleic acids and once incorporated in nucleic acids the modified nucleotides do not significantly interfere with the formation or stabilization of the double helix formed of the resulting nucleic acids containing the modified nucleotides. The non-disruptive modification of nucleotides and nucleic acids incorporating such modified nucleotides is in contrast with those modifications of nucleotides which are characterized as a disruptive modification in the sense that the resulting disruptively modified nucleotides and nucleic acids containing the same, block proper double helix formation. In the practices of this invention, the nucleotides are desirably modified at the 5 position of the pyrimidine or the 7 position of the purine. The nucleotides so modified are non-disruptively modified and nucleic acids containing such nucleotides are capable of forming a double helix arrangement.

Broadly, in another aspect of the practices of this invention various methods are useful for the tagging or labeling of DNA in a non-disruptive manner. For example, biotin is added on the end of a DNA. or RNA molecule. The addition of biotin is accomplished by addition of a ribonucleotide. The 3',4' vicinal hydroxyl groups are oxidized by periodate oxidation and then reduced by a borohydride in the presence of biotin hydrazide. Alternatively, carbodiimide can also be used to couple biotin to the aldehyde group.

Another technique for tagging nucleic acid material such as DNA or RNA involves the addition of a large marker to the end of a DNA or RNA molecule. One example of this technique is the addition of a molecule, e.g. lysylglycine, where the amino groups are tagged with biotin. Another example would be to follow the procedure set forth hereinabove but employing carbodiimide as the cross-linking agent. Still another example of this technique would be to produce a biotinylated dA:dU double helical polymer and to ligate this polymer to the probe prepared in accordance with this invention.

Another technique for tagging DNA in a non-disruptive manner involves the isolation of dPyrTP having a putricine or spermidine on the 5 position from PS16 or phage-infected cells. If desired, dPyrTP is made from phage DNA and phosphorylated to dPyrTP followed by modification of the polyamine side chain by means of standard nucleophilic reagent NHS-biotin.

Another technique for tagging DNA in a non-disruptive manner involves the addition of glucose to 5-hydroxy-methylcytosine (5 HMC) in DNA using T4 phage glycoslyating enzymes followed by screening by means of a lectin-based assay.

Still another method for tagging DNA in a non-disruptive manner involves 5-HMC-triphosphate made from the hydrolysis of T4-DNA followed by phosphorylation of the 5HMCMP to 5 HMCTP. 5HMCTP is then incorporated into DNA using polymerase I. Thus, any DNA can be modified to have non-disruptively incorporated therein 5 HMC.

A method for tagging DNA in a mildly disruptive manner involves reacting nucleic acids in the double helical form with alkylating reagents as for example benz(o)pyrene diol epoxide or aflatoxin. Under appropriate conditions the $N^2$ group of guanine, the $N^4$ group of adenosine or the $N^4$ group of cytosine are alkylated. These modified nucleotides can be directly detected with antibodies or can be used as linking arms for the addition of a reporter molecule such as biotin.

BRIEF DESCRIPTION OF THE DRAWINGS

FIG. 3A is a graph that illustrates the recovery (measured as a percent) of tritium labeled T4 DNA using a Con A-sepharose column when mannose is included in the buffer, as described in Example XXII.

Figure 1:
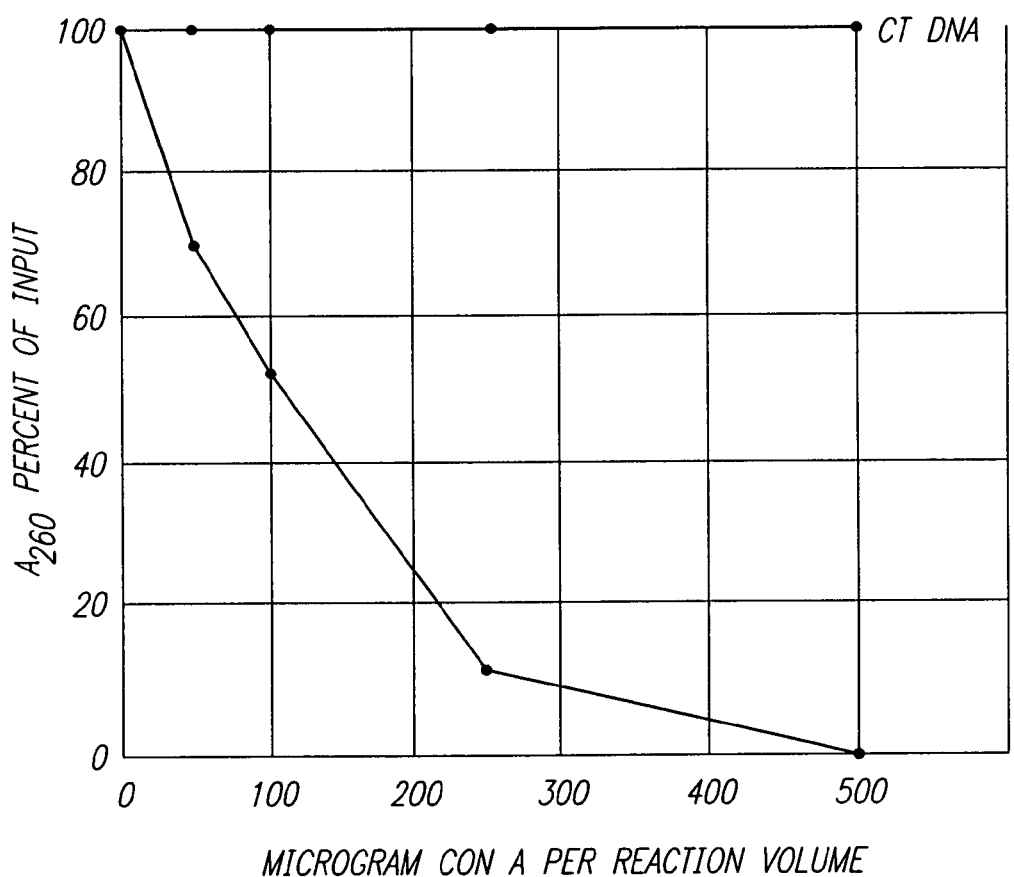
FIG. 1 is a graph that shows the results of a precipitation reaction of glucosylated DNA as described in Example XXI. Absorbance was measured at 260 nanometers for the reaction mixtures and control solutions.

The following examples are illustrative of various embodiments of the practices of this invention:

EXAMPLE I

Biotinyl-N-hydroxysuccinide ester (BNHS) was prepared according to a method of Becker et al. P.N.A.S. 68 2604 (1971). Biotin (0.24 g, 1.0 mmol) was dissolved in 5 ml dry dimethylformamide. Dicyclohexylcarbodimide (0.21 g, 1.0 mmol) and N-hydroxysuccinimide (0.12 g, 1.0 mmol) were added and the solution stirred at room temperature for 15 hours. After filtration of the subsequent precipitate, the filtrate was evaporated at reduced pressure the residue was washed twice with ethanol and recovered from hot isopropyl alcohol to yield a white crystalline product having a m.p. of 216-218° C.

EXAMPLE II

Biotinyl-1,6-diaminohexane amide was prepared as follows: A solution of 1,6-diaminohexane (320 mg, 2.0 mmol), dissolved in 50 ml water, was brought to pH 8.5 by addition of carbon dioxide. Biotinyl-N-hydroxy-succinimide ester (100 mg, 0.29 mmol), dissolved in 10 ml dimethylformamide, was added. After 18 hours at room temperature the mixture was evaporated and the residue washed with ether and subsequently dried in a dessicator.

EXAMPLE III

Polybiotinylated poly-L-lysine was prepared by the following procedure. Polylysine (100 umol lysine) dissolved in 2 ml 0.1 M sodium borate, pH 8.5 was added to biotinyl-N-hydroxysuccimide ester (17.5 mg, 50 umol) dissolved in 0.5 ml dimethylformamide. After stirring at room temperature for 18 hours, the mixture was dialyzed against 10 mM tris buffer, pH 7.5.

EXAMPLE IV

Oligodeoxyribonucleotides were end-labeled using cytidine-5'-triphosphate and terminal transferase as follows. Purified phage DNA, alkali sheared with 0.2 N sodium hydroxide and diluted to 2 $A_{260}$ units/ml in potassium cacodylate (0.1 M), tris base (25 mM), cobalt chloride (1 mM) and dithiothreitol (0.2 M) were used. To this DNA solution (1 ml) was added cytidine-5'-triphosphate (10 mmol) and terminal transferase (200 units).

After incubating at 37° C. for 5 to 8 hours the reaction was stopped by the addition of neutralized phenol (100 ul), 0.5 M EDTA (100 ul) and 1% sodium dodecyl sulfate (100 ul). The DNA was purified by gel filtration chromatography through Sephadex® G-100 followed by precipitation with ethanol.

EXAMPLE V

Biotin and polybiotinylated poly-L-lysine were coupled to oligoribonucleotides using a carbodimide coupling procedure described by Halloran and Parker, *J. Immunol.*, 96 373 (1966). As an example, DNA (1 ug/ml), 1 ml) in tris buffer pH 8.2, sheared with 0.1 N sodium hydroxide was denatured by boiling for 10 minutes and quick cooling in an ice bath. Biotinyl-1,6-diaminohexane amide (2 mg, 6 umol) or polybiotinylated poly-L-lysine (2 mg) and 1-ethyl-3-diisopropylaminocarbodiimide HCl (10 mg, 64 umol) were added, and the pH readjusted to 8.2. After 24 hours at room temperature in the dark, the mixture was dialyzed against 10 mM tris buffered saline. DNA was precipitated ethanol.

EXAMPLE VI

Biotin, conjugated to cytochrome C, was prepared by the following procedure. To a solution of cytochrome C (10 mg) in 1 ml of 0.1 M sodium borate, pH 8.5 was added biotinyl-N-hydroxysuccinimide ester (10 mg, 29 umol) in 1 ml dimethyl formamide. After 4 hours at room temperature, the biotinylated protein was purified by gel filtration chromatography through a Sephadex® G-50 column.

EXAMPLE VII

Formaldehyde coupling of cytochrome C-biotin and polybiotinylated poly-L-lysine to oligodeoxyribonucleotides were carried out using a method similar to that described by Manning et al, *Chromosoma,* 53, 107 (1975). Oligodeoxyribonucleotide fragments obtained by sodium hydroxide shearing of purified DNA (100 ug/ml in 10 mM triethanolamine, pH 7.8 were denatured by boiling for 10 minutes followed by quick cooling in ice. Cytochrome C-biotin 0.05 g ml or polybiotinylated poly-L-lysine solution (0.05 ml) dissolved 3 mg/ml in 10 mM triethanolamine, pH 7.8 was added to 1 ml at the denatured oligodeoxyribonucleotide solution along with 0.1 ml of 6% formaldehyde in 10 mM triethanolamine, pH 7.8. After stirring at 40° for 30 minutes the mixture was dialyzed against the same buffer. The oligodeoxyribonucleotide-biotin complex was finally purified by gel filtration chromatography on Sephadex G-100 followed by precipitation from ethanol.

EXAMPLE VIII

Double stranded polydeoxyadenylic acid:polybiotinylated deoxyuridylic acid was synthesized as follows. The double stranded oligonucleotide polydeoxyadenylic acid:polythymidylic acid (20 ug) of length 300 basic pairs, dissolved in 200 ul exonuclease III buffer consisting of Tris-HCl pH 8.0 (70 mM); magnesium chloride (1.0 mM) and dithiothreitol (10 mM) was incubated with 100 units exonuclease III for 20 minutes at 20° C. The partially digested oligonucleotide was immediately extracted with phenol, and the DNA was precipitated with 70% aqueous ethanol. The partially digested oligonucleotide was redissolved in 20 ul 5 mM tris-HCl pH 7.6 and incubated at 20° C. for 2 hours in a reaction containing 2'-deoxy-adenosine-5'-triphosphate (15 uM) thymidine-5'-triphosphate (the amount determines the degree of substitution) and biotinylated 5-(3-amino-1-propene) 2'-deoxyuridine-5'-triphosphate (5 uM), Klenow DNA polymerase I (200 units) dissolved in 0.1 mM) potassium phosphate, pH 8.0 at a concentration of 0.2 units/ul. The biotinylated poly dA:poly dT, biotinyl dU was purified by gel filtration chromatography on Sephadex® G-100. The DNA was enthanol precipitated and redissolved in 20 ul of solution containing sodium acetate pH 4.6 (30 mM), sodium chloride (50 mM), zinc sulfate (1 mM) and glycerol (5%). $S_1$ nuclease (200 units) was added, and the reaction was incubated at 37° for 10 minutes. The reaction was stopped with 1 ml ammonium acetate (4 M) and 6 ml ethanol. The DNA was repurified by G-100 gel filtration chromatography and ethanol precipitation.

EXAMPLE IX

Ligation of poly dA:poly dT, biotinyl dU to oligodeoxyribonucleotides was accomplished as follows: DNA fragments from alkali sheared purified DNA (as described in Example VIII) were digested with $S_1$ nuclease and repurified by phenol extraction and ethanol precipitation. Blunt ended DNA fragments (1 ug) and poly dA:poly dT, biotinyl dU (2 ug) were dissolved in 6 ul at a buffer containing tris-HCl pH 7.4 (66 mM), magnesium chloride (6.6 mM), adenosine triphosphate (24 mM) and dithiothreitol (1.0 mM), $T_4$ DNA ligase (50 units) was added, and the volume brought to 20 ul with water. The reaction was incubated 3 hours at 37° C. The DNA was purified by gel filtration chromatography through Sephadex® G-100 and was ethanol precipitated.

EXAMPLE X

5-Hydroxymethyl-2'-deoxycytidylic acid was prepared by enzymatic hydrolysis of non glycosylated phage $T_4$ DNA. Purified phage DNA (2 mg), dissolved in 1 ml 50 mM tris pH 7.4 and 10 mM magnesium chloride, was incubated 20 hours with deoxyribonuclease I at 37°. The pH was adjusted to 9.0 and sodium chloride (20 mM) added. Snake venom phosphodiesterase (0.05 g units in 0.5 ml water) was added and incubation continued at 37° for 5 hours. An additional 0.05 units phosphodiesterase was added and incubation continued 18 hours. Nucleotides were separated by gel filtration chromatography through Sephadex® G-50. 5-hydroxymethyl-2'-deoxycytidylic acid was purified by reverse phase high pressure liquid chromatography.

EXAMPLE XI 5-(4-aminobutylaminomethyl)-2'-deoxyuridylic acid was obtained by enzymatic hydrolysis of DNA from phage ØW-14. The phage was grown on *Pseudomonas acidovorans* 29 according to Kropinski and Warren, *Gen. Virol.* 6, 85 (1970), and the phage DNA purified according to Kropinski et al, *Biochem.* 12, 151 (1973). The DNA was enzymatically hydrolyzed with deoxyribonuclease I and snake venom phosphodiesterase using the procedure described elsewhere (Example X). 5-(4-aminobutylamino-methyl)-2'-deoxyuiidylic acid was purified by reverse phase high-pressure liquid chromatography.

EXAMPLE XII

Biotinylated-5-(4-aminobutylaminomethyl)-2'-deoxyuridylic acid was prepared as follows: Biotinyl-n-hydroxysuccinimide ester (70 mg 0.2 mmol) dissolved in 1 ml dimethylformamide was added to 5-(4-aminobutylaminomethyl)-2'-deoxyuridylic acid in 20 ml 0.1 M sodium borate pH 8.5. After 4 hours the solution was concentrated to 0.5 ml by evaporation, and the biotinylated nucleotide was purified by reverse phase high pressure liquid chromatography.

EXAMPLE XIII 5-formyl-2'-deoxyuridine prepared according to Mertes and Shipchandler, *J. Heterocyclic Chem.* 1, 751 (1970). 5-hydroxymethyluricil (1 mmol) dissolved in 20 ml dimethylsulfonate was heated at 100° C. with manganese dioxide (2.5 mmol) for 15 minutes. The solvent was evaporated at reduced pressure. The residue was taken up in hot ethanol and recrystallized from ethanol to yield 5-formyluracil, 5-formyluracil (0.10 g) was silylated and dissolved in dry acetonitrile (2.5 ml). 2-deoxy-3,5-di-O-p-toluoyl-D-ribofuranosyl chloride (Bhat, *Syn. Proc. in Nucleic Acid Chem.*, Vol. I, p. 521 (1968) (0.22 g) and molecular sieves (0.2 g) were added, and the mixture stirred at 25° C. for 40 hours under anhydrous conditions. The mixture was filtered and evaporated. The resulting oil was treated with anhydrous ethanol (2 ml) and chromatographed on silica gel to obtain the partially pure anomer which was recrystallized from ethanol (M.P. 195-196° C.) The toluoyl groups were removed by reaction of the product in methanol benzene, with sodium methoxide. The mixture was neutralized with Dowex 50 ($H^+$). 5-formyl-2'-deoxyuridine was recrystallized from ethanol M.P. 175-176° C.

EXAMPLE XIV

Biotin was coupled to 5-formyl-2'-deoxyuridine as follows: To 5-formyl-2'-deoxyuridine (0.320 g, 1.0 mmol) dissolved in 300 ml 0.05 M sodium borate, was added biotinyl-1,6-diaminohexane amide (0.74 g, 2 mmol). After stirring one hour, sodium borohydride (0.2 g, 5 mmol) was added and stirring continued for an additional 4 hours followed by the addition of 8 ml 1M formic acid. The biotinated compound was purified by reverse phage HPLC eluting with methanol: 0.5 M triethyl ammonium acetate, pH 4.0.

EXAMPLE XV

Biotin was coupled to 5-amino-2'-deoxyuridine as follows: 5-amino-2'-deoxyuridine (0.24 g, 1 mmol), biotin (0.25 g, 1 mmol) and dicyclohexylcarbodiimide (0.21 g, 1 mmol) were dissolved in dry dimethyl formamide and stirred at room temperature overnight. After filtration and evaporation of the solvent, the residue was washed with ether. The biotin-coupled product was purified by reverse phase high pressure liquid chromotography using a water methanol gradient.

EXAMPLE XVI 5-(oxy)acetic acid-2'-deoxyuridine was prepared according to a procedure of Deschamps and DeClerq, *J. Med. Chem.*, 21, 228 (1978). 5-hydroxy-2-deoxyuridine (282 mg, 1.15 mmol) was dissolved in 1.16 ml, 1N potassium hydroxide (1.16 mmol) after which iodoacetic acid (603 mg, 3.4 mmol) in 1 ml water was added. After reaction at room temperature for 48 hours 1N HCl (1.06 ml) was added. Concentration of this solution and addition of ethanol yielded a precipitate which was filtered, washed with cold ethanol and recrystallized from hot ethanol.

EXAMPLE XVII

Biotinyl-1,6-diaminohexane amide was coupled to 5-(oxy) acetic acid-2'-deoxyuridine as follows: Biotinyl-1,5-diaminohexane amide (0.74 g, 0.2 mmol), 5-(oxy)acetic acid-2'-deoxyuridine (0.60 g, 0.2 mmol) and dicyclohexylcarboimide (0.41 g, 0.2 mmol) were dissolved in 5 ml dry dimethylformamide and remained overnight at room temperature. The reaction was subsequently filtered and the solvent removed by evaporation. The residue was washed with 0.1N HCl and ether. The biotinated uridine derivative was purified by reverse phase high pressure liquid chromatography using a water-methanol gradient.

EXAMPLE XVIII

Phosphorylation of 5-substituted pyrimidine nucleosides was accomplished by the general procedure described below for biotinated-5-(oxy)acetic acid-2'-deoxyuridine. The nucleoside (0.16 g, 0.5 mmol) was dried by repeated evaporation from dry pyridine and redissolved in 10 ml dry pyridine. Monomethoxytrityl chloride (0.30 g, 0.8 mmol) was added and the mixture stirred at room temperature in the dark for 18 hours. The solution was diluted with chloroform (200 ml) and extracted with 0.1 M sodium bicarbonate. The organic layer was dried and evaporated. The tritylated nucleoside was redissolved in dry pyridine (20 ml) and acetylated by reaction at room temperature with acetic anhydride (0.1 ml, 20 mmol). The mixture was cooled to 4° C. and methanol (40 ml) added. After stirring 10 hours at room temperature, the reaction was concentrated by evaporation. The compound was detritylated by dissolving in 1% benzene sulfonic acid in chloroform (20 ml). After evaporation of solvent the nucleoside was purified by chromatography on silica gel eluting with 2% methanol:chloroform. The 3'-acetylated nucleoside was dried by repeated evaporation of dry pyridine. A mixture of phosphorous oxychloride (100 ul, 1 mmol), (1-H), 1,2,4-triazoic (140 mg, 2.2 mmol) and triethylamine (260 ul, 2.0 mmol) was stirred in 5 ml anhydrous dioxane at 10°-15° C. for 30 minutes and at room temperature for 1 hour. This was added to the 3'-acetylated nucleoside, and the mixture stirred at room temperature for 1 hour after which it was cooled to 0° C. Water (5 ml) was added and the reaction stirred at room temperature for 18 hours. Barium chloride (100 mg, 5 mmol) was added and the barium salt of the nucleotide collected by filtration. The salt was washed with water and ether. The barium salt was converted to the sodium salt by stirring with Dowex 50 ($Na^+$ form) in 10 ml water for 4 hours at room temperature. 2 N sodium hydroxide (2N, 10 ml) was added and the reaction stirred for 15 minutes at room temperature after which it was neutralized by addition of excess Dowex 50 (H$^+$) form. The deacetylated nucleotide was concentrated by evaporation and purified by reverse phase high-pressure chromatography.

EXAMPLE XIX 5-substituted pyrimidine triphosphates were chemically prepared from their respective 5' monophosphates using a procedure of Michelson, *Biochem Biophys Acta,* 91, 1, (1964). The example of 5-hydroxymethyl-2'-deoxycytidine-5'-triphosphate will be given. The others were similarly prepared. 5-hydroxymethyl-2' deoxycytidylic acid (free acid) (0.63 g, 0.2 mmol) was converted to its tri-n-octylammonium salt by suspending in methanol and addition of tri-n-octylammonium hydroxide (0.74 g, 0.2 mmol). The suspension was refluxed until a clear solution was obtained and the solvent removed under vacuum. The salt was dried by dissolution in and subsequent evaporation from dry pyridine several times. To the salt, dissolved in dry dimethylformamide (0.1 ml) and dioxane (1 ml) was added diphenylphosphochloridate (0.1 ml) and tri-n-butylamine (0.2 ml). After 25 hours at room temperature, solvent was removed and ether was added to precipitate the nucleoside-5'-diphenylpyrophosphate. This was dissolved in dioxane (0.5 ml) and a solution of di(tri-n-butylammonium) pyrophosphate (0.5 mmol) in 1 ml pyridine was added. After 45 minutes at room temperature, the mixture was concentrated under vacuum to a small volume. The crude product was precipitated with ether. This was dissolved in 0.1 M phosphate buffer pH 8.0. The trisphosphate was purified by chromatography on DEAE cellulose eluting with a gradient of 0.1 to 0.6 M triethylammonium bicarbonate ph 7.5.

EXAMPLE XX

DNA was labeled with 5-substituted pyrimidine triphosphates by nick translating DNA in the presence of the appropriate triphosphate. An example follows for labeling purified DNA with biotinylated 5-formyl-2'-deoxyuridine. DNA (20 ug/ml) was incubated at 14° C. in the presence of magnesium chloride (5 mM) 2'-deoxycytidine-5'-triphosphate (15 mM), 2' deoxyadenosine-5'-triphosphate (15 uM), 2'-deoxyguanosine-5'-triphsophate (15 uM), biotinylated-5-formyl-2'-deoxyuridine-5'-triphosphase (20 uM), activated pancreatic deoxyribonuclease I (13 mg/ml), *E. coli* deoxyribonuclease acid, polymerase I (40 units/ml) and tris HCL, pH 7.4 (50 mM). After 2 hours the reaction was stopped by addition of 0.3 M EDTA (0.05 ml) followed by heating at 65° for 5 minutes. Labeled oligonucleotide was purified by gel filtration chromatography through Sephadex® G-100 and precipitation from cold ethanol.

EXAMPLE XXI

Precipitation of Glucosylated DNA by Concanavalin A

Reaction mixtures (1.0 ml) were prepared in 1.5 ml eppendorf tubes as follows:

| | |
|---|---|
| Sodium potassium phosphate, pH 6.5 | 10 mM |
| NaCl | 150 mM |
| MgSO$_4$ | 5 mM |
| CaCl$_2$ | 1 mM |
| DNA (T4 of calf thymus) | 50 ug |
| Cancanavalin A (10 mg/ml) | 50-500 ug |

Reactions were started by the addition of concanavalin A (Con A). The solutions were mixed and left at room temperature for 60 minutes. The tubes were centrifuged at 1200 g for 15-20 minutes. The supernatants were diluted and the A$_{260}$ was measured.

Since Con A absorbs at 260 nanometers, control solutions lacking DNA but containing Con A were prepared. The Con A absorbance was subtracted from the absorbence obtained in the complete reaction mixtures.

The results of this reaction are presented in accompanying FIG. 1.

EXAMPLE XXII

Binding of Glucosylated DNA to Concanavalin A

Phage T4 DNA and phage lambda DNA were labeled by incorporation of H$^3$-deoxyadenosine triphosphate into the DNA by nick translation according to the Rigby et al procedure. T4 DNA was nick translated to a specific activity of 5×10$^5$ cpm/microgram and an average double-standed size of 5 kilobases. Lambda DNA was nick translation to a specific activity of 3×10$^5$ cpm/microgram and an average double stranded size of 6.0 kilobases as determined by agarose gel electrophoresis. Unincorporated nucleotides were removed from the reaction mixtures by Bio-Gel P-60 chromatography.

Con A sepharose was prepared as described by the manufacturer (Pharmacia). One ml of settled gel contained 18 mg of bound Con A. One ml columns were prepared in sterile pasteur pippetes and were equilibrated with PBS (0.15 M NaCl; 0.01 M sodium potassium phosphate, pH 6.5).

H$^3$-DNA samples, were prepared in 0.5 ml of buffer (as described in Example XXI but without Con A). T4 DNA solutions contained 176,000 cpm/0.5 ml, and lambda DNA solutions contained 108,000 cp./0.5 ml. A 0.5 ml sample was applied to the column.

A 10.5 ml volume of buffer was passed through the column, and the eluate fractions (0.33 m) were collected and counted in a Beckman LSC-100 scintillation counter in a 3.5 ml reafluor cocktail (Beckman). The results (FIGS. 2A and 2B) show that non-glucosylated DNA was not bound whereas glucosylated T4 DNA was bound to the column. The bound T4 DNA was removed by washing the column with a higher pH buffer (Tris-HCl, pH 7.2-8.2).

Figure 3B:
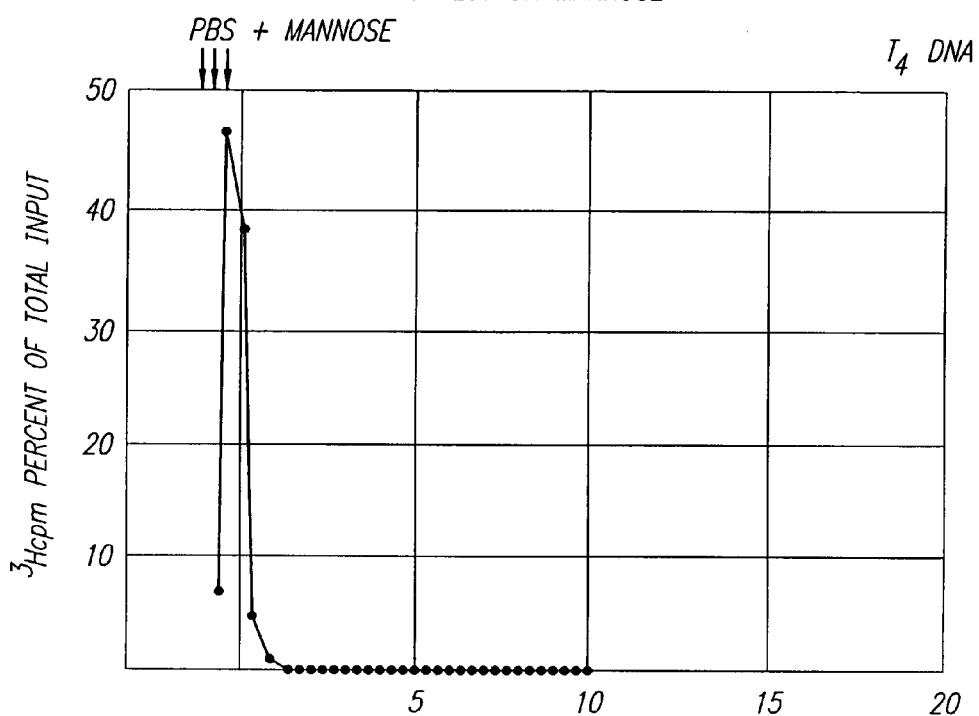
FIG. 3B is a graph that illustrates the recovery (measured as a percent) of tritium labeled T4 DNA using a Con A-sepharose column when mannose is included in the buffer, as described in Example XXII.
Figure 3B:
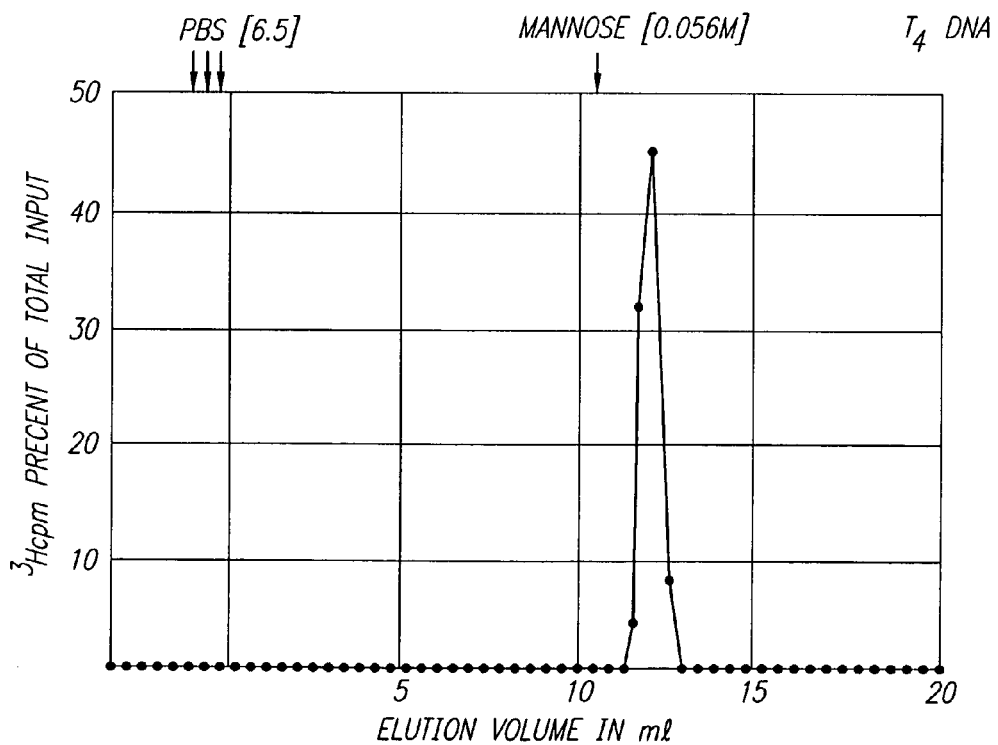

Furthermore, consistent with the interaction of glucose and Con A, mannose, when included in the buffer in which the DNA is applied to the column, prevents binding of glucosylated DNA to Con A sepharose. Also, mannose-containing buffer (PBS-containing 0.056 M mannose) removes bound T4 DNA from Con A sepharose (FIGS. 3A and 3B).

Further illustrative of the practices of this invention directed to nonradioactive methods or techniques of assaying for specific nucleic acids, the following example deals with the use of the sugar-lectin system. This example deals with the use of DNA which is not glycosylated in nature but rather has had a maltotriose group added thereto by way of nick translation described herein. The maltotriose modified dUTP and DNA modified therewith bind specifically to a column of concanvalin A covalently bound to sepharose. By this technique and in accordance with the practices of this invention, there is provided a means for specifically labeling any nucleic acid with sugars. As previously indicated herein, nick translation is only one of a number of techniques and approaches possible for the production of the modified nucleic acids in accordance with this invention.

EXAMPLE XXIII

Lambda DNA was nick translated as described herein with maltotriose coupled to 5-(3-amino-1-propenyl)-2'-deoxy-uridine-5' triphosphate and $^3$H-2'-deoxyadenosine-5'-triphosphate. Under these conditions DNA was substituted to 40 percent of its thymidine residues with the maltotriose nucleotide and had a specific activity of $8\times10^5$ counts per minute (cpm) per microgram of DNA. A control sample of DNA substituted only with $^3$H-dATP had a specific activity of $6\times10^5$ cpm per microgram DNA. The nick translated DNA samples were purified free of reaction mixture components by Biogel P-60 chromatography as described herein.

Figure 2A:
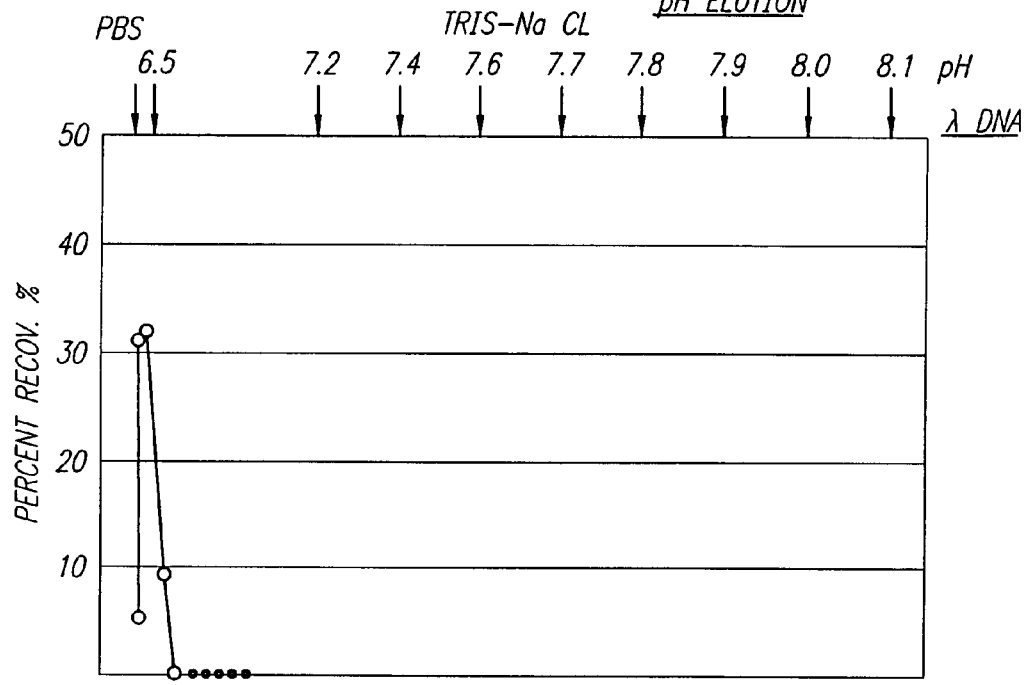
FIG. 2A is a graph that shows the recovery (measured as a percent) of tritium-labeled lambda DNA using a Con A-sepharose column as described in Example XXII. Non-glucosylated DNA was not bound whereas glucosylated DNA was bound to the column.
Figure 2B:
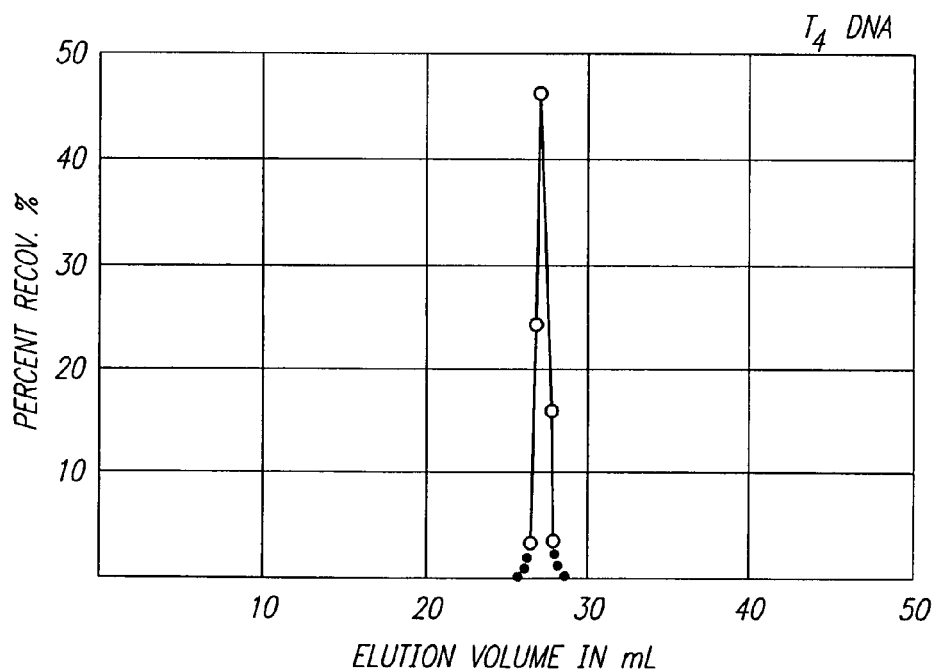
FIG. 2B is a graph that shows the recovery (measured as a percent) of tritium-labeled T4 DNA using a Con A-sepharose column as described in Example XXII. Non-glucosylated DNA was not bound whereas glucosylated DNA was column bound.
Figure 4A:
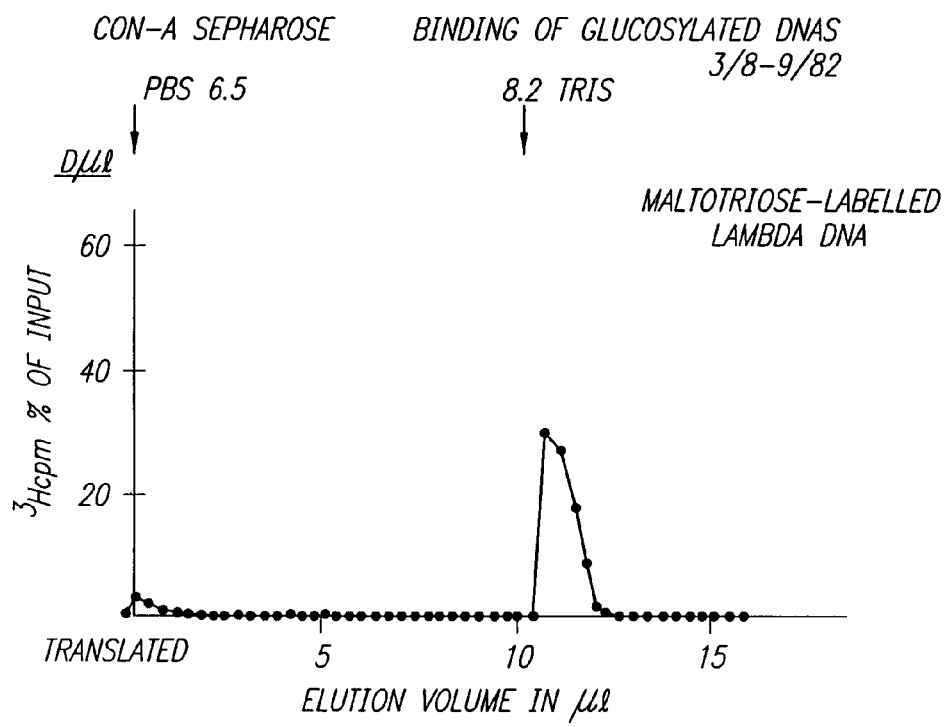
FIG. 4A is a graph that shows the retention of maltotriose labeled lambda DNA using a Con A-sepharose column as described in Example XXIII.
Figure 4B:
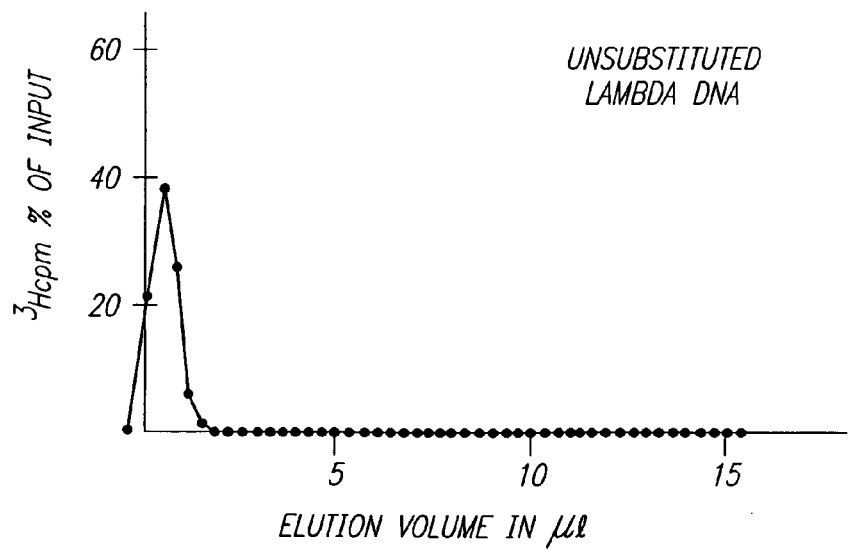
FIG. 4B is also a graph that shows the retention of unsubstituted tritiated lambda DNA using a Con A-sepharose column as described in Example XXIII.

The purified samples were applied to Con A-sepharose columns as described in FIGS. 2A and 2B. The maltotriose-labeled DNA was retained on the column when washed with PBS but was removed by subsequent elution with 10 mM Tris-HCl, pH 8.2 (FIG. 4A). The unsubstituted tritiated DNA did not bind to the column at pH 7.4 (FIG. 4B).

EXAMPLE XXIV

Potentially immunogenic heptenes may be introduced at the 5 position of uridine by a variety of methods in the literature. 5-(perfluorobutyl)-2'-deoxyuridine was synthesized using a method of Cech et al, *Nucl. Acids Res.* 2, 2183 (1979). Copper-bronze was prepared by reacting copper sulfite (5 g, 20 mmol) with zinc powder (2 g) in 20 ml water. The mixture was decanted, and the residue washed with water and then 5% hydrochloric acid and water. Just before use, the solid (2 g) was activated with 2% iodine in acetone (20 ml). After filtration the residue was washed with acetone:concentrated hydrochloric acid and then pure acetone. Activated copper-bronze (130 mg, 2 mmol) and 1-iodo-1',2,2',3,3',4,4' heptafluorobutane (1.3 mg, 4 mmol) were stirred in 3 ml dimethylsulfoxide at 110° C. for 1 hour. After cooling and filtration, 2'-deoxyuridine (245 mg, 1 mmol) was added, and the mixture heated at 110° C. for 1 hour. Water (5 ml) was added, and the mixture extracted with ether. The ether extracts were dried and evaporated under reduced pressure. The residue was chromatographed on a silica gel column eluting with ethylacetate.

EXAMPLE XXV

Tubericydin was substituted at the 5 position by derivitizing the 5-cyano compound, toyocamycin. An example is the synthesis of 4-amino-5 (tetrazol)-5-yl)-7-(B-D-ribofuranosyl)pyrrolo[2,3-d]pyrimidine using a procedure of Schram and Townsend, *J. Carbohydrate*, Nucleosides:Nucleotides 1, 38 (1974). Toyocamycin (1.0 g) dissolved in water (100 ml) and glacial acetic acid (13 ml) was heated to reflux. Sodium azide (7.5 g) was added in 1.25 g portions over 10 hours. The solution was cooled to 5° C. and the precipitated product collected, M.P. 276-277° C.

EXAMPLE XXVI

5-Cyano-2'-deoxyuridine was prepared according to Bleckley et al, *Nucl. Acids Res.* 2, 683 (1975). 5-Iodo-2'-deoxyuridine (1.0 g, 2.82 mmol) was dissolved in refluxing hexamethyldisilizane (HMDS) (10 ml). Excess HMDS was removed at reduced pressure, and the resulting oil was dissolved in dry pyridine (50 ml). Cuprous cyanide (350 mg, 3.8 mmol) was added, and the solution heated at 160° C. for 20 hours. Pyridine was removed at reduced pressure, and the residue extracted into toluene which was subsequently evaporated. The residue was heated in 50% aqueous ethanol at 100° for 2 hours. The product was purified by reverse-phase high pressure liquid chromatography and recrystallized from ethanol, M.P. 161° C.

EXAMPLE XXVII 4-amino-5-amino methylene-7-(β-D-2-deoxyfuranosyl) pyrrolo[2,3-d]pyrimidine dihydrochloride was obtained as follows. 4-amino-5-cyano-7-(β-D-2-deoxyfuranosyl)pyrrolo [2,3-d]pyrimidine (Toyocamycin) (0.2 g) was dissolved in hydrochloric acid (10 ml). 10% palladium on charcoal (0.1 g) was added as the mixture hydrogenated at 40 psi for 5 hours at room temperature. After filtration the water was evaporated at reduced pressure. The residue was triturated with ethanol, and the product recrystallized from 50% ethanol.

EXAMPLE XXVIII 5-amino-2'-deoxyuridine was prepared from 5-bromo-2'-deoxyuridine according to the procedure of Roberts and Visser, *J. Am. Chem. Soc.* 14:665-669 (1952). 5-bromo-2'-deoxyuridine (2 g, 6.2 mmol) dissolved in liquid ammonia (20 ml) was scaled in a glass tube and heated at 50° for 5 days. The tube was opened, and the ammonia was evaporated. 5-amino-2'-deoxyuridine was recrystallized from 5 ml water and 75 ml hot isopropyl alcohol.

EXAMPLE XXIX 5-(methylamino)-2'-deoxyuridine (0.2 g) was prepared as follows. 5-cyano-2'-deoxyuridine (0.2 g, 0.05 mol) was dissolved in 1 N hydrochloric acid (10 ml). 10% palladium on charcoal (0.1 g) was added, and the mixture hydrogenated at 40 p.s.i. for 10 hours at room temperature. The mixture was filtered and the water evaporated at reduced pressure. The residue was triturated with ether, and the product was recrystallized from 80% ethanol.

EXAMPLE XXX

Maltose triose was oxidized to the corresponding carboxylic acid by the following method. Maltose triose (0.5 g, 0.94 mmol) was dissolved in water (5 ml). Lead carbonate (0.42 g, 1.1 mmol) and bromine (0.17 ml), 3.3 mmol) were added, and the mixture was allowed to react at room temperature for six days after which no reducing sugar remained. The mixture was filtered, and silver carbonate (0.2 g) added. After refiltering, the filtrate was deionized by elution through Dowex 50 ($H^+$ form). Evaporation of water and drying in the presence of phosphorus pentoxide yielded the desired product.

EXAMPLE XXXI

Maltose triose was coupled to 5-(3-amino-1-propenyl)-2'-deoxyuridine-5' triphosphate by the following procedure. Oxidized maltose triose (190 mg, 0.18 mmol) was dissolved in dimethylformamide (0.8 ml) and cooled to 4° C. Isobutyl chloroformate (25 mg, 0.18 mmol) and tri-n-butylamine (43 ul, 0.38 mmol) were added, and the solution allowed to react at 4° C. for 15 minutes. 5-(3-amino-1-propenyl)-2'-deoxyuridine-5'-triphosphate (9.0 umol), dissolved in dimethyl formamide (1.2 ml) and 0.1 M sodium borate and cooled to 4° C., was added to the above solution. The mixture was incubated at 4° C. for 1 hour and at room temperature for 18 hours. It was then loaded on a DEAE-cellulose column and eluted with a gradient of 0.1 to 0.6 M triethylammonium bicarbonate, pH 7.5. The product was finally purified by reverse phase high pressure liquid chromatography.

Following are Examples XXXII and XXXIII. Example XXXII is a method of tagging allylamine modified dUTP with a fluorescein substituent. This is an example of creation of a self detecting nucleic acid probe. Example XXXIII is a method of labeling preformed double helical nucleic acids at the $N^2$ position of guanine and the $N^6$ position of adenine. Example XXXVII has the detector molecule linked to the probe. Chromosoma 84: 1-18 (1982) and Exp. Cell Res. 128:485-490, disclose end labeling of RNA with rhodamine. However, the procedure of this invention is less disruptive and labels internal nucleotides.

EXAMPLE XXXII

Fluorescein was coupled to 5-(3-amino-1-propyl)-2'-deoxyuridine-5'-triphosphate (AA-dUTP) as follows. AA-dUTP (10 umol), dissolved in 2 ml sodium borate buffer (0.1 m), pH 9.0, was added to fluorescein isothiocyanate (10 mg, 25 umol) dissolved in 1 ml dimethylformamide. After four hours at room temperature the mixture was loaded onto a DEAE-cellulose column equilibrated in triethylammonium bicarbonate buffer, pH 7.5. The fluorescein coupled AA-dUTP was purified by elution with a gradient of from 0.1 to 0.6 m triethylammonium bicarbonate, pH 7.5.

EXAMPLE XXXIII

DNA may be modified by reaction with chemical alkylating agents. Lambda DNA was alkylated in $N^2$ position of guanine and $N^6$ position of adenine by reacting DNA with aromatic hydrocarbon 7-bromomethylbenz[a]anthracene. 7-bromomethylbenz[a]anthracene was obtained as follows. 7-methyl[a]anthracene in carbon disulfide solution was cooled in a freezing mixture and treated dropwise with a molar equivalent of bromine. After 30 minutes, the product in suspension was collected, and was washed with dry ether and recrystallized from benzene. The yield was 66% with melting point 190.5-191.5° C.

DNA, purified from phage Lambda, (1.6 mg) was solubilized in 5.0 ml of 20 mM potassium phosphate pH 6.5. To 4.0 ml of DNA solution was added 500 micrograms 7-bromomethylbenz[a]anthracene in dry acetone. After 30 minutes at 20°, the DNA was precipitated with two volumes of cold ethanol. The precipitate was washed successively with ethanol, acetone and ether to remove any unbound 7-bromomethylbenz[a]anthracene. Enzymatic hydrolysis of the DNA to nucleosides and subsequent chromatography of the products on Sephadex® LH-20 columns, indicated that 18% of the adenine and 48% of the guanine in DNA were modified in $N^6$ and $N^2$ positions, respectively.

The modified DNA was made single stranded either by (1) heating to 100° for 5 minutes and rapid cooling or (2) incubating with equal volume of 0.1 M NaOH for 10 minutes and then dialyzing the solution for four hours against 1 ml tris-HCl pH 8.0 containing 0.5 ml EDTA to keep the DNA in single-stranded form.

EXAMPLE XXXIV

A DNA probe was ligated to a synthetic DNA composed of repeated sequences of *E. coli* lac operator DNA. After hybridization to detect antiprobe sequences, the hybridized DNA was detected by reaction with biotinylated lac repressor which was, in turn, detected by an enzyme linked immuno sorbent assay using goat antibiotin IGG to react with the biotin and a second antibody coupled to horse radish peroxidase. The lac polyoperator DNA has been described by Caruthers (Second Annual Congress for Recombinant DNA Research, Los Angeles, 1982), and it was ligated, in a blunt end ligation; using T4 ligase, to an adenovirus DNA probe. In situ hybridization of the polyoperator-labeled probe DNA was carried out as described by Gerhard et al (*Proc. Natl. Acad. Sci.* USA, 78, 3755 (1981). Biotinylated lac repressor was prepared as described by Manning et al (*Chromosoma*, 53, 107-117 (1075) and was applied to adenovirus infected cells, fixed to a glass slide, in Binding buffer composed of (0.01 MK Cl, 0.01 M tris (pH 7.6), 0.01 M $MgSO_4$, $10^{-4}$ MEDTA, $10^{-4}$ M DTT, 5% DMSO (dimethyl sulfoxide) and 50 ug/ml bovine serum albumin by J. Miller, *Experiments in Molecular Genetics*, Cold Spring Harbor Laboratory (1972). The slides were washed in binding buffer to remove unbound biotinylated lac repressor and then assayed for biotin using the horse radish peroxidase-linked double antibody procedure. This procedure could be adapted to create an affinity column where the probe could be bound to immobilized repressor protein and then removed by elution with a specific inducer, for example, isopropylthigalactoside or thiomethylgalactoside. The affinity of the repressor-operator complex is quite high $10^{-11}$ M. When a specific inducer binds to the repressor the operator-repressor complex collapses.

EXAMPLE XXXV

5-Bromo-2'-deoxyuridine-5'-phosphate was prepared as follows: 2'-Deoxyuridine-5'-phosphate (6.2 g) was suspended in a mixture of 60 ml pyridine and 30 ml acetic acid. Bromine (0.84 ml) was added with stirring in an ice water bath and stirring continued for 20 hours at room temperature. The solution was concentrated by vacuum. After redissolution in a minimum of water a crude product was precipitated by addition of ethanol. The crude product was chromatographed on Dowex 50 ($H^+$) and eluted with water. The free acid product was precipitated from the concentrated eluent by addition of ethanol.

EXAMPLE XXXVI

Calf intestine alkaline phosphatase was biotinylated as follows: The enzyme (1 mg, 7.7 mmol) was chromatographed on a G-50 column eluting with 0.1 M Hepes buffer pH 8.0 containing 0.1 M sodium chloride. The pooled fractions were reacted with N-biotinyl-6-amino-caproic acid-N-hydroxysuccinimide ester (0.675 mg, 0.77 umol) dissolved in 10 ml diemthylformamide at room temperature for 1 hour. Sodium periodate (0.1 M 125 ul) was added and stirring continued for 2 hours. The mixture as dialyzed at 4° overnight in 0.1 M. Hepes buffer pH 8.0 with 0.1 M NaCl after which the pH was adjusted to 7.4. Biotin hydrazide (0.1 M, 0.5 ml) dissolved in 0.1 M Hepes buffer pH 7.4 and 0.1 M NaCl was added and the reaction stirred for 30 minutes at room temperature. The pH was adjusted to 8.0 with 0.2 M sodium carbonate and 0.5 ml of freshly prepared 0.1 M sodium borohydride in water was added, the solution was dialyzed against 0.1 M tris buffer pH 8.0 with 0.1 M NaCl.

EXAMPLE XXXVII

6-Cyano-2-deoxyuridine-5'-phosphate was prepared similarly to a procedure of Veder et al, *J. Carbohydr. Nucleosides, Nucleotides,* 5, 261 (1978). 5-bromo-2'-deoxyuridine-5'-phosphoric acid (2.0 g, 15 mmol) dried by successive evaporation from pyridine was dissolved in 50 ml dimethylsulfide. Sodium cyanide (490 mg, 10 mmol) was added and the solution stirred at room temperature for 2 days. The solution was diluted with 400 ml water and the pH adjusted to 7.5. It was applied to a DEAE-cellulose column ($HCO_3^-$ form) washed with 2000 ml 0.02 M triethylammonium bicarbonate to yield the desired product.

EXAMPLE XXXVIII 6-(Methylamino)-2'-deoxyuridine-5'-phosphoric acid was prepared as follows: 6-Cyano-2'-deoxyuridine-5'-phosphoric acid (0.2 g, 60 mmol) was dissolved in 0.1 M hydrochloric acid. After addition of 10% palladium on charcoal (0.1 g), the mixture was hydrogenated at 40 psi for 20 hours at room temperature. The mixture was filtered, neutralized with lithium hydroxide and lyophilized. The product residue was extracted with ethanol.

EXAMPLE XXXIX

Horse radish peroxidase (20 mg) dissolved in 5 ml distilled water was added to 1.0 ml freshly prepared 0.1 M sodium periodate solution. After stirring at room temperature for 20 minutes it was dialyzed overnight at 4° C. against 1 mM sodium acetate pH 4.4. Biotin hydrazide (2.6 mg, 5×10–2 mmol) dissolved 2.0, 0.1 M Hepes buffer pH 7.4 with 0.1 M sodium chloride was brought to pH 8.0 with 0.2 M sodium carbonate and 0.5 ml of a freshly prepared 0.1 M sodium borohydride solution in water was added. After 2 hours at 4° C. the protein was purified on a Sephadex® G-50 column eluting with 0.1 M Hepes and 0.1 M NaCl.

EXAMPLE XL

Carrot acid phosphatase has been mentioned by Brunngraber and Chargaff, *J. Biol. Chem.*, (1967) 242, 4834-4840 as a byproduct of the purification of phosphotransferase and has been purified to a specific activity of 460 uM/mg/min at 37° C. with paranitrophenylphosphate as the substrate. The purification involved the steps of (a) absorption of non-specific proteins by DEAE cellulose; (b) acid purification of the enzyme; (c) acetone fractionation; (d) concanvalin A affinity chromatography; (e) hydroxyapatite chromatography and (f) Sephadex® G-100 fractionation. The specific activity of the enzyme subjected to the Sephadex G-100 fractionation due to loss of activity in the preceding affinity chromatography step (d) was 170 uM/mg/m. By changing elution conditions at step (d), these losses can be avoided with the result that the specific activity of the enzyme before the Sephadex G-100 fractionation can be improved to 340 uM/mg/m. The Sephadex® G-100 fractionation step should yield an enzyme having a specific activity of 800 uM/mg/m or higher. Carrot acid phosphatase was biotinylated using a procedure of Wilchek et al *Biochemistry* 6, 247 (1967). To the enzyme (20 mg) dissolved 0.1 M NaCl, pH 5, was added biotin hydrazide (2.0 mg, 7×10⁻³ mmol) and 1-ethyl-3-(3-diimenthylaminopropyl)carbodimide hydrochloride (1 mg, 7×10⁻³ mmol) dissolved in 0.1 M NaCl, pH 5. After 2 hours at 4° C. the enzyme was chromatographed on Sephadex® G-50 eluting with 0.1 M sodium acetate, pH 5.0. Of special importance and significance in the practices of this invention is the utilization of self-signaling or self-indicating or self-detecting nucleic acids, particularly such nucleic acids which are capable of being incorporated in double-stranded DNA and the like. Such self-signaling or self-detecting nucleic acids can be created by covalently attaching to an allylamine substituent making up a modified nucleotide in accordance with this invention a molecule which will chelate specific ions, e.g. heavy metal, rare earths, etc. In general, the chelated ion can be detected either. (a) by radioactive emission or (b) by using the ion to catalyze a chromogenic or fluorogenic reaction.

By way of example, a solution of 3,4-dinitro phenol is reduced to 3,4-diamino cyclohexane

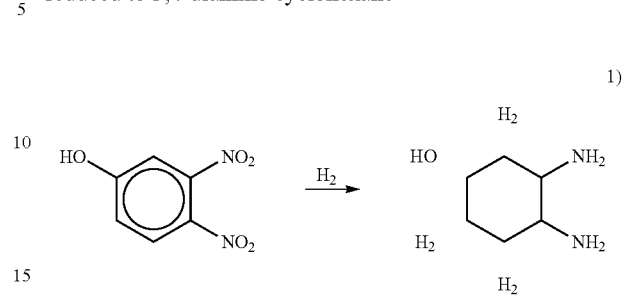

This material is then brominated

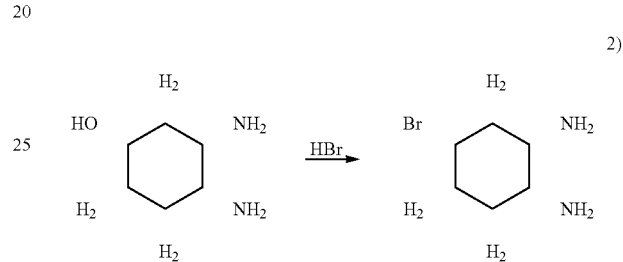

to form 3,4-diamino bromo cyclohexane (dABCH). This compound is reacted with halide (Cl, Br, I) substituted carboxymethyl compound to produce a tetra carboxymethyl derivative or dABCH (TCM-dABCH):

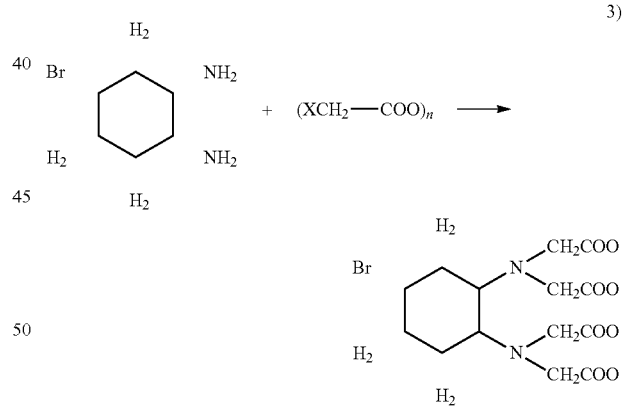

The bromine is substituted by an amino group using soluble ammonia:

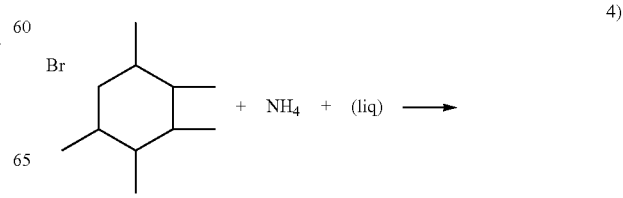

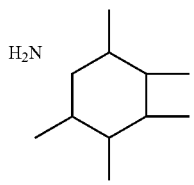

Then this compound is reacted with chloro thiophosgene to produce the isothiocyanate derivative of (TCM-dANCH).

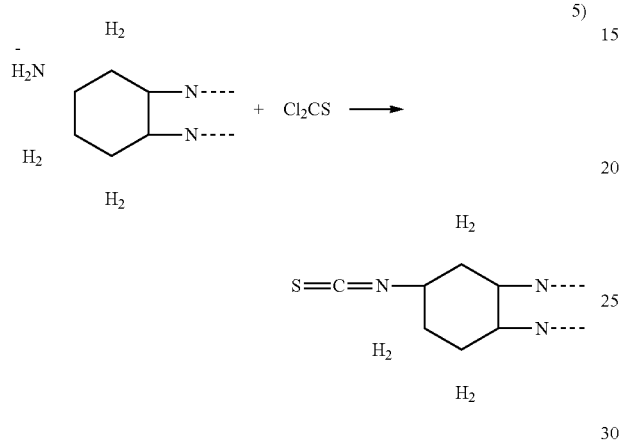

Finally, this compound is reacted with dUTP-allylamine derivative to produce modified dUTP.

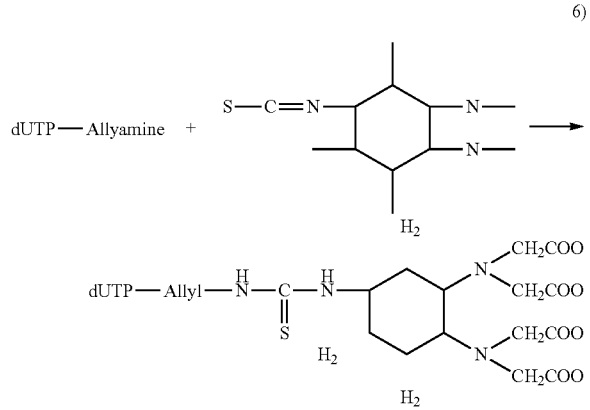

Cobalt or other heavy metal ions or other rare earth ions can be chelated to the compound after step 3 above. Or the nucleic acid can be substituted with this adduct and then the ion added. (Example, cobalt is added at pH 6 where the binding constant is $10^{-19}$M).

Cobalt can be assayed by radioactivity. It can also be detected by its ability to oxidize methylene blue to the leuco form in the presence of molecular oxygen. It can be used to oxidize soluble sulfhydro groups to disulfide bonds again in the presence of molecular oxygen.

This type of self-signaling molecule can be used to monitor any nucleic acid hybridization reaction. It is particularly important for detecting nucleic acids in gels (for example, sequencing gels).

With respect to its use in radioactivity, it can be used to tailor the isotope needed, i.e. if a weak or strong β or γ emitter is needed, that isotope can be chelated. Examples of isotopes that can be used are listed immediately hereinafter.

| | | |
|---|---|---|
| Antimony-124 | Iodine-125 | Scandium-44 |
| Antimony-125 | Iodine-131 | Scandium-46 |
| Arsenic-74 | Iodine-132 | Selenium-75 |
| Barium-133 | Iridium-192 | Silver-110m |
| Barium-140 | Iron-55 | Silver-111 |
| Beryllium-7 | Iron-59 | Sodium-22 |
| Bismuth-206 | Krypton-85 | Strontium-85 |
| Bismuth-207 | Lead-210 | Strontium-89 |
| Cadmium-109 | Lutecium-177 | Strontium-90 |
| Cadmium-115m | Manganese-54 | Tantalum-182 |
| Calcium-45 | Mercury-197 | Technetium-99 |
| Carbon-14 | Mercury-203 | Tellurium-125m |
| Cerium-139 | Molybdenum-99 | Tellurium-132 |
| Cerium-141 | Neodymium-147 | Terbium-160 |
| Cerium-144 | Neptunium-237 | Thallium-204 |
| Cesium-134 | Nickel-63 | Thorium-228 |
| Cesium-137 | Niobium-95 | Thorium-232 |
| Chlorine-36 | Osmium-185 + 191 | Thulium-170 |
| Chromium-51 | Palladium-103 | Tin-113 |
| Cobalt-56 | Platinum-195m | Titanium-44 |
| Cobalt-57 | Praseodymium-143 | Tritium |
| Cobalt-58 | Promethium-147 | Tungsten-185 |
| Cobalt-60 | Protactinium-233 | Vanadlum-48 |
| Erbium-169 | Radium-226 | Vanadium-49 |
| Europium-152 | Rhenium-186 | Ytterbium-169 |
| Gadolinium-153 | Rubidium-86 | Yttrium-88 |
| Gold-195 | Ruthenium-103 | Yttrium-90 |
| Gold-199 | Ruthenium-106 | Yttrium-91 |
| Hafnium-175 | | Zinc-65 |
| Hafnium-175 + 181 | | Zirconium-95 |
| Hafnium-181 | | |
| Hydrogen-3 see Tritium | | |

Streptavidin, a protein produced by a *Streptomyces avidinii* is a large molecular weight component of a synergistic pair of compounds which are both present in the culture filtrates of this microorganism. Each of the pair is inactive but in combination are active against gram-negative microorganisms. It has been found that the small component of this antibiotic prevents de novo synthesis of the vitamin biotin and thus, at least in synthetic media, show antimicrobial activity. In complex medium, however, the large component has to be included to exert the same effect on bacteria. This has been shown to be due to the presence of external biotin in the complex medium. The large molecular component has been found to bind external biotin and thus demon-strating the same kind of action as avidin from eggs and oviduct tissues of laying birds.

Streptavidin has been purified and shown to be a 60,000 dalton polypeptide. Like avidin, streptavidin contains four subunits and binds tightly four molecules of biotin. Unlike avidin, however, it is non-glycosylated and it has PI of 5.0 as compared to avidin with PI=10.5. Due to the difference in pI streptavidin does not have a tendency to non-specifically interact with DNA.

Preparation of Streptavidin

A semi-synthetic medium containing salt, 1% glucose, 0.1% asparagine, 0.05% yeast extract and trace elements was prepared. The cultures were grown at 26° C. for three days. Mycellium was removed by centrifugation and protein in the supernatant were absorbed to DEAE-cellulose in a batchwise process after pH was adjusted with 1M HCl to 7.2. DEAE-cellulose was filtered off and washed with 20 mM Tris-HCl (pH 7.2) until no absorbancy at 280 nm was recorded. Streptavidin was eluted with 20 mM Tris-HCl (pH 7.2) containing 0.5 M NaCl. Ammonium sulfate precipitation was used to further concentrate the streptavidin (50% w/v at 4° C.).

The precipitate was dissolved in water and dialyzed against 1.0 M NaCl, 50 mM Na$_2$CO$_3$. In the next step affinity column chromatography on iminobiotin sepharose was used. Eluted streptavidin from iminobiotin sepharose column was shown to be chromatographically pyre by non-denaturing agarose-gel electrophoresis.

The final purification of streptavidin is accomplished by affinity purification through an iminobiotin-sepharose column. Iminobiotin is an analog of biotin in which the carbonyl of the urea moiety is substituted with an imine function. Iminobiotin will bind avidin and streptavidin at basic pH but the complex is dissociable at acidic pH.

Iminobiotin is prepared from biotin in several steps. Biotin is hydrolyzed by barium hydroxide to cis-3,4-diamino-2-tetrahydrothiophene-valeric acid which is reacted with cyanogen bromide to iminobiotin. The iminobiotin is coupled to amino sepharose via the N-hydroxysuccinimide ester of its hydrobromide salt.

The crude protein Mixture from DEAE eluted *Streptomyces avidinii* incubation media is dissolved in 50 mM sodium carbonate and 1.0 M sodium chloride (pH 11) and applied to an iminobiotin column pre-equilibrated with this solution. The column is eluted at pH 11. Streptavidin is subsequently eluted with 50 mM ammonium acetate, pH 4.0 containing 0.5 M sodium chloride. The eluent is dialyzed three times against 1 mM Tris pH 7.4 and lyophilized to dryness.

In the practices of this invention avidin is useful as a detecting mechanism for labeled DNA, such as biotin-labeled DNA. However, avidin itself, such at about neutral pH, complexes with DNA with the result that any signal derivable from a complex between biotin-labeled DNA and avidin might be lost or be non-detectable in the background due to the complex formation between avidin and unlabeled DNA. This disadvantage of the use of avidin in the practices of this invention is not possessed by streptavidin which does not form a complex with DNA at about neutral pH but is capable of forming a complex with the biotin portion of biotin-labeled DNA.

In another aspect directed to the broad utility of avidin and streptavidin for detecting labeled compounds other than DNA, avidin and streptavidin are particularly effective as detecting mechanisms for labeled proteins, polysaccharides and lipids. By way of example, one can fix to a solid matrix a specific antigen and bind to this antigen an antibody directed against this antigen which itself has been biotinylated. Then one can assay for the presence of this biotinylated antibody by reacting it with avidin or streptavidin complexed with an enzyme, such as calf intestine alkaline phosphatase, or to which fluorescing molecule, as for example fluoroscein has been linked.

The use of the antigen-antibody system for detecting either antigen or antibody is well known. A comparable system is a system based on a glycosylated substrate or molecule and matching or appropriate lectin. In this system the lectin would carry a label, such as fluorescein or appropriate enzyme. In this glycosyl-lectin system the labeled lectin forms a complex with the glycosyl moiety, comparable to the antigen-antibody complex, and this complex, comprising the glycosylated molecule and, appropriate labeled lectin having the necessary glycosyl or sugar moiety specificity would then present itself eliciting the expected response from the label portion of the labeled lectin making up the glycosyl-lectin complex.

Another aspect of the practices of this invention which is particularly advantageous is to carry out the detection or hybridization in the liquid phase between the DNA sought to be detected and the DNA detecting probe. In this liquid phase system both the DNA molecule to be detected and the appropriate DNA detecting probe are not attached to any insoluble substrate or any insoluble chemical moiety. The advantages of the liquid phase detection system reside in the speed of hybridization or hybrid formation between the DNA to be detected and the appropriate DNA probe therefor. For example, in a solid-liquid system the time required to effect recognition and hybridization formation is about ten times greater than if it were carried out in a completely liquid system, i.e. both DNA to be detected and the detecting DNA are not attached to an insoluble moiety.

The probes prepared in accordance with the practices of this invention are adaptable for use in the detection of viruses and bacteria in fluids as indicated herein-above. Where the fluids to be examined do not contain large amounts of protein, the viruses therein can be concentrated by absorption on hydroxyapatite and eluted in a small amount of phosphate buffer. When the fluid to be examined contains large amounts of protein, the viruses can be concentrated by high speed centrifugation.

If antibody were available, absorption on an affinity column and elution with acid would be preferable because it would be possible to process many probes in accordance with the practices of this invention at the same time. The bacteria to be examined is usually readily concentrated by centrifugation.

In accordance with the practices of this invention, the identification or characerization of the isolated particles, viruses and bacteria, would be hybridization of the characterizing or identifying DNA thereof with a specific single stranded DNA probe prepared in accordance with the practices of this invention. After hybridization, excess non-hybridized probe DNA would be digested with s$_1$ nuclease and exonclease I from *E. coli* at high salt content to suppress the nicking activity of the S$_1$ nuclease, see Vogt, *Methods in Enzymology*, Vol. 65, pages 248-255 (1980). This nuclease treatment would produce mononucleotides from the excess, non-hybridized single-stranded DNA probe but would leave the double-stranded, hybridized DNA intact. This would then be absorbed at high salt content on Dowex anion exchanger (the nucleotides and the small amount of oligonucleotides will not bind to the resin in high salt concentration). The resulting hybridized DNA would then be identified or characterized by various procedures applicable to the practices of this invention.

The special nucleotides of this invention include a phosphoric acid P moiety (also designated hereinbelow as PM), a sugar or monosaccharide S moiety (also designated hereinbelow as SM), a base B moiety, (also designated hereinbelow as BASE) a purine or a pyrimidine and a signalling chemical moiety Sig covalently attached thereto, either to the P, S or B moiety (referred to hereinbelow as "PM," "SM" and "BASE," respectively). Following are structural formulas of various base B moieties (BASE) and nucleotides which are modified in accordance with the practices of this invention.

The Major Purines

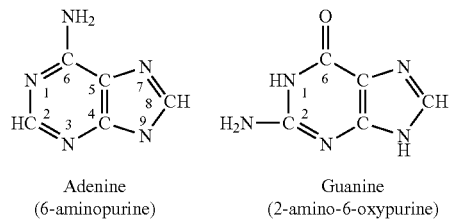

Adenine
(6-aminopurine)

Guanine
(2-amino-6-oxypurine)

Two Minor Purines

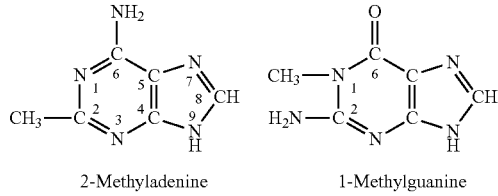

2-Methyladenine        1-Methylguanine

The Major Pyrimidines

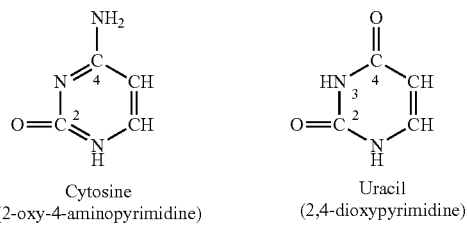

Cytosine                Uracil
(2-oxy-4-aminopyrimidine)   (2,4-dioxypyrimidine)

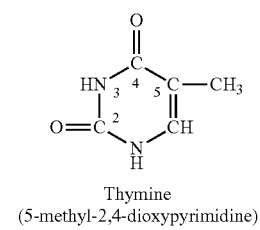

Thymine
(5-methyl-2,4-dioxypyrimidine)

Two Minor Pyrimidines

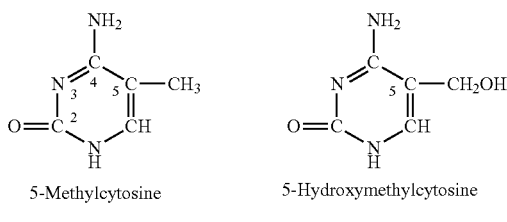

5-Methylcytosine        5-Hydroxymethylcytosine

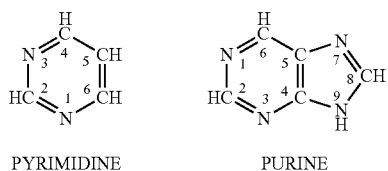

PYRIMIDINE              PURINE

The major ribonucleotides and deoxyribonucleotides.

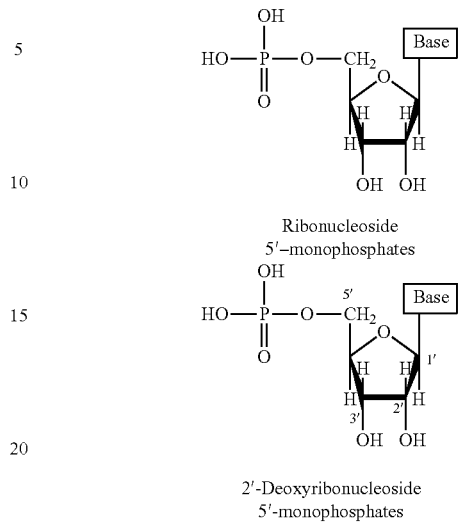

Ribonucleoside
5′–monophosphates

2′-Deoxyribonucleoside
5′-monophosphates

| General Structure Names | General Structure Names |
|---|---|
| Adenosine 5'-phosphoric acid (adenylic acid; AMP) | Deoxyadenosine 5'-phosphoric acid (deoxyadenylic acid; dAMP) |
| Guanosine 5'-phosphoric acid (guanylic acid; GMP) | Deoxyguanosine 5'-phosphoric acid (deoxyguanylic acid; dGMP) |
| Cytidine 5'-phosphoric acid (cytidylic acid; CMP) | Deoxycytidine 5'-phosphoric acid (deoxycytidylic acid; dCMP) |
| Uridine 5'-phosphoric acid (uridylic acid; UMP) | Deoxythymidine 5'-phosphoric acid (deoxythymidylic acid; dTMP) |

The special nucleotides in accordance with this invention, as indicated hereinabove, in addition to the P, S and B moieties (PM, SM and BASE, respectively), include a chemical moiety Sig covalently attached to the P, S and/or B moieties (PM, SM and BASE, respectively). Of special interest in accordance with the practices of this invention would be those nucleotides having the general formula, P-S-B-Sig (PM, SM-BASE-Sig) wherein P (PM) is the phosphoric acid moiety including mono-, di-, tri-, or tetraphosphate, S (SM) the sugar or monosaccharide moiety, B the base moiety (BASE, either a purine or a pyrimidine. The phosphoric acid moiety P (PM) is attached at the 3' and/or the 5' position of the S moiety (SM) when the nucleotide is a deoxyribonucleotide and at the 2', 3' and/or 5' position when the nucleotide is a ribonucleotide. The base B moiety (BASE is attached from the N1 position or the N9 position to the 1' position of the S moiety (SM) when the base moiety is a pyrimidine or a purine, respectively. The Sig moiety is covalently attached to the B moiety (BASE) of the nucleotide and when so attached is capable of signalling itself or makes itself self-detecting or its presence known and desirably or preferably permits the incorporation of the resulting nucleotide P-S-B-Sig (PM-SM-BASE-Sig) into or to form a double-stranded helical DNA or RNA or DNA-RNA hybrid and/or to be detectable thereon.

In accordance with the last-described nucleotides this invention provides nucleotides wherein the base is a pyrimidine and the Sig chemical moiety is attached to the pyrimidine at the N3 position. Also provided are such nucleotides wherein the base is a pyrimidine and the Sig chemical moiety is attached to the pyrimidine at the C6 position.

Also in accordance with the nucleotides described above, this invention provides other nucleotides wherein the base is a purine and the Sig chemical moiety is attached to the purine at the N1 position. Other nucleotides are provided wherein the base is a purine and the Sig chemical moiety is attached to the purine at the C2 position. Still other nucleotides are provided wherein the base is a purine and the Sig chemical moiety is attached to the purine at the N3 position. This invention also provides nucleotides wherein the base is a purine and the Sig chemical moiety is attached to the purine at the N7 position.

Another special nucleotide in accordance with this invention is characterized by the general formula:

Such nucleotides in accordance with this invention would be characterized as ribonucleotides. The phosphoric acid moiety (PM) is attached at the 2', 3' and/or 5' position of the sugar S moiety (SM) and the base B (BASE) being attached from the N1 position or the N9 position to the 1' position of the sugar S moiety (SM) when said base (BASE) is a pyrimidine or a purine, respectively. The Sig chemical moiety is covalently attached to the sugar S moiety (SM) and said Sig chemical moiety when attached to said S moiety (SM) is capable of signalling itself or making itself self-detecting or its presence known and preferably permits the incorporation of the ribonucleotide into its corresponding double-stranded RNA or a DNA-RNA hybrid.

Such nucleotides P-S-B

desirably have the Sig chemical moiety attached to the C2' position of the S moiety (SM) of the C3' position of the S moiety (SM).

Still further, nucleotides in accordance with the practices of this invention include the nucleotides having the formula,

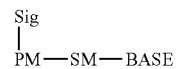

wherein P (PM) is the phosphoric acid moiety, S the sugar moiety (SM) and B the base moiety (BASE). In these special nucleotides the P moiety (PM) is attached to the 3' and/or the 5' position of the S moiety (SM) when the nucleotide is deoxyribonucleotide and at the 2', 3' and/or 5' position when the nucleotide is a ribonucleotide. The base B (B) is either a purine or a pyrimidine and the B moiety (BASE) is attached from the N1 or the N9 position to the 1' position of the sugar moiety when said B moiety (BASE) is a pyrimidine or a purine, respectively. The Sig chemical moiety covalently attached to the phosphoric acid P moiety (PM) via the chemical linkage

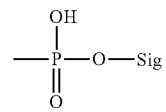

said Sig, when attached to said P moiety (PM) being capable of signalling itself or making itself self-detecting or its presence known and desirably the nucleotide is capable of being incorporated into a double-stranded polynucleotide, such as DNA, RNA or DNA-RNA hybrid and when so incorporated therein is still self-detecting.

It is pointed out that the special nucleotides in accordance with the practices of this invention described or defined hereinabove by the general formula P-S-B-Sig (PM-SM-BASE-Sig), also include nucleotides wherein the Sig chemical moiety is covalently attached to the B moiety (BASE) at the $N^6$ or 6-amino group position when the B moiety (BASE) is adenine or the $N^2$ or 2-amino group position when the B moiety (BASE) is guanine or the $N^4$ or 4-amino group position when the B moiety is cytosine. The resulting nucleotides containing the Sig moiety attached thereto are capable of signalling themselves or making themselves self-detecting or their presence known and being detectable is a double-stranded or DNA, RNA or DNA-RNA hybrid.

By way of summary, as indicated hereinabove with respect to the make-up of the various special nucleotides in accordance with this invention, the special nucleotides can be described as comprising a phosphoric acid moiety P (PM), a sugar moiety S (SM) and a base moiety B (BASE), a purine or pyrimidine, which combination of P-S-B (PM-SM-BASE is well known with respect to and defines nucleotides, both deoxyribonucleotides and ribonucleotides. The nucleotides are then modified in accordance with the practices of this invention by having covalently attached thereto, to the P moiety (PM) and/or the S moiety (SM) and/or the B moiety (BASE), a chemical moiety Sig. The chemical moiety Sig so attached to the nucleotide P-S-B (PM-SM-BASE) is capable of rendering or making the resulting nucleotide, now comprising P-S-B (PM-SM-BASE) with the Sig moiety being attached to one or more of the other moieties, self-detecting or signalling itself or capable of making its presence known per se, when incorporated into a polynucleotide, especially a double-stranded polynucleotide, such as a double-stranded DNA, a double-stranded RNA or a double-stranded DNA-RNA hybrid. The Sig moiety desirably should not interfere with the capability of the nucleotide to form a double-stranded polynucleotide containing the special Sig-containing nucleotide in accordance with this invention and, when so incorporated therein, the Sig-containing nucleotide is capable of detection, localization or observation.

The Sig moiety employed in the make-up of the special nucleotides of this invention could comprise an enzyme or enzymic material, such as alkaline phosphatase, glucose oxidase, horseradish peroxidase ribonuclease acid phosphatase or beta-galactosidase. The Sig moiety could also contain a fluorescing component, such as fluorescein or rhodamine or dansyl. If desired, the Sig moiety could include a magnetic component associated or attached thereto, such as a magnetic oxide or magnetic iron oxide, which would make the nucleotide or polynucleotide containing such a magnetic-containing Sig moiety detectable by magnetic means. The Sig moiety might also include an electron dense component, such as ferritin, so as to be available by observation. The Sig moiety could also include a radioactive isotope component, such as radioactive cobalt, making the resulting nucleotide observable by radiation detecting means. The Sig moiety could also include a hapten component or per se be capable of complexing with an antibody specific thereto. Most usefully, the Sig moiety is a polysaccharide or oligosaccharide or monosaccharide, which is capable of complexing with or being attached to a sugar or polysaccharide binding protein, such as a lectin, e.g. Concanavilin A. The Sig component or moiety of the special nucleotides in accordance with this invention could also include a chemiluminescent component.

As indicated in accordance with the practices of this invention, the Sig component could comprise any chemical moiety which is attachable either directly or through a chemical linkage or linker arm to the nucleotide, such as to the base B component (BASE) therein, or the sugar S component (SM) therein, or the phosphoric acid P component (PM) thereof.

The Sig component of the nucleotides in accordance with this invention and the nucleotides and polynucleotides incorporating the nucleotides of this invention containing the Sig component are equivalent to and useful for the same purposes as the nucleotides described in the above-identified U.S. patent application Ser. No. 255,223 now U.S. Pat. No. 4,711,955. More specifically, the chemical moiety A described in U.S. patent application Ser. No. 255,223 is functionally the equivalent of the Sig component or chemical moiety of the special nucleotides of this invention. Accordingly, the Sig component or chemical moiety of nucleotides of this invention can be directly covalently attached to the P, S or B moieties (PM, SM or BASE, respectively) or attached thereto via a chemical linkage or linkage arm as described in U.S. patent application Ser. No. 255,223, as indicated by the dotted line connecting B and A of the nucleotides of U.S. Ser. No. 255,223. The various linker arms or linkages identified in U.S. Ser. No. 255,223 are applicable to and useful in the preparation of the special nucleotides of this invention.

The Sig chemical moiety can comprise any of the following:
   an aliphatic chemical moiety containing at least 4 carbon atoms;
   an aliphatic chemical moiety containing at least 3 carbon atoms and at least one double bond; and
   an aromatic or a cycloaliphatic group containing at least six or at least five carbon atoms.

A particularly important and useful aspect of the special nucleotides of this invention is the use of such nucleotides in the preparation of DNA or RNA probes. Such probes would contain a nucleotide sequence substantially matching the DNA or RNA sequence of genetic material to be located and/or identified. The probe would contain one or more of the special nucleotides of this invention. A probe having a desired nucleotide sequence, such as a single-stranded polynucleotide, either DNA or RNA probe, would then be brought into contact with DNA or RNA genetic material to be identified. Upon the localization of the probe and the formation of a double-stranded polynucleotide containing the probe and the matching DNA or RNA material to be identified, the resulting formed double-stranded DNA or RNA-containing material would then be observable and identified. A probe in accordance with this invention may contain substantially any number of nucleotide units, from about 5 nucleotides up to about 500 or more, as may be required. It would appear that 12 matching, preferably consecutive, nucleotide units would be sufficient to effect an identification of most of the DNA or RNA material to be investigated or identified, if the 12 nucleotide sequence of the probe matches a corresponding cooperative sequence in the DNA or RNA material being investigated or to be identified. As indicated, such probes may contain one or more of the special Sig-containing nucleotides in accordance with this invention, preferably at least about one special nucleotide per 5-10 of the nucleotides in the probe.

As indicated hereinabove, various techniques may be employed in the practices of this invention for the incorporation of the special nucleotides of this invention into DNA and related structures. One particularly useful technique referred to hereinabove involves the utilization of terminal transferase for the addition of biotinated dUMP onto the 3' ends of a polypyrimidine or to single-stranded DNA. The resulting product, such as a single-stranded or cloned DNA, which has biotinated dUMP attached to the 3' ends thereof, can be recovered by means of a Sepharose-avidin column wherein the avidin would complex with the biotinated dUMP at the ends of the DNA and be subsequently recovered. In accordance with the practices of this invention hybridization to mRNA could be accomplished in solution and the resulting hybrid recovered via a Sepharose-avidin column and the mRNA recovered therefrom. Similar techniques could be employed to isolate DNA-RNA hybrids. This technique employing terminal transferase for the addition of the special nucleotides in accordance with this invention is widely applicable and the resulting modified nucleotides containing the special nucleotides in accordance with this invention including the special biotinated nucleotides or the special glycosylated nucleotides could be selectively recovered via complexing with avidin upon a Sepharose-avidin column or complexing with a lectin, such as Concanavalin A or a Sepharose-Concanavalin A column.

Illustrative of the practices of this invention, biotinated dUTP was added to the 3' ends of d[pT]$_4$ as well as single and double stranded DNA employing terminal transferase and the resulting product was purified through G-50 Sepharose and separated on a Sepharose-avidin affinity column. It was found that 69% of the d[pT]$_4$ molecules were biotinated and recovered on the Sepharose-avidin column. The results of this experiment established that terminal transferase added biotinated dUMP to the 3' ends of a polypyrimidine.

The detection of nucleic acids to which specific molecules have been covalently attached can be effected through the use of many naturally occurring proteins to which small molecules are known to specifically bind. In this procedure the small molecules are bound to the nucleotide using the allyl amine side chain. These nucleotides are then incorporated into specific nucleic acids using a DNA or RNA polymerase or ligase reaction or a chemical linkage. After annealing this probe with a complementary antiprobe sequence, the presence of the probe is assayed for by the specific binding of the protein to the ligand covalently bound to the probe.

Examples of protein-ligand reactions that are appropriate for this type of detector system include:
1. Enzymes and allosteric effector or modulator molecules. An example of this is the enzyme threonine dehydratase which is a heterotropic enzyme in that the effector molecule, L-isoleucine, is different than the substrate, L-threonine, J. Monod, J. Wyman and J. P. Changeux (1965), *J. Mol. Biol.* 12:88-118.
2. Effector molecules involved in regulation. An example of this is the specific binding of 3',5-cyclic adenosine monophosphate to the cyclic AMP receptor protein, I. Pastan and R. Perlman, *Science* 169:339-344 (1969). Another example is the lactose repressor molecule and the inducer molecules isopropylthiogalactoside or thiomethylgalactoside. These two inducer molecules are called gratuitous inducers in that they are not metabolized by the enzymes they induce, W. Gilbert and B. Muller-Hill, Proc. Natl. Acad. Sci. (US), 70:3581-3584, (1973).

3. Hormone receptors and other receptors on the surface of the cell to which organic molecules will specifically bind. An example of this is the epinephrine-epinephrine receptor system in which epinephrine is bound in a steriospecific manner with a high affinity to the receptor. With this system, since the receptor protein is insoluble in water, it will be imbedded in a lipid bilayer structure as for instance a liposome. Suitable detector systems would include specific enzymes or fluorescent molecules inside or within the lipid bilayer.

4. Specific ligand binding proteins included in the transport of small molecules. An example of this is the periplasmic binding proteins of bacteria which have been shown to bind many amino acids, glucose, galactose, ribose and other sugars, Pardee, A. *Science,* 162:632-637, (1968); G. L. Hazelbaur, and J. Adler, *Nature New Bio.* 230: 101-104, (1971).

In the above-mentioned examples the ligand bound to the nucleic acid reacts with a naturally occurring protein. The specificity of this reaction resides in the ligand-binding site of the protein.

One further example of small molecule interaction with naturally occurring proteins involves the specific binding of coenzyme or other prosthetic molecules to enzymes. Examples of such coenzymes include thiamin pyrophosphate, flavine mononucleotide, flavine adenine dinucleotide, nicotinamide adenine dinucleotide, nicotinamide adenine dinucleotide phosphate, coenzyme A, pyridoxyl phosphate, biotin, tetrahydrofolic acid, coenzyme $B_{12}$, lipoic and ascorbic acid. Many of these molecules form covalent linkages with their apoenzymes.

However, some, for example, coenzyme A, coenzyme $B_{12}$ and tetrahydrofolic acid, associate in a non-covalent but specific manner with their cognate apoenzymes. A specific coenzyme-apoenzyme system for use in this system is flavine adenine dinucleotide (FAD) and flavine adenine dinucleotide reductase isolated from *Escherichia coli*. With this system the binding of FAD is sufficiently strong to permit detection.

The special nucleotides of this invention and poly-nucleotides including such nucleotides, either single-stranded or double-stranded polynucleotides, DNA and/or RNA, comprising the components, phosphoric acid moiety P, (PM) the sugar or monosaccharide moiety S (SM) the base moiety B, (BASE) a purine or a pyrimidine, and the signalling or self-detecting moiety, Sig, covalently attached to either the P, S or B moieties, (PM) SM, or BASE as indicated hereinabove, have many uses and utilities. For example, the nucleotides of this invention and polynucleotides containing the nucleotides of this invention are useful as immune-stimulating agents, as adjuvants in vaccines, as agents for the stimulation or induction from competent cells, such as lymphocytes, for the production of lymphokines, cytokines or cytokinins, interferon or other cellular products.

It is well known that double-stranded poly A:U is a stimulator or inducer for the production of interferon, although weakly so. Similarly, poly I:C is also known as a stimulator or inducing agent for the production of interferon.

The advantage of polynucleotides, such as double-stranded polynucleotides incorporating one or more nucleotides in accordance with this invention is that, in effect, such polynucleotides would be more effective and more powerful inducing or stimulating agents for the production of interferon and related materials from cells. For example, nucleotides in accordance with this invention containing the above-described components P, S, B and Sig, (PM, SM, BASE and Sig, respectively) are suitably prepared so that the nucleotides and polynucleotides prepared therefrom are more resistant to nucleases. Similarly, such nucleotides and polynucleotides containing the same and suitably prepared which are more capable of contacting, stimulating and penetrating cellular surfaces or membranes, such as the cellular surfaces or membranes of lymphocytes and other cells so as to stimulate the same for the production of a desired cellular product, such as interferon.

Particularly useful among those special nucleotides in accordance with this invention having the formula P-S-B-Sig PM-SM-BASE-Sig and especially useful are those wherein the Sig component is at the 5 position of the pyrimidine or the 7 position of the purine or a deazapurine or the $N^2$ position of guanine or the $N^6$ position of adenine. Such nucleotides and polynucleotides incorporating the same, both single-stranded and double-stranded nucleotides, DNA and/or RNA are prepared in accordance with this invention to provide increased stability with respect to the double-stranded helix of DNA or RNA or DNA-RNA hybrid containing the same. Increased resistance to nucleases is also achievable as well as alterations or favorable changes in the hydrophobic properties or electrical or charge properties of the nucleotides and polynucleotides containing the same. Also, nucleotides and polynucleotides in accordance with this invention are prepared which, when administered to humans, have reduced pyrogenicity or exhibit less other whole body toxic responses. Additionally, the nucleotides and polynucleotides are prepared in accordance with this invention to provide a ligand, such as the component Sig, to which specific polypeptides can combine to create or bring about the formation of RNA complexes. It is seen therefore that the nucleotides of this invention include the P, S, B and Sig component (PM, SM, BASE and Sig, wherein the Sig is covalently attached to either the P, S or B moieties (PM, SM and BASE, respectively) open up or provide a whole array of chemical agents having special biological effects including therapeutic effects and cytotoxic effects.

The special nucleotides of this invention, including polynucleotides containing these nucleotides, in addition to being stimulating or inducing agents for the production of cellular materials or products, such as interferons, lymphokines and/or cytokines, are also useful for their chemotherapeutic effect and for the preparation of chemotherapeutic agents based thereon but also for their cytotoxic effects and the production of cytotoxic agents based thereon. The moiety Sig attached to the special nucleotides of this invention containing the other moieties or components P, S, B (PM, SM, BASE) provides a site per se for the attachment thereto, the Sig component, of special agents of known chemotherapeutic or cytotoxic effect. Such nucleotides could be introduced or administered to the subject being treated, e.g. human body or animal, so as to be incorporated into the DNA and/or RNA components of the body or cell so as to either interfere with the synthesis of the body or cellular DNA and/or RNA or to attack tumors or to, in effect, kill or otherwise interfere with the growth of undesired cells.

The administration of the nucleotides and/or polynucleotides containing the nucleotides to the body, human body or animal, can be effected by a number of suitable means. Particularly effective would be the intravenous introduction to the body of preparations containing the nucleotides of this invention and a suitable physiologically acceptable carrier or the nucleotides could be administered subcutaneously, transdermally, or intramuscularly or by direct introduction into the site where the chemotherapeutic or cytotoxic effect of the nucleotides is sought or desired to be effective. Not only could desired chemotherapeutic or cytotoxic effects be achieved systemically or locally but also, as indicated hereinabove, the special P, S, B and Sig-containing nucleotides of this invention, including polynucleotides containing such nucleotides, are useful as immune-stimulating agents and adjuvants therefor. Accordingly, vaccines containing the special nucleotides and polynucleotides in accordance with this invention can be prepared having improved effectiveness and versatility.

Of special interest in the practices of this invention improved polynucleotides incorporating the special nucleotides of this invention are provided as inducers or stimulating agents for the production of interferon. Such polynucleotides would be single-stranded or double-stranded ribonucleotides, dsRNA, having the structures,

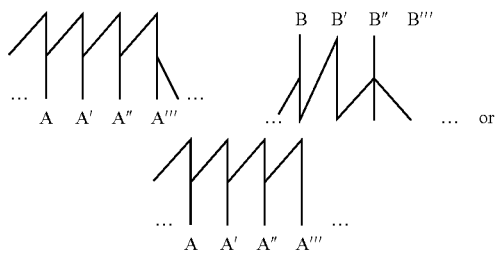

where A and B are complementary base pairs, such as a purine, a 7-deazapurine or pyrimidine modified by the addition of an organic moiety Sig in accordance with the disclosures of this invention on the 5 position of the pyrimidine ring or the 7 position of the purine ring or the $N^2$ of guanine, or the $N^6$ of adenine or the $N^4$ of cytosine as described herein. The modifications of the polynucleotides at these positions lead to relatively undisruptive or non-disruptive double-stranded nucleic acid molecules as measured by rates of association and melting points. In the special polynucleotides of this invention employed as inducers of interferon and other cellular or humoral factors or components, such as lymphokines or cytokines, the following groups would be attached thereto as indicated by the formulas,

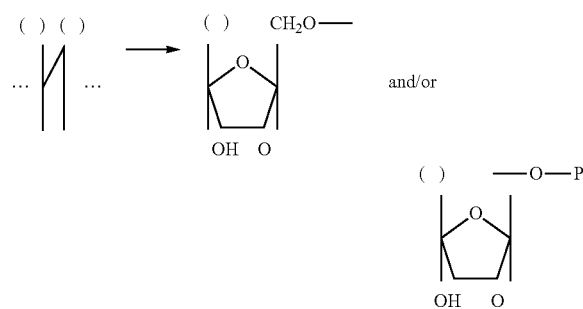

In the utilization of the special polynucleotides of this invention, such as the special dsRNA of this invention in the induction process for the production of interferon it has been demonstrated that DEAE-dextran facilitates this operation. It appears that DEAE-dextran complexes with dsRNA and protects it from nuclease degradation, thereby enhancing interferon induction. It has also been noted that poly rC:rI is taken into cells more efficiently when complexed with DEAE-dextran. Accordingly in the practices of this invention the hydrophobic properties and the ionic or electron charge properties of the special dsRNA of this invention are important factors and capable of manipulation in the applicability of these materials to induce interferon production. It has been observed that such conditions or factors which promote the induction of interferon also lead to and promote the induction of other cellular or humoral components, such as lymphokines and cytokines. It is apparent, therefore, that the special nucleotides of this invention act as immune modulators and stimulators of the immune response other than simply being effective as inducers of interferon production. Superior agents for the above in accordance with the practices of this invention would include nucleotides wherein the Sig moiety incorporates biotin or streptavidin or avidin.

Poly rI:poly rC complexed poly L-lysine exhibits adjuvant properties and such properties are enhanced and improved in accordance with the practices of this invention when the poly rI and poly rC components are modified to include one or more of the special nucleotides in accordance with this invention.

The preparation of DNA probes in accordance with another aspect of this invention can be carried out in a manner which does not require the preparation or utilization of the special nucleotides described herein. For example, double-stranded DNA can be reacted with a carcinogen or alkylating agent. After the carcinogen has reacted with or alkylated the doubler-stranded DNA, the resulting modified DNA is melted to produce a DNA hybridizing probe containing the reaction product of the DNA and the carcinogen or alkylating agent. When thus-modified or reacted DNA is employed as a hybridizing probe, any resulting formed double helix or double-stranded DNA would be assayed or searched out by means of a double antibody technique. The primary antibody would be an anti-carcinogen and the secondary antibody would be horseradish-peroxidase conjugated anti-peroxidase antibody. The advantage of this technique is that it would be easy to label the double-stranded DNA. This special approach is indicated hereinabove in the examples accompanying the description of this invention and is generally applicable for the preparation of DNA probes from double-stranded or double helical DNA. However, this procedure is a disruptive procedure involving the modification of the double helical deoxyribonucleotide polymer or DNA.

In the description of the special nucleotides and modified DNA employed or developed in the practices of this invention, mention has been made of mono, oligo and polysaccharides. It is pointed out that derivatives of mono, oligo and polysaccharides are also useful in the preparation of the special nucleotides of this invention. For example, it is possible to modify individual sugar moieties employed in the make-up of the special nucleotides and employ the resulting modified sugar moieties to effect or carry out additional chemical reactions. Such modified mono, oligo and polysaccharide moieties, when employed as the Sig moiety in the preparation of the special nucleotides of this invention, provide an added versatility with respect to the detection of the nucleotides or other compounds containing such modified saccharides either as the sugar S (SM) or the Sig moiety thereof.

In another aspect of this invention the Sig moiety instead of being attached to a nucleotide could also be attached to proteins. Not only could such proteins be attached to nucleotides or polynucleotides but also such proteins could be identified per se whether attached to a nucleotide or polynucleotide or unattached. In accordance with the practices of this aspect of the invention, a suitable such protein adduct would have the formula,

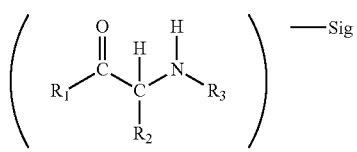

wherein $R_1$ is an OH or an amino acid or acids and $R_2$ is an amino acid side chain and $R_3$ is H or an amino acid or acids and Sig is attached to the $R_1$ and/or $R_2$ and/or $R_3$.

The invention claimed is:

1. A process for detecting a nucleic acid of interest in a sample, which process comprises:
   (A) providing a sample which may contain a nucleic acid of interest;
   (B) providing:
      (i) an oligo- or polynucleotide that comprises two segments, the first segment comprising a nucleotide sequence that is complementary to and capable of specifically hybridizing to and forming a hybrid with said nucleic acid of interest or a portion thereof, and the second segment comprising an operator sequence that is capable of binding to or complexing with a non-radioactively detectable protein; and
      (ii) a non-radioactively detectable protein which is non-radioactive and has a binding affinity to said operator sequence;
   (C) contacting a sample suspected of containing said nucleic acid of interest with said oligo- or polynucleotide (i) and said non-radioactively detectable protein (ii) to form a complex; and
   (D) detecting non-radioactively the presence of said non-radioactively detectable protein in said complex to detect said nucleic acid of interest.

2. The process according to claim 1, wherein the nucleic acid of interest comprises DNA, RNA or a DNA-RNA hybrid.

3. The process according to claim 1, wherein the nucleic acid of interest is double-stranded or single-stranded.

4. The process according to claim 1, wherein the nucleic acid of interest has been rendered single-stranded.

5. The process according to claim 1, wherein the nucleic acid of interest is derived from an organism.

6. The process according to claim 5, wherein the organism comprises prokaryotes or eukaryotes.

7. The process according to claim 5, wherein said organism bacteria, fungi, viruses, yeast or mammals.

8. The process according to claim 5, wherein said organism is living.

9. The process according to claim 1, wherein the sample is suspected of containing an etiological agent and the nucleic acid of interest is naturally associated with the etiological agent.

10. The process according to claim 9, wherein the sample is of human or animal origin and the etiological agent comprises bacteria, virus or fungi.

11. The process according to claim 1, wherein said nucleic acid of interest is derived from an organism comprising *Streptococcus pyrogenes, Neisseria meningitides, Staphylococcus aureus, Candida albicans, Pseudomonas aeruginosa, Neisseria gonorrhoeae*, or *Mycobacterium tuberculosis*.

12. The process according to claim 1, wherein said one or more oligo- or polynucleotides are derived from *Neisseria gonorrhoeae* sequences.

13. The process according to claim 1, wherein the sample comprises a bacterium suspected of containing a nucleic acid of interest which imparts resistance to an antibiotic and wherein the oligo- or polynucleotide comprises a polynucleotide complementary to the sequence of the bacterium which confers resistance to the antibiotic.

14. The process according to claim 13, wherein when said bacterium is *Streptococcus pyrogenes* or *Neisseria meningtidis*, said antibiotic is penicillin, wherein when said bacterium is *Staphylococcus aureus, Candida albicans, Pseudomonas aeruginosa, Streptococcus pyrogenes*, or *Neisseria gonorrhoea*, said antibiotic is a tetracycline, and wherein when said bacterium is *Mycobacterium tuberculosis*, said antibiotic is an aminoglycoside.

15. The process according to claim 14, wherein said bacterium is *Neisseria gonorrhoeae* and said antibiotic comprises penicillin, tetracycline, aminoglycoside or combinations thereof.

16. The process according to claim 1, wherein the sample is suspected of containing a nucleic acid of interest associated with a genetic disorder and wherein the oligo- or polynucleotide comprises a polynucleotide complementary to the nucleic acid associated with the genetic disorder.

17. The process according to claim 1, wherein said sample is suspected of containing a nucleic acid of interest associated with thalassemia and wherein the oligo- or polynucleotide comprises a polynucleotide complementary to the nucleic acid which is absent in the thalassemic subjects.

18. The process according to claim 1, wherein said process is utilized for chromosomal karyotyping which comprises contacting the sample with a series of the oligo- or polynucleotides (i) which are complementary to a series of known genetic sequences located on chromosomes.

19. The process according to claim 1, wherein said process is utilized to determine the number of copies of an individual chromosome in a sample.

20. The process according to claim 1, wherein said non-radioactive detectable protein comprises an antibody, a promoter, a repressor or an inducer.

21. The process according to claim 20, wherein said repressor comprises a lac repressor.

22. The process according to claim 20, wherein said operator sequence is covalently attached to said oligo- or polynucleotide.

23. The process according to claim 22, wherein said covalent attachment has been carried out by ligation.

24. The process according to claim 22, wherein said covalent attachment does not interfere substantially with the characteristic ability of said non-radioactively detectable protein to bind to any hybrid formed between said oligo- or polynucleotide and said nucleic acid of interest.

25. The process according to claim 22, wherein said covalent attachment does not interfere substantially with the characteristic ability of said non-radioactively detectable protein to be detected non-radioactively when bound to any hybrid formed between said oligo- or polynucleotide and said nucleic acid of interest.

26. The process according to claim 22, wherein said operator sequence is attached via a covalent attachment by an olefinic bond at the α-position relative to the point of attachment to said nucleotide structure or nucleotide analog structure (i), a $CH_2NH$— moiety, or both.

27. The process according to claim 26, wherein said covalent attachment comprises an allylamine group.

28. The process according to claim 26, wherein said covalent attachment comprises or includes an olefinic bond at the α-position relative to the point of attachment to the nucleotide, or any of the moieties

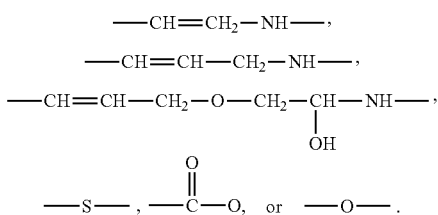

29. The process according to claim 22, wherein said covalent attachment comprises a glycosidic linkage moiety.

30. The process according to claim 22, wherein said operator sequence is covalently attached to any of the base, phosphate, or furanosyl moieties in said oligo- or polynucleotide.

31. The process according to claim 30, wherein said covalent attachment is through a linkage group.

32. The process according to claim 31, wherein said linkage group comprises an amine.

33. The process according to claim 32, wherein said amine comprises a primary amine.

34. The process according to claim 31, wherein said linkage group does not substantially interfere with the binding of said non-radioactively detectable protein to said operator sequence.

35. The process according to claim 1, wherein said non-radioactively detectable protein comprises a signalling component or indicator molecule.

36. The process according to claim 35, wherein said signalling component or indicator molecule comprises at least three carbon atoms.

37. The process according to claim 36, wherein said signalling component or indicator molecule comprises an aliphatic chemical moiety comprising at least three carbon atoms and at least one double bond.

38. The process according to claim 36, wherein said signalling component or indicator molecule comprises an aliphatic chemical moiety comprising at least four carbon atoms.

39. The process according to claim 36, wherein said signalling component or indicator molecule comprises an aromatic or cycloaliphatic group comprising at least five carbon atoms.

40. The process according to claim 39, wherein said aromatic or cycloaliphatic moiety is fluorescent or chemiluminescent.

41. The process according to claim 36, wherein said signalling component or indicator molecule comprises an aromatic or cycloaliphatic group comprising at least six carbon atoms.

42. The process according to claim 41, wherein said aromatic or cycloaliphatic moiety is fluorescent or chemiluminescent.

43. The process according to claim 36, wherein said signalling component or indicator molecule comprises a monosaccharide, polysaccharide or an oligosaccharide.

44. The process according to claim 35, wherein said signalling component or indicator molecule comprises biotin, iminobiotin, an electron dense component, a magnetic component, an enzyme, a hormone component, a metal-containing component, a fluorescent component, a chemiluminescent component, an antigen, a hapten, an antibody component a chelating component, or any combination of any of the foregoing.

45. The process according to claim 44, wherein said signalling component or indicator molecule comprises a chemiluminescent component.

46. The process according to claim 44, wherein said signalling component or indicator molecule comprises a chelating component.

47. The process according to claim 35, wherein said signalling component or indicator molecule comprises an aromatic structure.

48. The process according to claim 47, wherein said aromatic structure is heterocyclic.

49. The process according to claim 36, wherein said heterocyclic aromatic structure is fluorescent.

50. The process according to claim 49, wherein said fluorescent heterocyclic aromatic structure comprises fluorescein, rhodamine, dansyl or any combination of any of the foregoing.

51. The process according to claim 50, wherein said fluorescent heterocyclic aromatic structure comprises fluorescein.

52. The process according to claim 1, wherein said non-radioactively detectable protein is detectable by a fluorescent measurement, a chemiluminescent measurement, or a combination thereof.

53. The process according to claim 1, wherein said non-radioactively detectable protein is detectable when the oligo- or polynucleotide is contained in a double-stranded ribonucleic or deoxyribonucleic acid duplex formed with said nucleic acid of interest.

54. The process according to claim 1, wherein said nonradioactively detectable protein is detectable when it is attached to said oligo- or polynucleotide directly or through a linkage group.

55. The process according to claim 1, wherein said oligo- or polynucleotide is contacted with said sample suspected of containing the nucleic acid of interest prior to forming a complex with said non-radioactively detectable protein.

56. The process according to claim 1, wherein said detecting step is carried out directly.

57. The process according to claim 56, wherein said direct detection of the non-radioactively detectable protein is carried out on one or more signalling components or indicator molecules.

58. The process according to claim 57, wherein said direct detection step is carried out by a fluorogenic structure, a chemiluminescent structure, an enzyme, or an electron dense structure.

59. The process according to claim 1, wherein said detecting step is carried out indirectly.

60. The process according to claim 59, wherein said indirect detection is carried out by a means comprising an antibody, an antigen, a hapten, a receptor, a ligand, an enzyme, a structure capable of binding to an insoluble phase, or a combination of any of the foregoing.

61. The process according to claim 1, wherein said nonradioactively detectable protein is capable of being detected by means comprising an enzymatic measurement, a fluorescent measurement, a chemiluminescent measurement, a microscopic measurement or an electron density measurement.

62. The process according to claim 1, further comprising one or more washing steps.

63. A process for determining whether the number of copies of a particular chromosome in a cell is normal or abnormal, the process comprising: providing at least one cell; contacting said cell under hybridizing conditions with one or more clones or DNA fragments, or oligo- or polynucleotides derived from said clone or clones, wherein said clones or fragments or oligo- or polynucleotides are capable of hybridizing specifically to a locus or loci of said particular chromosome or a portion thereof, wherein said clones or fragments or oligo- or polynucleotides comprise one or more detectable non-radioactive modified or labeled nucleotides or one or more detectable non-radioactively modified or labeled nucleotide analogs, which nucleotide analogs can be attached to or coupled to or incorporated into DNA or RNA, and wherein said modified or labeled nucleotides or modified or labeled nucleotide analogs comprise:

(i) a nucleotide structure or nucleotide analog structure having the formula

PM-SM-BASE-Sig wherein
PM is a phosphate moiety,
SM is a furanosyl moiety,
BASE is a pyrimidine, a purine, or a 7-deazapurine base moiety; and
Sig is a detectable non-radioactive moiety,
wherein PM is covalently attached to SM, BASE is covalently attached to SM, and Sig is covalently attached to BASE at a position other than the C5 position when BASE is a pyrimidine moiety, at a position other than the C8 position when BASE is a purine moiety, and at a position other than the C7 position when BASE is a 7-deazapurine moiety;

(ii) a nucleotide structure or nucleotide analog structure having the formula

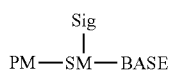

wherein
PM is a phosphate moiety,
SM is a furanosyl moiety,
BASE is a base moiety, and
Sig is a detectable non-radioactive moiety,
wherein PM is covalently attached to SM, BASE is covalently attached to SM, and Sig is covalently attached to SM directly or through a linkage group; or (iii) a nucleotide structure or nucleotide analog structure having the formula Sig-PM-SM-BASE wherein
PM is a phosphate moiety,
SM is a furanosyl moiety,
BASE is a base moiety, and
Sig is a detectable non-radioactive moiety,
wherein PM is covalently attached to SM, BASE is covalently attached to SM, and Sig is covalently attached to PM directly or through a linkage group, to permit specific hybridization of said clone or clones or DNA fragments or oligo- or polynucleotides to the locus or loci of said particular chromosome;
detecting non-radioactively any specifically hybridized clone or clones or DNA fragments or oligo- or polynucleotides, and determining the number of copies of said particular chromosome; and
comparing said determined number of copies of said particular chromosome with a number of copies of said particular chromosome determined for a normal cell containing said particular chromosome, and determining whether the number of copies of said particular chromosome in said cell is abnormal.

64. A process for identifying a chromosome of interest in a cell containing other chromosomes, the process comprising: providing at least one cell; providing a set of clones or DNA fragments, or oligo- or polynucleotides derived from said clone or clones, wherein said clones or fragments or oligo- or polynucleotides are specifically hybridizable to a locus or loci in said chromosome of interest, wherein said clones or fragments or said oligo- or polynucleotides comprise one or more detectable non-radioactive modified or labeled nucleotides or one or more detectable non-radioactively modified or labeled nucleotide analogs, which nucleotide analogs can be attached to or coupled to or incorporated into DNA or RNA, and wherein said modified or labeled nucleotides or modified or labeled nucleotide analogs comprise:

(i) a nucleotide structure or nucleotide analog structure having the formula

PM-SM-BASE-Sig wherein
PM is a phosphate moiety,
SM is a furanosyl moiety,
BASE is a pyrimidine, a purine, or a 7-deazapurine base moiety, and
Sig is a detectable non-radioactive moiety, wherein PM is covalently attached to SM, BASE is covalently attached to SM, and Sig is covalently attached to BASE at a position other than the C5 position when BASE is a pyrimidine moiety, at a position other than the C8 position when BASE is a purine moiety, and at a position other than the C7 position when BASE is a 7-deazapurine moiety;

(ii) a nucleotide structure or nucleotide analog structure having the formula

wherein
PM is a phosphate moiety,
SM is a furanosyl moiety,
BASE is a base moiety, and
Sig is a detectable non-radioactive moiety,
wherein PM is covalently attached to SM, BASE is covalently attached to SM, and Sig is covalently attached to SM directly or through a linkage group; or (iii) a nucleotide structure or nucleotide analog structure having the formula Sig-PM-SM-BASE wherein
PM is a phosphate moiety,
SM is a furanosyl moiety,
BASE is a base moiety, and
Sig is a detectable non-radioactive moiety,
wherein PM is covalently attached to SM, BASE is covalently attached to SM, and Sig is covalently attached to PM directly or through a linkage group;
fixing the chromosomes from or in said cell;
contacting said fixed chromosomes under hybridizing conditions with said set of clones or DNA fragments or oligo- or polynucleotides,
permitting specific hybridization of said set of clones or DNA fragments or oligo- or polynucleotides to said locus or loci in said chromosome of interest;
detecting non-radioactively any of said clones or DNA fragments or oligo- or polynucleotides which have specifically hybridized to said locus or loci in said chromosome of interest, and obtaining a pattern of hybridizations between said set of clones or DNA fragments or oligo- or polynucleotides and said chromosomes; and identifying said chromosome of interest by means of said hybridization pattern obtained.

65. A process for identifying a plurality or all of the chromosomes in a cell of interest, the process comprising: providing at least one cell; providing sets of clones or DNA fragments, or oligo- or polynucleotides derived from said clones, wherein said clones or fragments or said oligo- or polynucleotides are capable of hybridizing specifically to a locus or loci in a chromosome of said cell of interest, wherein each of said clones or DNA fragments or oligo- or polynucleotides in said sets are labeled with a different indicator moiety and each of said clones or DNA fragments or oligo- or polynucleotides comprises one or more detectable non-radioactive modified or labeled nucleotides or one or more detectable non-radioactive modified or labeled nucleotide analogs, which nucleotide analogs can be attached to or coupled to or incorporated into DNA or RNA, and wherein said modified or labeled nucleotides or modified or labeled nucleotide analogs comprise:

(i) a nucleotide structure or nucleotide analog structure having the formula

PM-SM-BASE-Sig wherein
PM is a phosphate moiety,
SM is a furanosyl moiety,
BASE is a pyrimidine, a purine, or a 7-deazapurine base moiety, and
Sig is a detectable non-radioactive moiety,
wherein PM is covalently attached to SM, BASE is covalently attached to SM, and Sig is covalently attached to BASE at a position other than the C5 position when BASE is a pyrimidine, at a position other than the C8 position when BASE is a purine, and at a position other than the C7 position when BASE is a 7-deazapurine;

(ii) a nucleotide structure or nucleotide analog structure having the formula

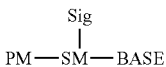

wherein
PM is a phosphate moiety,
SM is a furanosyl moiety,
BASE is a base moiety, and
Sig is a detectable non-radioactive moiety,
wherein PM is covalently attached to SM, BASE is covalently attached to SM, and Sig is covalently attached to SM directly or through a linkage group; or (iii) a nucleotide structure or nucleotide analog structure having the formula Sig-PM-SM-BASE wherein
PM is a phosphate moiety,
SM is a furanosyl moiety,
BASE is a base moiety and
Sig is a detectable non-radioactive moiety,
wherein PM is covalently attached to SM, BASE is covalently attached to SM, and Sig is covalently attached to PM directly or through a linkage group;

fixing the chromosomes from or in said cell;

contacting said fixed chromosomes under hybridizing conditions with said sets of clones or DNA fragments or oligo- or polynucleotides, and permitting specific hybridization of said sets of clones or DNA fragments or oligo- or polynucleotides to the locus or loci in said chromosomes; and detecting non-radioactively any of said different indicator moieties in said sets of clones or DNA fragments or oligo- or polynucleotides which have specifically hybridized to the locus or loci in said chromosomes, and identifying any one of the chromosomes in said cell of interest.

66. The process according to claim 65, wherein each of said set of clones or DNA fragments or oligo- or polynucleotides is labeled with the same indicator molecule.

67. A process for determining the number of chromosomes in an interphase cell of interest, the process comprising:

providing at least one interphase cell;

providing sets of clones or DNA fragments or oligo- or polynucleotides derived from said clones, wherein said set of clones or DNA fragments or oligo- or polynucleotides are specifically complementary to or specifically hybridizable with at least one locus or loci in a chromosome of said interphase cell of interest and each of said clones or DNA fragments or oligo- or polynucleotides in said sets comprises one or more detectable non-radioactive modified or labeled nucleotides or detectable non-radioactively modified or labeled nucleotide analogs, which nucleotide analogs can be attached to or coupled to or incorporated into DNA or RNA, and wherein said modified or labeled nucleotides or modified or labeled nucleotide analogs comprise one or more of:

(i) a nucleotide structure or nucleotide analog structure having the formula

PM-SM-BASE-Sig wherein
PM is a phosphate moiety,
SM is a furanosyl moiety,
BASE is a pyrimidine, a purine, or a 7-deazapurine base moiety, and
Sig is a detectable non-radioactive moiety,
wherein PM is covalently attached to SM, BASE is covalently attached to SM, and Sig is covalently attached to BASE at a position other than the C5 position when BASE is a pyrimidine moiety, at a position other than the C8 position when BASE is a purine, and at a position other than the C7 position when BASE is a 7-deazapurine;

(ii) a nucleotide structure or nucleotide analog structure having the formula

wherein
PM is a phosphate moiety,
SM is a furanosyl moiety,
BASE is a pyrimidine, a purine or a 7-deazapurine base moiety, and
Sig is a detectable non-radioactive moiety,
wherein PM is covalently attached to SM, BASE is covalently attached to SM, and Sig is covalently attached to SM directly or through a linkage group; or (iii) a nucleotide structure or nucleotide analog structure having the formula Sig-PM-SM-BASE wherein
PM is a phosphate moiety,
SM is a furanosyl moiety,
BASE is a pyrimidine, a purine or a 7-deazapurine base moiety, and
Sig is a detectable non-radioactive moiety,
wherein PM is covalently attached to the SM, BASE is covalently attached to SM, and Sig is covalently attached to PM directly or through a linkage group;
contacting said interphase cell under hybridizing conditions with said sets of clones or DNA fragments or oligo- or polynucleotides,
permitting specific hybridization of said sets of clones or DNA fragments or oligo- or polynucleotides to any of the locus or loci in said chromosomes;
detecting non-radioactively any of said sets of clones or DNA fragments or oligo- or polynucleotides specifically hybridized to the locus or loci in said chromosomes, to obtain a pattern of generated signals; and
comparing each generated signal with other generated signals in said pattern, and determining the number of chromosomes in said interphase cell of interest.

68. The process according to claim 67, wherein each of said sets of clones or DNA fragments or oligo- or polynucleotides is labeled with the same indicator molecule.

69. The process according to claim 67, wherein each of said sets of clones or DNA fragments or oligo- or polynucleotides is labeled with a different indicator molecule.

70. The process according to claim 67, wherein said detecting and determining step is carried out by a means comprising manual means or automatic means.

71. The process according to claim 70, wherein said manual means comprises visualization.

72. The process according to claim 70, wherein said automatic means comprises computerized automatic karyotyping.

73. The process according to any of claim 63, 64, 65 or 67, wherein said nucleotide analog has been attached terminally to DNA or RNA by means of an enzyme.

74. The process according to claim 73, wherein said enzyme comprises terminal transferase.

75. The process according to any of claim 63, 64, 65 or 67, wherein said nucleotide analog has been coupled to DNA or RNA by a coupling means comprising chemical coupling or enzymatic coupling.

76. The process according to claim 75, wherein said chemical coupling has been carried out by a chemical coupling means comprising carbodiimide or formaldehyde.

77. The process according to claim 75, wherein said enzymatic coupling has been carried out by an enzymatic coupling means comprising DNA ligase or RNA ligase.

78. The process according to any of claim 63, 64, 65 or 67, wherein said incorporation comprises nick translation.

79. The process according to any of claim 63, 64, 65 or 67, wherein said incorporation is carried out by means of a polymerizing enzyme.

80. The process according to claim 79, wherein said polymerizing enzyme comprises a polymerase.

81. The process according to claim 80, wherein said polymerase comprises DNA polymerase or RNA polymerase.

82. The process according to any of claim 63, 64, 65 or 67, wherein PM comprises a mono-phosphate, a di-phosphate, a tri-phosphate or a tetraphosphate.

83. The process according to any of claim 63, 64, 65 or 67, wherein any of said nucleotide structures or nucleotide analog structures (i), (ii) or (iii) comprises nucleoside mono-, di- or tri-phosphate.

84. The process according to claim 63, 64, 65 or 67, wherein SM comprises ribose, 2'-deoxyribose, 3'-deoxyribose or 2',3'-dideoxyribose.

85. The process according to any of claim 63, 64, 65 or 67, wherein BASE in any of said nucleotide structures or nucleotide analog structures (i), (ii) or (iii) comprises a 7-deazapurine.

86. The process according to any of claim 63, 64, 65 or 67, wherein Sig in said nucleotide structure or nucleotide analog structure (i) is covalently attached to BASE the C2 position, the N3 position, the C6 position, or combinations thereof when BASE is a pyrimidine, or is covalently attached to BASE the N1 position, the C2 position, the N3 position, the C6 position, the N7 position, or combinations thereof when BASE is a purine.

87. The process according to any of claim 63, 64, 65 or 67, wherein Sig in said nucleotide structure or nucleotide analog structure (i) is covalently attached to BASE at a position comprising the $N^4$ position when said pyrimidine comprises cytosine, the $N^2$ position when said purine comprises adenine or deazaadenine, the $N^6$ position when said purine comprises guanine or deazaguanine, or combinations thereof.

88. The process according to claim 63, 64, 65 or 67, wherein in said nucleotide structure or nucleotide analog structure (ii), PM is attached to SM at the 2', 3', 5' positions, or any combination thereof, and BASE is attached to the 1' position of SM from the N1 position when BASE is a pyrimidine or the N9 position when BASE is a purine or 7-deazapurine, and Sig is covalently attached to SM directly or through a linkage group and such covalent attachment does not substantially interfere with double helix formation or nucleic acid hybridization.

89. The process according to claim 63, 64, 65 or 67, wherein in said nucleotide structure or nucleotide analog structure (iii), PM is attached to SM at the 2', 3', 5' positions, or any combination thereof, and BASE is attached to the 1' position of SM from the N1 position when BASE is a pyrimidine or the N9 position when BASE is a purine or 7-deazapurine, and Sig is covalently attached to PM directly or through a linkage group and such covalent attachment does not substantially interfere with double helix formation or nucleic acid hybridization.

90. The process according to any of claim 63, 64, 65 or 67, wherein said covalent attachment in nucleotide or nucleotide analog structure (iii) comprises

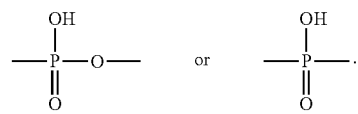

91. The process according to any of claim 63, 64, 65 or 67, wherein PM comprises a mono-, di or tri-phosphate, and wherein in said nucleotide structure or nucleotide analog structure (iii), Sig is covalently attached to PM through a phosphorus or phosphate oxygen.

92. The process according to any of claim 63, 64, 65 or 67, wherein said covalent attachment in any of said nucleotide structures or nucleotide analog structures (i), (ii) or (iii) does not interfere substantially with the characteristic ability of Sig to form a detectable non-radioactive signal.

93. The process according to any of claim 63, 64, 65 or 67, wherein in any of said nucleotide structures or nucleotide analog structures (i), (ii) or (iii) said Sig is covalently attached to BASE, SM or PM through a linkage group.

94. The process according to claim 93, wherein, in nucleotide structure or nucleotide analog structure (i), said linkage group contains an amine.

95. The process according to claim 93, wherein said linkage group does not substantially interfere with formation of the signalling moiety or detection of the detectable non-radioactive signal.

96. The process according to claim 94, wherein said amine comprises a primary amine.

97. The process according to any of claim 63, 64, 65 or 67, wherein Sig comprises at least three carbon atoms.

98. The process according to any of claim 63, 64, 65 or 67, wherein said Sig detectable non-radioactive moiety comprises an aliphatic chemical moiety comprising at least three carbon atoms and at least one double bond.

99. The process according to any of claim 63, 64, 65 or 67, wherein said Sig detectable non-radioactive moiety comprises an aliphatic chemical moiety comprising at least four carbon atoms.

100. The process according to any of claim 63, 64, 65 or 67, wherein said Sig detectable non-radioactive moiety comprises an aromatic or cycloaliphatic group comprising at least five carbon atoms.

101. The process according to claim 100, wherein said aromatic or cycloaliphatic moiety is fluorescent or chemiluminescent.

102. The process according to any of claim 63, 64, 65 or 67, wherein said Sig detectable non-radioactive moiety comprises an aromatic or cycloaliphatic group comprising at least six carbon atoms.

103. The process according to claim 102, wherein said aromatic or cycloaliphatic moiety is fluorescent or chemiluminescent.

104. The process according to any of claim 63, 64, 65 or 67, wherein Sig comprises a monosaccharide, polysaccharide or an oligosaccharide.

105. The process according to any of claim 63, 64, 65 or 67, wherein Sig comprises biotin, iminobiotin, an electron dense component, a magnetic component, an enzyme, a hormone component, a metal-containing component, a fluorescent component, a chemiluminescent component, an antigen, a hapten, an antibody component, a chelating component, or any combination of any of the foregoing.

106. The process according to claim 105, wherein said electron dense component comprises ferritin.

107. The process according to claim 105, wherein said magnetic component comprises magnetic oxide or magnetic iron oxide.

108. The process according to claim 105, wherein said magnetic component comprises magnetic beads.

109. The process according to claim 105, wherein said enzyme comprises alkaline phosphatase, acid phosphatase, galactosidase, ribonuclease, glucose oxidase and peroxidase, or a combination thereof.

110. The process according to claim 105, wherein said metal-containing component is catalytic.

111. The process according to claim 105, wherein Sig comprises a fluorescent component.

112. The process according to claim 105, wherein said fluorescent component comprises fluorescein, rhodamine or dansyl.

113. The process according to claim 112, wherein said fluorescent component comprises fluorescein.

114. The process according to claim 105, wherein Sig comprises an antigenic or hapten component capable of completing with an antibody specific to the component.

115. The process according to any of claim 63, 64, 65 or 67, wherein Sig comprises a sugar residue and the sugar residue is complexed with or attached to a sugar binding protein or a polysaccharide binding protein.

116. The process according to claim 115, wherein the binding protein comprises a lectin.

117. The process according to claim 116, wherein the lectin comprises concanavalin A.

118. The process according to claim 116, wherein said lectin is conjugated to ferritin.

119. The process according to any of claim 63, 64, 65 or 67, wherein Sig is a non-radioactively detectable indicator molecule.

120. The process according to claim 119, wherein said indicator molecule comprises an aromatic structure.

121. The process according to claim 120, wherein said aromatic structure is heterocyclic.

122. The process according to claim 121, wherein said heterocyclic aromatic structure is fluorescent.

123. The process according to claim 122, wherein the fluorescent heterocyclic aromatic structure comprises fluorescein, rhodamine, dansyl, or a combination of any of the foregoing.

124. The process according to claim 123, wherein said fluorescent heterocyclic aromatic structure comprises fluorescein.

125. The process according to any of claim 63, 64, 65 or 67, wherein said Sig detectable non-radioactive moiety is a non-radioactively detectable indicator molecule.

126. The process according to claim 125, wherein said indicator molecule comprises a fluorescent component, a chemiluminescent component, a chelating component, or a combination of any of the foregoing.

127. The process according to any of claim 63, 64, 65 or 67, wherein any of said nucleotide structures or nucleotide analog structures (i), (ii) and (iii) are detectable by a means comprising a fluorescent measurement, a chemiluminescent measurement, or a combination thereof.

128. The process according to any of claim 63, 64, 65 or 67, wherein Sig is detectable when the oligo- or polynucleotide is contained in a double-stranded ribonucleic or deoxyribonucleic acid duplex.

129. The process according to any of claim 63, 64, 65 or 67, wherein Sig is detectable when it is attached to the nucleotide directly or through a linkage group.

130. The process according to claim 129, wherein said linkage group does not interfere substantially with the characteristic ability of Sig to form a detectable signal.

131. The process according to any of claim 63, 64, 65 or 67, wherein Sig in said nucleotide structure or nucleotide analog structure (iii) is covalently attached to PM via the chemical linkage

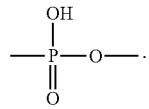

132. The process according to any of claim 63, 64, 65 or 67, wherein Sig in said nucleotide structure or nucleotide analog structure (iii) is covalently attached to PM via a chemical linkage.

133. The process according to any of claim 63, 64, 65 or 67, wherein the oligo- or polynucleotide is terminally ligated or attached to a polypeptide.

134. The process according to claim 133, wherein the polypeptide comprises a polylysine.

135. The process according to claim 133, wherein the polypeptide comprises avidin, streptavidin or anti-Sig immunoglobulin.

136. The process according to any of claim 63, 64, 65 or 67, further comprising contacting the sample with a polypeptide capable of forming a complex with Sig and a moiety which can be detected when the complex is formed.

137. The process according to claim 136, wherein the polypeptide comprises a polylysine.

138. The process according to claim 136, wherein the polypeptide comprises avidin, streptavidin or anti-Sig immunoglobulin.

139. The process according to claim 136, wherein Sig comprises a ligand and the polypeptide comprises an antibody thereto.

140. The process according to claim 136, wherein the moiety which can be detected when the complex is formed comprises biotin, iminobiotin, an electron dense component, a magnetic component, an enzyme, a hormone component, a metal-containing component, a fluorescent component, a chemiluminescent component, an antigen, a hapten, an antibody component, a chelating component, or any combination of any of the foregoing.

141. The process according to any of claim 63, 64, 65 or 67, wherein said detecting step is carried out directly.

142. The process according to claim 141, wherein said direct detection is carried out on one or more non-radioactively detectable indicator molecules.

143. The process according to claim 142, wherein said non-radioactively detectable indicator molecules comprise fluorescently labeled nucleotides.

144. The process according to claim 143, wherein said fluorescently labeled nucleotides comprise fluorescent DNA.

145. The process according to any of claim 63, 64, 65 or 67, wherein said detecting step is carried out by means of a directly detectable signal provided by said Sig detectable non-radioactive moiety.

146. The process according to claim 145, wherein said detecting step is carried out by a fluorogenic structure, a chemiluminescent structure or an electron dense structure.

147. The process according to claim 145, wherein said detecting step the directly detectable non-radioactive signal is provided by an enzyme.

148. The process according to any of claim 63, 64, 65 or 67, wherein said detecting step is carried out by means of a indirectly detectable signal provided by said Sig detectable non-radioactive moiety.

149. The process according to claim 148, wherein said detecting step the indirectly detectable non-radioactive signal is provided by an antibody, an antigen, a hapten, a receptor, a ligand or an enzyme.

150. The process according to any of claim 63, 64, 65 or 67, wherein said Sig detectable non-radioactive moiety is capable of being detected by an enzymatic measurement, a fluorescent measurement, a chemiluminescent measurement, a microscopic measurement or an electron density measurement.

151. The process according to any of claim 63, 64, 65 or 67, further comprising one or more washing steps.

152. The process according to claim 63, 64, 65 or 67, wherein said one or more clones or DNA fragments or oligo- or polynucleotides derived from clone or clones are derived from said particular chromosome or said chromosome of interest or said chromosome in said interphase cell of interest.

153. The process according to any of claims 63, 64 or 65, wherein said detecting step is carried out by a means comprising manual means or automatic means.

154. The process according to claim 153, wherein said manual means comprises visualization.

155. The process according to claim 153, wherein said automatic means comprises computerized automatic karyotyping.

156. A process for detecting a nucleic acid of interest in a sample, which process comprises:
(a) providing a sample which may comprise a nucleic acid of interest;
(b) providing a metal or metal ion;
(c) specifically hybridizing said nucleic acid of interest in the sample with one or more oligo- or polynucleotides, each such oligo- or polynucleotide being complementary to or capable of hybridizing with said nucleic acid of interest or a portion thereof, wherein said oligo- or polynucleotides comprise one or more detectable non-radioactive modified or labeled nucleotides or detectable non-radioactive modified or labeled nucleotide analogs, which nucleotide analogs can be attached to or coupled to or incorporated into DNA or RNA, and wherein said modified or labeled nucleotides or modified or labeled nucleotide analogs comprise a nucleotide structure or nucleotide analog structure comprising:
(i) a nucleotide structure or nucleotide analog structure having the formula PM-SM-BASE-Sig wherein
PM is a phosphate moiety,
SM is a furanosyl moiety,
BASE is a pyrimidine, a purine or a 7-deazapurine base moiety; and
Sig is a signalling moiety comprising a chelating structure or component capable of chelating said metal or metal ion and providing a detectable signal, wherein Sig comprises at least three carbon atoms, wherein PM is covalently attached to SM, BASE is covalently attached to SM, and Sig is covalently attached to BASE directly or through a linkage group at a position other than the C5 position when BASE is a pyrimidine moiety, at a position other than the C8 position when BASE is a purine moiety and at a position other than the C7 position when BASE is a 7-deazapurine moiety, and such covalent attachment does not substantially interfere with double helix formation or nucleic acid hybridization;
(ii) a nucleotide structure or nucleotide analog structure having the formula

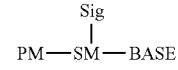

wherein
PM is a phosphate moiety,
SM is a furanosyl moiety,
BASE is a base moiety, and
Sig is a signalling moiety comprising a chelating structure or component capable of providing chelating said metal or metal ion and a detectable signal, wherein Sig comprises at least three carbon atoms, wherein PM is covalently attached to SM, BASE is covalently attached to SM, and Sig is covalently attached to SM directly or through a linkage group and such covalent attachment does not substantially interfere with double helix formation or nucleic acid hybridization; or (iii) a nucleotide structure or nucleotide analog structure having the formula Sig-PM-SM-BASE wherein
PM is a phosphate moiety,
SM is a furanosyl moiety,
BASE is a base moiety, and
Sig is a signalling moiety comprising a chelating structure or components capable of chelating said metal or metal ion and providing a detectable signal, wherein Sig comprises at least three carbon atoms, wherein PM is covalently attached to SM, BASE is covalently attached to SM, and Sig is covalently attached to PM directly or through a linkage group, and such covalent attachment does not substantially interfere with double helix formation or nucleic acid hybridization;

provided that when said nucleotide or nucleotide analog structure (iii) is attached to an oligoribonucleotide or a polyribonucleotide, and provided that when Sig is attached through a chemical linkage to a terminal PM at the 3' position of a terminal ribonucleotide, said chemical linkage is not obtained through a 2', 3' vicinal oxidation of a 3' terminal ribonucleotide previously attached to said oligoribonucleotide or polyribonucleotide; and (d) detecting the presence of Sig in any of the oligo- or polynucleotides which have hybridized to said nucleic acid of interest by means of said metal or metal ion chelated by said chelating structure or chelating components.

157. The process of claim 156, wherein in said specific hybridizing step, the chelating structure or chelating components provide a detectable signal that is radioactive, fluorogenic, fluorescent, chemiluminescent, electron dense or magnetic.

158. A process for detecting a nucleic acid of interest in a sample, which process comprises:
(A) providing:
  (i) an oligo- or polynucleotide having two segments:
    (a) a first segment complementary to and capable of hybridizing to a portion of said nucleic acid of interest; and
    (b) a second segment comprising at least one protein binding sequence; and
  (ii) a metal or metal ion;
  (iii) a detectable protein capable of binding to said protein binding sequence and comprising a chelating structure or chelating component capable of chelating said metal or metal ion and providing a detectable signal;

(B) contacting a sample suspected of containing said nucleic acid of interest with said oligo- or polynucleotide and said detectable protein (ii) to form a complex;
(C) detecting the presence of said protein in said complex and said nucleic acid of interest by means of said metal or metal ion chelated by said chelating structure or chelating component.

159. A process for determining whether the number of copies of a particular chromosome in a cell is normal or abnormal, the process comprising:
providing a cell;
providing a metal or metal ion;
contacting said cell under hybridizing conditions with one or more clones or DNA fragments, or oligo- or polynucleotides derived from said clone or clones, wherein said clones or fragments or oligo- or polynucleotides are capable of hybridizing specifically to a locus or loci of said particular chromosome or a portion thereof, wherein said clones or fragments or oligo- or polynucleotides comprise one or more detectable non-radioactive modified or labeled nucleotides or detectable non-radioactive modified or labeled nucleotide analogs, which nucleotide analogs can be attached to or coupled to or incorporated into DNA or RNA, and wherein said modified or labeled nucleotides or modified or labeled nucleotide analogs comprise a nucleotide structure or nucleotide analog structure comprising:

(i) a nucleotide structure or nucleotide analog structure having the formula

PM-SM-BASE-Sig wherein
PM is a phosphate moiety,
SM is a furanosyl moiety,
BASE is a pyrimidine, a purine, or a 7-deazapurine base moiety, and
Sig is a signalling moiety comprising a chelating structure or chelating component capable of chelating said metal or metal ion and providing a detectable signal, wherein PM is covalently attached to the SM, BASE is covalently attached to SM, and Sig is covalently attached to BASE at a position other than the C5 position when BASE is a pyrimidine moiety, at a position other than the C8 position when BASE is a purine moiety, and at a position other than the C7 position when BASE is a 7-deazapurine moiety;

(ii) a nucleotide structure or nucleotide analog structure having the formula

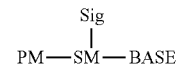

wherein
PM is a phosphate moiety,
SM is a furanosyl moiety,
BASE is a base moiety, and
Sig is a signalling moiety comprising a chelating structure or chelating component capable of chelating said metal or metal ion and providing a detectable signal, wherein PM is covalently attached to SM, BASE is covalently attached to SM, and Sig is covalently attached to SM directly or through a linkage group; or (iii) a nucleotide structure or nucleotide analog structure having the formula Sig-PM-SM-BASE wherein
> PM is a phosphate moiety,
> SM is a furanosyl moiety,
> BASE is a base moiety, and
> Sig is a signalling moiety comprising a chelating structure or chelating component capable of chelating said metal or metal ion and providing a detectable signal, wherein PM is covalently attached to SM, BASE is covalently attached to SM, and Sig is covalently attached to PM directly or through a linkage group, to permit specific hybridization of said clone or clones or DNA fragments or oligo- or polynucleotides to the locus or loci of said particular chromosome;

detecting the signal generated by said specifically hybridized clone or clones or DNA fragments or oligo- or polynucleotides by means of said metal or metal ion chelated by said chelating structure or chelating component, and determining the number of copies of said particular chromosome;

comparing said determined number of copies of said particular chromosome with a number of copies of said particular chromosome determined for a normal cell containing said particular chromosome; and determining whether the number of copies of said particular chromosome in said cell is abnormal.

160. The process of claim 159, wherein in said contacting step, the chelating structure or chelating components provide a detectable signal that is radioactive, fluorogenic, fluorescent, chemiluminescent, electron dense or magnetic.

161. A process for identifying a chromosome of interest in a cell containing other chromosomes, the process comprising:
   providing a cell;
   providing a metal or metal ion;
   providing a set of clones or DNA fragments, or oligo- or polynucleotides derived from said clone or clones, wherein said clones or fragments or oligo- or polynucleotides are specifically hybridizable to a locus or loci in said chromosome of interest, wherein said clones or fragments or oligo- or polynucleotides comprise one or more detectable modified or labeled nucleotides or detectable modified or labeled nucleotide analogs, which nucleotide analogs can be attached to or coupled to or incorporated into DNA or RNA, and wherein said modified or labeled nucleotides or modified or labeled nucleotide analogs comprise a nucleotide structure or nucleotide analog structure comprising:
   (i) a nucleotide structure or nucleotide analog structure having the formula PM-SM-BASE-Sig wherein
> PM is a phosphate moiety,
> SM is a furanosyl moiety,
> BASE is a pyrimidine, a purine, or a 7-deazapurine base moiety, and
> Sig is a signalling moiety comprising a chelating structure or chelating component capable of chelating said metal or metal ion and providing a detectable signal, wherein Sig comprises at least three carbon atoms, wherein PM is covalently attached to SM, BASE is covalently attached to SM, and Sig is covalently attached to BASE at a position other than the C5 position when BASE is a pyrimidine moiety, at a position other than the C8 position when BASE is a purine moiety, and at a position other than the C7 position when BASE is a 7-deazapurine moiety;

(ii) a nucleotide structure or nucleotide analog structure having the formula

wherein
> PM is a phosphate moiety,
> SM is a furanosyl moiety,
> BASE is a base moiety, and
> Sig is a signalling moiety comprising a chelating structure or chelating component capable of chelating said metal or metal ion and providing a detectable signal, wherein Sig comprises at least three carbon atoms, wherein PM is covalently attached to SM, BASE is covalently attached to SM, and Sig is covalently attached to SM directly or through a linkage group; or (iii) a nucleotide structure or nucleotide analog structure having the formula Sig-PM-SM-BASE wherein
> PM is a phosphate moiety,
> SM is a furanosyl moiety,
> BASE is a base moiety, and
> Sig is a signalling moiety comprising a chelating structure or chelating component capable of chelating said metal or metal ion and providing a detectable signal, wherein Sig comprises at least three carbon atoms, wherein PM is covalently attached to SM, BASE is covalently attached to SM, and Sig is covalently attached to PM directly or through a linkage group;

fixing the chromosomes from or in said cell;
contacting said fixed chromosomes under hybridizing conditions with said set of clones or DNA fragments or oligo- or polynucleotides, permitting specific hybridization of said set of clones or DNA fragments or oligo- or polynucleotides to said locus or loci in said chromosome of interest;
detecting by means of said metal or metal ion chelated by said chelating structure or chelating component any signal generated by each of said clones or DNA fragments or oligo- or polynucleotides which have specifically hybridized to said locus or loci in said chromosome of interest, and obtaining a pattern of hybridizations between said set of clones or DNA fragments or oligo- or polynucleotides and said chromosomes; and
identifying said chromosome of interest by means of said hybridization pattern obtained.

162. A process for identifying a plurality or all of the chromosomes in a cell of interest, the process comprising:
   providing a cell of interest;
   providing a metal or metal ion;
   providing sets of clones or DNA fragments, or oligo- or polynucleotides derived from said clones, wherein each of said set of clones or DNA fragments or oligo- or polynucleotides are specifically hybridizable to a locus or loci in a chromosome of said cell of interest, wherein each of said clones or DNA fragments or oligo- or polynucleotides comprise one or more detectable modified or labeled nucleotides or detectable modified or labeled nucleotide analogs capable of detection, which nucleotide analogs can be attached to or coupled to or incorporated into DNA or RNA and wherein each set comprises a different indicator molecule, and wherein said modified or labeled nucleotide or modified or labeled nucleotide analogs comprise a nucleotide structure or nucleotide analog structure comprising:
(i) a nucleotide structure or nucleotide analog structure having the formula PM-SM-BASE-Sig wherein
PM is a phosphate moiety,
SM is a furanosyl moiety,
BASE is a pyrimidine, a purine, or a 7-deazapurine base moiety, and
Sig is a signalling moiety comprising a chelating structure or chelating component capable of chelating said metal or metal ion and providing a detectable signal, wherein Sig comprises at least three carbon atoms, wherein PM is covalently attached to SM, BASE is covalently attached to SM, and Sig is covalently attached to BASE at a position other than the C5 position when BASE is a pyrimidine, at a position other than the C8 position when BASE is a purine, and at a position other than the C7 position when BASE is a 7-deazapurine;
(ii) a nucleotide structure or nucleotide analog structure having the formula

wherein
PM is a phosphate moiety,
SM is a furanosyl moiety,
BASE is a base moiety, and
Sig is a signalling moiety comprising a chelating structure or chelating component capable of chelating said metal or metal ion and providing a detectable signal, wherein Sig comprises at least three carbon atoms, wherein PM is covalently attached to SM, BASE is covalently attached to SM, and Sig is covalently attached to SM directly or through a linkage group; and
(iii) a nucleotide structure or nucleotide analog structure having the formula Sig-PM-SM-BASE wherein
PM is a phosphate moiety,
SM is a furanosyl moiety,
BASE is a base moiety, and
Sig is a signalling moiety comprising a chelating structure or chelating component capable of chelating said metal or metal ion and providing a detectable signal, wherein Sig comprises at least three carbon atoms, wherein PM is covalently attached to SM, BASE is covalently attached to SM, and Sig is covalently attached to PM directly or through a linkage group;
fixing the chromosomes from or in said cell;
contacting said fixed chromosomes under hybridizing conditions with said sets of clones or DNA fragments or oligo- or polynucleotides, and permitting specific hybridization of said sets of clones or DNA fragments or oligo- or polynucleotides to the locus or loci in said chromosomes; and
detecting by means of said metal or metal ion chelated by said chelating structure or chelating component any signal generated by each of said different indicator moieties in said sets of clones or DNA fragments or oligo- or polynucleotides which have specifically hybridized to the locus or loci in said chromosomes, and identifying a plurality or all of the chromosomes in said cell of interest.

163. A process for determining the number of chromosomes in an interphase cell of interest, the process comprising:
providing an interphase cell of interest;
providing a metal or metal ion;
providing sets of clones or DNA fragments, or oligo- or polynucleotides derived from said clones, wherein each of said set of clones or DNA fragments or oligo- or polynucleotides are specifically complementary to or specifically hybridizable with at least one locus or loci in a chromosome of said interphase cell of interest, wherein each of said clones or DNA fragments or oligo- or polynucleotides in said sets comprise one or more detectable modified or labeled nucleotides or detectable modified or labeled nucleotide analogs, which nucleotide analogs can be attached to or coupled to or incorporated into DNA or RNA, and wherein said modified or labeled nucleotide or modified or labeled nucleotide analog comprise a nucleotide structure or nucleotide analog structure comprising:
(i) a nucleotide structure or nucleotide analog structure having the formula PM-SM-BASE-Sig wherein
PM is a phosphate moiety,
SM is a furanosyl moiety,
BASE is a pyrimidine, a purine, or a 7-deazapurine base moiety, and
Sig is a signalling moiety comprising a chelating structure or chelating component capable of chelating said metal or metal ion and providing a detectable signal, wherein PM is covalently attached to SM, BASE is covalently attached to SM, and Sig is covalently attached to BASE at a position other than the C5 position when BASE is a, pyrimidine moiety, at a position other than the C8 position when BASE is a purine, and at a position other than the C7 position when BASE is a 7-deazapurine;
(ii) a nucleotide structure or nucleotide analog structure having the formula

wherein
PM is a phosphate moiety,
SM is a furanosyl moiety,
BASE is a pyrimidine, a purine or a 7-deazapurine base moiety, and
Sig is a signalling moiety comprising a chelating structure or chelating component capable of chelating said metal or metal ion and providing a detectable signal, wherein PM is covalently attached to SM, BASE is covalently attached to SM, and Sig is covalently attached to SM directly or through a linkage group; or
(iii) a nucleotide structure or nucleotide analog structure having the formula Sig-PM-SM-BASE wherein
PM is a phosphate moiety,
SM is a furanosyl moiety,
BASE is a pyrimidine, a purine or a 7-deazapurine base moiety, and
Sig is a signalling moiety comprising a chelating structure or chelating component capable of chelating said metal or metal ion and providing a detectable signal, wherein PM is covalently attached to the SM, BASE is covalently attached to SM, and Sig is covalently attached to PM directly or through a linkage group;

contacting said interphase cell under hybridizing conditions with said sets of clones or DNA fragments or oligo- or polynucleotides, and permitting specific hybridization of said sets of clones or DNA fragments or oligo- or polynucleotides to any of the locus or loci in said chromosomes; and detecting by means of said metal or metal ion chelated by said chelating structure or chelating component any signals generated by each of said sets of clones or DNA fragments or oligo- or polynucleotides specifically hybridized to the locus or loci in said chromosomes, to obtain a pattern of generated signals; and comparing each generated signal with other generate signals in said pattern, and determining the number of chromosomes in said interphase cell of interest.

164. A process for preparing a labeled oligo- or polynucleotide of interest, comprising:
(A) providing a metal or metal ion;
(B) providing:
  (1) one or more detectable chemically modified or labeled nucleotides or detectable chemically modified or labeled nucleotide analogs, which nucleotide analogs can be attached to or coupled to or incorporated into DNA or RNA or an oligo- or polynucleotide of interest, alone or in conjunction with one or more other modified or unmodified nucleic acids selected from the group consisting of nucleotides, oligonucleotides and polynucleotides, wherein said other modified or unmodified nucleic acids are capable of incorporating into an oligo- or polynucleotide of interest, and wherein said modified or labeled nucleotides or nucleotide analogs comprise one or more signalling moieties comprising a chelating structure or chelating component capable of chelating a metal or metal ion and providing a detectable signal,
  (2) an oligo- or polynucleotide comprising one or more of said modified or labeled nucleotides or modified or labeled nucleotide analogs (1), alone or in conjunction with one or more other modified or unmodified nucleic acids selected from the group consisting of nucleotides, oligonucleotides and polynucleotides, or
  (3) both (1) and (2),
wherein said modified or labeled nucleotides or modified or labeled nucleotide analogs (1) are modified on the furanosyl moiety, the phosphate moiety, the base moiety or any combination thereof, and wherein the modified or labeled nucleotides or modified or labeled nucleotide analogs comprise a nucleotide structure or nucleotide analog structure comprising:

PM-SM-BASE-Sig     (i)

wherein
PM is a phosphate moiety,
SM is a furanosyl moiety,
BASE is a pyrimidine, a purine or a 7-deazapurine base moiety, and Sig is a signalling moiety comprising a chelating structure or chelating component capable of chelating said metal or metal ion and providing a detectable signal, wherein Sig comprises at least three carbon atoms, and wherein PM is covalently attached to SM, BASE is covalently attached to SM, and Sig is covalently attached to BASE directly or through a linkage group at a position other than the C5 position when BASE is a pyrimidine moiety, at a position other than the C8 position when BASE is a purine moiety, and at a position other than the C7 position when BASE is a 7-deazapurine moiety;

(ii)

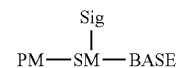

wherein
PM is a phosphate moiety,
SM is a furanosyl moiety,
BASE is a pyrimidine, a purine or a 7-deazapurine base moiety, and
Sig is a signalling moiety comprising a chelating structure or chelating component capable of chelating said metal or metal ion and providing a signal, wherein Sig comprises at least three carbon atoms, and wherein PM is covalently attached to SM, BASE is covalently attached to SM, and Sig is covalently attached to SM directly or through a linkage group; or Sig-PM-SM-BASE     (iii)

wherein
PM is a phosphate moiety,
SM is a furanosyl moiety,
BASE is a pyrimidine, a purine or a 7-deazapurine base moiety, and
Sig is a signalling moiety comprising a chelating structure or chelating component capable of chelating said metal or metal ion and providing a detectable signal; wherein Sig comprises at least three carbon atoms, and wherein PM is covalently attached to SM, BASE is covalently attached to SM, and Sig is covalently attached to PM directly or through a linkage group, provided that when said nucleotide or nucleotide analog structure (iii) is attached to an oligoribonucleotide or a polyribonucleotide, and provided that when Sig is attached through a chemical linkage to a terminal PM at the 3' position of a terminal ribonucleotide, said chemical linkage is not obtained through a 2',3' vicinal oxidation of a 3' terminal ribonucleotide previously attached to said oligoribonucleotide or polyribonucleotide; and said oligo- or polynucleotide of interest; and (C) either incorporating said modified or labeled nucleotides or modified or labeled nucleotide analogs (A)(1) into said oligo- or polynucleotide, and preparing a labeled oligo- or polynucleotide of interest, or preparing said oligo- or polynucleotide of interest from said oligo- or polynucleotide recited in step (A)(2) above.

165. A process for detecting the presence of a nucleic acid of interest in a sample, comprising:
providing a sample which may contain a nucleic acid of interest;
providing or generating (i) one or more detectable non-radioactively labeled oligonucleotides or polynucleotides, each of said detectable non-radioactively labeled oligonucleotides or polynucleotides comprising a sequence sufficiently complementary to said nucleic acid of interest or to a portion thereof to specifically hybridize therewith, wherein said detectable non-radioactively labeled oligonucleotides or polynucleotides comprise one or more detectable non-radioactively modified or labeled nucleotides or detectable non-radioactively modified or labeled nucleotide analogs, which nucleotide analogs can be attached to or coupled to or incorporated into DNA or RNA, and (ii) a sample that may contain said nucleic acid of interest;
forming in liquid phase hybrids comprising said detectable non-radioactively labeled oligonucleotides or polynucleotides specifically hybridized with said nucleic acid of interest;
separating or resolving in a gel said formed hybrids; and
detecting non-radioactively the separated or resolved hybrids to detect the presence of said nucleic acid of interest.

166. The process according to claim 165, further comprising after said hybrid forming step, the step of subjecting the liquid phase to nuclease treatment.

167. The process according to claim 165, wherein said nucleic acid of interest comprises DNA, RNA or DNA-RNA.

168. The process according to claim 165, wherein said one or more detectable oligonucleotides or polynucleotides comprises DNA, RNA or DNA-RNA.

169. The process according to claim 165, wherein said one or more detectable oligonucleotides or polynucleotides comprise biotin, iminobiotin, an electron dense component, a magnetic component, an enzyme, a hormone component, a metal-containing component, a fluorescent component, a chemiluminescent component, an antigen, a hapten, an antibody component, a chelating component or a combination of any of the foregoing.

170. The process according to claim 165, wherein said non-radioactive detection step is carried out directly or indirectly.

171. The process according to claim 165, wherein said detecting step is carried out by means of an enzymatic measurement, a fluorescent measurement, a chemiluminescent measurement, a microscopic measurement or an electron density measurement.

172. The process according to claim 165, wherein said detecting step comprises localizing said separated or resolved hybrids.

173. The process of any of claim 158, 161, 162, 163 or 164, wherein in said providing step, the chelating structure or chelating components provide a detectable signal that is radioactive, fluorogenic, fluorescent, chemiluminescent, electron dense or magnetic.

174. The process of any of claim 156, 158, 159, 161, 162 or 163, wherein said detecting step is carried out by a structure or component that is radioactive, fluorogenic, fluorescent, chemiluminescent, electron dense or magnetic.

175. The process of claim 174, wherein said detecting step is carried out radioactively.

176. The process of claim 175, wherein said radioactive detection is carried out by means of an isotope.

177. The process of claim 175, wherein said radioactive detection is carried out with an isotope comprising bismuth-206, bismuth-207, cobalt-60, gadolinium-153, strontium-90 or yttrium-90.

178. The process of claim 176, wherein said isotope is a β or γ emitter.

179. The process of any of claim 156, 158, 159, 161, 162, or 163, wherein in said detecting step, the chelating structure or chelating components have a chelated metal or metal ion comprising heavy metals or rare earth metals.

180. The process of claim 179, wherein said heavy metal comprises cobalt.

181. The process of any of claim 40, 42, 101, or 103, wherein said fluorescent aromatic or cycloaliphatic group comprises a fluorescent dye.

182. The process of any of claim 63, 64, 65, 67, 156, 159, 161, 162, 163, or 164, wherein said base comprises a pyrimidine analog or a purine analog.

183. The process of claim 182, wherein said pyrimidine analogs comprise thymidine analogs, uridine analogs, deoxyuridine analogs, cytidine analogs or deoxycytidine analogs.

184. The process of claim 183, wherein said uridine analogs comprise 5-bromo-2'-deoxyuridine-5'-phosphate.

185. The process of claim 183, wherein said deoxycytidine analogs comprise 5-hydroxymethyl-2'-deoxycytidylic acid.

186. The process of claim 182, wherein said purine analog comprises adenosine analogs, deoxyadenosine analogs, guanosine analogs or deoxyguanosine analogs.

187. The process of claim 186, wherein said adenosine analogs comprise tubericidin or toyocamycin.

188. A process for detecting the presence of a nucleic acid of interest in a sample, comprising:
providing or generating (i) one or more detectable non-radioactively labeled oligonucleotide or polynucleotide, each of said detectable non-radioactively labeled oligonucleotide or polynucleotide comprising a sequence sufficiently complementary to said nucleic acid of interest or to a portion thereof to specifically hybridize therewith, wherein said detectable non-radioactively labeled oligonucleotides or polynucleotides comprise one or more detectable non-radioactively modified or labeled nucleotides or detectable non-radioactively modified or labeled nucleotide analogs, which nucleotide analogs can be attached to, coupled to, or incorporated into DNA or RNA, and (ii) a sample that may contain said nucleic acid of interest;
forming liquid phase hybrids comprising said detectable non-radioactively labeled oligonucleotides or polynucleotides specifically hybridized with said nucleic acid of interest;
subjecting said liquid phase to nuclease treatment to digest non-hybridized single-stranded detectable non-radioactively labeled oligonucleotides or polynucleotides and leave said hybrids intact; and
detecting the hybrids non-radioactively to detect the presence of said nucleic acid of interest.

189. A process for detecting the presence of a nucleic acid of interest in a sample, comprising:
providing or generating (i) a detectable non-radioactively labeled oligonucleotide or polynucleotide, said detectable non-radioactively labeled oligonucleotide or polynucleotide comprising a sequence sufficiently complementary to said nucleic acid of interest or to a portion thereof to specifically hybridize therewith, wherein said detectable non-radioactively labeled oligonucleotide or polynucleotide comprises one or more detectable non-radioactively modified or labeled nucleotides or detectable non-radioactively modified or labeled nucleotide analogs, which nucleotide analogs can be attached to or coupled to or incorporated into DNA or RNA, and (ii) a sample that may contain said nucleic acid of interest;

forming in liquid phase, hybrids comprising said detectable non-radioactively labeled oligonucleotide or polynucleotide specifically hybridized with said nucleic acid of interest; and detecting hybrids non-radioactively to detect the presence of said nucleic acid of interest.

190. The process according to claim 189, further comprising a treatment that acts upon a non-hybridized detectable non-radioactiviely labeled oligonucleotide or polynucleotide and leaves a hybridized detectable non-radioactively labeled oligonucleotide or polynucleotide intact.

191. The process according to claim 190 wherein said treatment is a nuclease treatment.

192. The process according to claim 188 or 191 wherein said nuclease treatment is carried out by S1 nuclease, Exonuclease I from *E. coli*, or a combination thereof.

193. The process according to any of claim 188, 189, 190 or 191 further comprising separating or resolving in a gel said formed hybrids.

194. The process according to claim 188 or 189, wherein said nucleic acid of interest comprises DNA, RNA or DNA-RNA.

195. The process according to claim 188 or 189, wherein said detectable oligonucleotide or polynucleotide comprises DNA, RNA or DNA-RNA.

196. The process according to claim 188 or 189, wherein said detectable oligonucleotide or polynucleotide comprises biotin, iminobiotin, an electron dense component, a magnetic component, an enzyme, a hormone component, a metal-containing component, a fluorescent component, a chemiluminescent component, an antigen, a hapten, an antibody component, a chelating component or a combination of any of the foregoing.

197. The process according to claim 188 or 189, wherein said non-radioactive detection step is carried out directly or indirectly.

198. The process according to claim 188 or 189, wherein said detecting step is carried out by means of an enzymatic measurement, a fluorescent measurement, a chemiluminescent measurement, a microscopic measurement or an electron density measurement.

* * * * *

UNITED STATES PATENT AND TRADEMARK OFFICE
CERTIFICATE OF CORRECTION

| | | |
|---|---|---|
| PATENT NO. | : 8,097,405 B1 | Page 1 of 1 |
| APPLICATION NO. | : 08/486069 | |
| DATED | : January 17, 2012 | |
| INVENTOR(S) | : Elazar Rabbani et al. | |

It is certified that error appears in the above-identified patent and that said Letters Patent is hereby corrected as shown below:

On page 1, right column, on the line immediately after (74) Attorney, Agent or Firm - Natalie Bogdanos, Esq.;. "Elie Gendloff, Esq." should be changed to --Ronald C. Fedus, Esq.--

Signed and Sealed this
Twenty-eighth Day of February, 2012

David J. Kappos
*Director of the United States Patent and Trademark Office*